US007001438B2

(12) United States Patent
Santarsiero et al.

(10) Patent No.: US 7,001,438 B2
(45) Date of Patent: Feb. 21, 2006

(54) METHOD FOR PERFORMING SUBMICROLITER CRYSTALLIZATION EXPERIMENTS WITH HIGH EXPERIMENT TO EXPERIMENT PRECISION

(75) Inventors: Bernard D. Santarsiero, Chicago, IL (US); Raymond C. Stevens, La Jolla, CA (US); Peter G. Schultz, La Jolla, CA (US); Joseph M. Jaklevic, Lafayette, CA (US); Derek T. Yegian, Oakland, CA (US); Earl W. Cornell, Antioch, CA (US); Robert A. Nordmeyer, San Leandro, CA (US)

(73) Assignee: The Regents of the University of California, Oakland, CA (US)

( * ) Notice: Subject to any disclaimer, the term of this patent is extended or adjusted under 35 U.S.C. 154(b) by 173 days.

(21) Appl. No.: 10/119,332

(22) Filed: Apr. 8, 2002

(65) Prior Publication Data

US 2002/0173052 A1    Nov. 21, 2002

Related U.S. Application Data

(63) Continuation of application No. 09/851,397, filed on May 7, 2001, now Pat. No. 6,630,006, which is a continuation-in-part of application No. 09/336,134, filed on Jun. 18, 1999, now Pat. No. 6,296,673.

(51) Int. Cl.
*B01D 9/00* (2006.01)
*G01N 33/00* (2006.01)
(52) U.S. Cl. .................. 23/295 R; 436/86; 436/174
(58) Field of Classification Search .............. 23/295 R; 436/86, 174
See application file for complete search history.

(56) References Cited

U.S. PATENT DOCUMENTS

| 4,263,010 | A | 4/1981 | Randolph .................. 23/230 A |
| 4,668,584 | A | 5/1987 | Uzgiris et al. .............. 428/408 |
| 4,755,363 | A | 7/1988 | Fujita et al. ................ 422/245 |
| 4,833,233 | A | 5/1989 | Carter ........................ 530/363 |
| 4,886,646 | A | 12/1989 | Carter et al. ................ 422/245 |
| 4,900,147 | A | 2/1990 | Bowley et al. |
| 4,909,933 | A | 3/1990 | Carter et al. |
| 4,919,899 | A | 4/1990 | Herrmann et al. .......... 422/245 |
| 5,009,861 | A | 4/1991 | Plass-Link |
| 5,013,531 | A | 5/1991 | Snyder et al. |
| 5,076,698 | A | 12/1991 | Smith et al. |
| 5,078,975 | A | 1/1992 | Rhodes et al. .............. 422/253 |
| 5,096,676 | A | 3/1992 | McPherson et al. ........ 422/245 |
| 5,106,592 | A | 4/1992 | Stapelmann et al. |
| 5,124,935 | A | 6/1992 | Wallner et al. |
| 5,193,685 | A | 3/1993 | Trevithick |
| 5,221,410 | A | 6/1993 | Kushner et al. ............ 156/600 |
| 5,256,241 | A | 10/1993 | Noever |
| 5,419,278 | A | 5/1995 | Carter ........................ 117/206 |
| 5,544,254 | A | 8/1996 | Hartley et al. |
| 5,581,476 | A | 12/1996 | Osslund |
| 5,641,681 | A | 6/1997 | Carter ........................... 436/4 |
| 5,643,540 | A | 7/1997 | Carter et al. ............. 422/245.1 |
| 5,790,421 | A | 8/1998 | Osslund |
| 5,855,753 | A | 1/1999 | Trau et al. |
| 5,872,010 | A | 2/1999 | Karger et al. ............... 436/173 |
| 5,873,394 | A | 2/1999 | Meltzer ...................... 141/130 |
| 5,973,779 | A | 10/1999 | Ansari et al. |
| 5,985,356 | A | 11/1999 | Schultz et al. |
| 5,997,636 | A | 12/1999 | Gamarnik et al. |
| 6,036,920 | A | 3/2000 | Pantoliano et al. |
| 6,039,804 | A | 3/2000 | Kim et al. ................... 117/206 |
| 6,057,159 | A | 5/2000 | Lepre .......................... 436/86 |
| 6,069,934 | A | 5/2000 | Verman et al. |
| 6,148,878 | A | 11/2000 | Ganz et al. |
| 6,268,158 | B1 | 7/2001 | Pantoliano et al. |
| 6,297,021 | B1 | 10/2001 | Nienaber et al. |
| 6,303,322 | B1 | 10/2001 | Pantoliano et al. |
| 6,360,792 | B1 | 3/2002 | Ganz et al. |
| 6,402,837 | B1 | 6/2002 | Shtrahman et al. ......... 117/200 |
| 6,404,849 | B1 | 6/2002 | Olson et al. |
| 6,417,007 | B1 | 7/2002 | Gittleman et al. |
| 6,558,623 | B1 | 5/2003 | Ganz et al. |
| 6,579,358 | B1 | 6/2003 | DeLucas et al. |
| 6,592,824 | B1 | 7/2003 | DeLucas et al. |
| 2001/0006807 | A1 | 7/2001 | Bray et al. .................. 435/235 |
| 2001/0016191 | A1 | 8/2001 | Osslund |
| 2001/0016314 | A1 | 8/2001 | Anderson et al. |
| 2001/0019845 | A1 | 9/2001 | Bienert et al. |
| 2001/0027745 | A1 | 10/2001 | Weigl et al. |
| 2001/0032582 | A1 | 10/2001 | DeTitta et al. |

(Continued)

FOREIGN PATENT DOCUMENTS

EP      0 553 539 A1    4/1993

(Continued)

OTHER PUBLICATIONS

Stewart, P.D.S. et al., "Practical Experimental Design Techniques for Automatic and Manual Protein Crystallization" J Crystal Growth 196, pp. 665-673.

(Continued)

*Primary Examiner*—Stanley S. Silverman
(74) *Attorney, Agent, or Firm*—Peters, Verny, Jones & Schmitt, L.L.P.; Howard M. Peters

(57) ABSTRACT

A method is provided for forming crystallization experiments for a molecule, the method comprising forming a plurality of crystallization experiments that comprise a molecule to be crystallized and a composition that varies among the plurality of crystallization experiments, the crystallization experiments having a volume less than 1 microliter, the volumes of the plurality of crystallization experiments varying among the experiments by less than 25 nL.

82 Claims, 65 Drawing Sheets

U.S. PATENT DOCUMENTS

| | | |
|---|---|---|
| 2001/0055669 A1 | 12/2001 | Schultz et al. |
| 2001/0055775 A1 | 12/2001 | Schultz et al. |
| 2002/0022250 A1 | 2/2002 | Hendrickson et al. |
| 2002/0029814 A1 | 3/2002 | Unger et al. ............... 137/821 |
| 2002/0048610 A1 | 4/2002 | Cima et al. |
| 2002/0054663 A1 | 5/2002 | Olson et al. |
| 2002/0062783 A1 | 5/2002 | Bray |
| 2002/0064485 A1 | 5/2002 | DeLucas et al. ............ 422/102 |
| 2002/0067800 A1 | 6/2002 | Newman et al. |
| 2002/0106318 A1 | 8/2002 | DeLucas et al. |
| 2002/0110816 A1 | 8/2002 | Santarsiero et al. |
| 2002/0143153 A1 | 10/2002 | Santarsiero et al. |
| 2002/0144738 A1 | 10/2002 | Unger et al. |
| 2002/0160426 A1 | 10/2002 | Santarsiero et al. |
| 2002/0164812 A1 | 11/2002 | DeLucas |
| 2002/0169512 A1 | 11/2002 | Stewart |
| 2002/0182637 A1 | 12/2002 | Santarsiero et al. |
| 2003/0000597 A1 | 1/2003 | Ganz et al. |
| 2003/0022383 A1 | 1/2003 | DeLucas |
| 2003/0022384 A1 | 1/2003 | DeLucas |
| 2003/0027348 A1 | 2/2003 | DeLucas et al. |
| 2003/0027997 A1 | 2/2003 | Bray et al. |
| 2003/0096421 A1 | 5/2003 | DeLucas et al. |

FOREIGN PATENT DOCUMENTS

| | | |
|---|---|---|
| JP | 02001013054 A | 1/2001 |
| WO | WO 99/04361 A1 | 1/1999 |
| WO | WO 00/60345 | 12/2000 |
| WO | WO 01/92293 A2 | 12/2001 |
| WO | WO 02/093139 A2 | 11/2002 |
| WO | WO 01/26797 A2 | 4/2003 |
| WO | WO 01/26797 A3 | 4/2003 |

OTHER PUBLICATIONS

Baldock, P. et al., "A Comparison of Microbatch And Vapor Diffusion For Initial Screening of Crystallization Conditions" J. Crystal Growth 168; pp. 170-174.

Cudney, B. et al., "Screening and Optimization Strategies For Macromolecular Crystal Growth", ACTA Crystallogr D50, pp. 414-423.

McPherson, A., "Two Approaches to the Rapid Screening of Crystallization Conditions"J Crystal Growth 122; pp. 161-167.

Ward, K.B. et al., "Automating Crystallization Experimients. In: Crystallization of Nucleic Acids and Proteins: a Practical Approach" eds. A. Ducruix & R. Giege, Oxford University Press, New York; pp. 291-310.

Weber, P.C., "Overview of Protein Crystallization Methods" Methods Enzymol, 276, pp. 13-22 (1997).

McPherson, A. "Crystallization of Biological Marcromolecules" Cold Spring Harbor Laboratory Press; (1999).

McPherson, A. "Crystallization of Macromolecules: general principals" Methods Enzymol, 114; pp. 112-120 (1985).

McPherson, A. "Use of Polyethylene Glycol in the Crystallization of Macromolecules" Methods Enzymol; 114; pp. 120-125 (1985).

McPherson, A. "Crystallization of Proteins by Variation of pH or Temperature", Methods Enzymol, 114; pp. 125-127.

Jancarik, J. et al., "Sparse Matrix Sampling: A Screening Method For Crystallization of Proteins", J. Appl. Cryst. 24; pp. 409-411 (1991).

Gilliland, G.L. et al., "Biological Macromolecule Crystallization Database, Version 3.0: New Features, Data and the NASA Archive for Protein Crystal Growth Data" ACTA Crystallogr. D50; pp. 408-413 (1994).

Perrakis, A et al., Protein Microcrystals and the Design of a Micro-Diffractometer: Current Experience and Plans at EMBL and ESRF/ID13; ACTA Crystallogr D55; pp. 1765-1770 (1999).

Pebay-Peyroula, R. et al., "X-ray Structure of Bacteriorhodopsin at 2.5 Angstroms from Microcrystals Grown Lipidic Cubic Phases" SCIENCE 277; pp. 1676-1681 (1997).

Sibille, L., Clunie, J.C., Baird, J.K. Solvent evaporation rates in the closed capillary vapor diffusion method of protein crystal growth. *J. Cryst. Growth* 110, 80-88 (1991).

Montelione, G, Anderson, S: Structural genomics: keystone for a human proteome project. *Nature Struct Biol* (1999) 6(1):11-12.

Burley, SK, Almo, SC, Bonanno, JB, Capel, M, Chance, MR, Gaasterland, T, Lin, D, Sali, A, Studier, FW, Swaminathan, S: Structural genomics: beyond the Human Genome Project. *Nature Genet* (1999) 23:151-157.

Gaasterland, T: Structural genomics: Bioinformatics in the driver's seat. *Nature Biotechnol* (1998) 16:625-627.

Rost, B: Marrying structure and genomics. *Structure* (1998) 6:259-263.

Shapiro, L, Lima, CD: The Argonne Structural Genomics Workshop: Lamaze class for the birth of a new science. *Structure* (1998) 6:265-267.

Ducruix, A, Giege, R (Eds): *Crystallization of nucleic acids and proteins. A practical approach. Second edition.* Oxford: Oxford University Press; (1999).

D-Arcy, A: Crystallizing proteins—a rational approach? *Acta Crystallogr D* (1994) 50:469-471.

Stura, EA, Satterthwait, AC, Calvo, JC, Kaslow, DC, Wilson, IA: Reverse screening. *Acta Crystallogr D* (1994) 50:448-455.

Hampton Research Homepage on World Wide Web at URL: http://www.hamptonresearch.com.

Emerald BioStructures Homepage on World Wide Web at URL: http://www.emeraldbiostructures.com.

Carter, C, Jr: Efficient factorial designs and the analysis of macromolecular crystal growth conditions. *Methods* (1990) 1(1):12-24.

Carter, C, Jr: Design of crystallization experiments and protocols. *Crystallization of nucleic acids and proteins. A practical approach.* Ducruix, A, Giege, R, (Eds): New York: IRL Press; (1992):47-71.

Jones, N, Swartzendruber, JK, Deeter, JB, Landis, ND, Clawson, DK: Apocalypse now: update on automated protein crystallization using the new ACA vapor diffusion plate. *Acta Crystallogr A* (1987) 43(Supplement): C275.

Douglas Instruments Homepage on World Wide Web at URL: http://www.douglas.co.uk/home.htm A good introduction to the application of the microbatch technique for high-throughput work is available at the Web Site of Douglas Instruments [URL: http://www.douglas.co.uk/proposal.htm—The use of microbatch for large scale crystallization projects].

Cyberlabs Homepage on World Wide Web at URL: http://www.gilson.com/cyberprd.htm First commercially available robotics system for protein crystal growth. The Cyberlabs instrument has undergone revisions over the years. They are now addressing the need to create imaging stations for protein crystal analysis.

Baird, JK: Theory of protein crystal nucleation and growth controlled by solvent evaporation. *J Cryst Growth* (1999) 204:553-562.

Bullock, E. and E.C. Pyatt, Apparatus for the growth of crystals from small volumes of solution, in J. Phys. E. 1972. 412-13.

Luft, J.R., D.M. Rak, and G.T. DeTitta, Microbatch macromolecular crystallization in micropipettes, in J. Cryst. Growth. 1999. 450-455.

Pusey, M. and R. Naumann, Growth kinetics of tetragonal lysozyme crystals, in J. Cryst. Growth. 1986. 593-9.

Reshetnyak, I.I., Effect of ultrasound on crystallization kinetics in small volumes of solutions, in Akust. Zh. 1975. 99-103.

Rippon, G.D., A. Patak, and A.T. Marshall, Improved microdroplet method for quantitative x-ray microanalysis of small fluid samples, in Micron. 1993. 17-21.

Tebbutt, J.S., T. Marshall, and R.E. Challis, Monitoring of crystallization phenomena by ultrasound, in Electron. Lett. 1999. 90-91.

Zeppezauer, M., H. Eklund, and E.S. Zeppezauer, Micro diffusion cells for the growth of single protein crystals by means of equilibrium dialysis, in Arch. Biochem. Biophys. 1968. 564-73.

Chayen, N.E., Shaw Stewart, P.D., Blow, D.M.: Microbatch crystallization under oil—a new technique allowing many small-volume cyrstallization trials. J Crystal Growth (1992) 122:176-180.

Chayen, N.E., Shaw Stewart, P.D. , Baldock, P.: New developments of the IMPAX small-volume automated crystallization system. Acta Cryst (1994) D50:456-458.

Wilson, S.A., et al.: Crystallization of and preliminary X-ray data for the negative regulator (AmiC) of the amidase operon of Pseudomonas aeruginosa. J Mol Biol (1991), 222: 869-871.

Varadarajan, R. and F.M. Richards: Crystallographic structures of ribonuclease S variants with nonpolar substitution at position 13: packing and cavities. Biochemistry (1992), 31: 12315-12327.

Rawas, A., et al.: Preliminary crystallographic studies on duck ovotransferrin. J Mol Biol (1989), 208: 213-214.

Evans, P.R., G.W. Farrants, and M.C. Lawrence: Crystallographic structure of allosterically inhibited phosphofructokinase at 7 A resolution. J Mol Biol (1986), 191:713-720.

Rubin, B., Talafous, J., Larson, D.: Minimal intervention robotic protein crystallization. J. Cryst Growth (1991) 110: 156-163.

Kelders, H.A., et al.: Automated protein crystallization and a new crystal form of a subtilisin:eglin complex. Protein Eng (1987), 1: 301-3.

Oldfield, T.J., Ceska, T.A., Brady, R.L. A flexible approach to automated protein crystallization. J Appl Cryst (1991) 24:255-260.

Andersen, G.R., Nyborg, J. A spreadsheet approach to automated protein crystallization. J Appl Cryst (1996) 29: 236-240.

Morris, D.W., Kim, C.Y., McPherson, A. Automation of protein crystallization trials: use of a robot to deliver reagents to a novel multi-chamber vapor diffusion plate. Biotechniques (1989) 7:522-527.

Swartzendruber, J.K., Jones, N.D. APOCALYPSE: an automated protein crystallization system. III. In the beginning: The genesis of software. (1988) p. 81 Annual Meeting of the American Crystallographic Association, Philadelphia, PA.

Weber, P.C., Cox, M.J. Experiments with automated protein crystal growth. (1987) p 28 Annual Meeting of the American Crystallographic Association, Philadelphia, PA.

Brodersen, D. E., Jenner, L. B., Anderson, G. R. and Nyborg, J. (1999). XAct: a program for construction, automated setup and bookkeeping of crystallization experiments. J. Appl. Crystallogr. 32: 1012-16.

Zeelen, J. Ph.; Hiltunen, J. K.; Ceska, T. A.; Wierenga, R. K. (1994) Crystallization experiments with 2-enoyl-CoA hydratase, using an automated 'fast-screening' crystallization protocol. Acta Crystallogr. D50: 443-447.

Diller, D.J., Hol, W.G.J. An accurate numerical model for calculating the equilibration rate of a hanging-drop experiment. *Acta Crystallogr.* D55, 656-663 (1999).

Pusey, M.L. et al., "Protein Crystal Growth" Growth Kinetics for Tetragonal Lysozyme Crystals, 261; pp. 6524-6529 (1986).

Cox, M. J. et al., "An Investigation of Protein Crystallization Parameters Using Successive Automated Grid Searches (SAGS)", *Journal of Crystal Growth,* vol. 90, Nos. 1-3, Jul. 1988, pp. 318-324.

Chayen, N. et al., "An Automated System for Micro-Batch Protein Crystallization and Screening", *J. Appl. Cryst.,* vol. 23 (1990), pp. 297-302.

Tisone, T., "Dispensing systems for miniaturized diagnostics", *IVD Technology Magazine* (Online), May 1998, 9 pages.

Berry, M. B., "Protein Crystallization: Theory and Practice", *Structure and Dynamics of E. coli Adenylate Kinase;* Thesis, Rice University, Houston, TX, (Online) (1995), 13 pages.

Yakovlev, Y. et al., "A Laboratory Apparatus for Crystal Growth from Solution", *Instruments and Experimental Techniques,* vol. 41, No. 2 (1998), pp. 157-161.

Casay, G. et al., "Laser scattering in a hanging drop vapor diffusion apparatus for protein crystal growth in a microgravity environment", *Journal of Crystal Growth,* vol. 122 (1992), pp. 95-101.

Gonzalez, F. et al., "Crocodile: An Automated Apparatus For Organic Crystal Growth From Solution", *Acta Astronautica,* vol. 25, No. 12 (1991), pp. 775-784.

Beckmann, W. et al., "The Effect Of Additives on Nucleation: A Low Cost Automated Apparatus", *Journal of Crystal Growth,* vol. 99 (1990), pp. 1061-1064.

Leonidas, D. et al., "Refined Crystal Structures of Native Human Angiogenin and Two Active Site Variants: Implications for the Unique Functional Properties of an Enzyme Involved in Neovascularisation During Tumour Growth", *J. Mol. Biol.,* vol. 285 (1999), pp. 1209-1233.

Cox, M. J. et al., "Experiments with Automated Protein Crystallization", *J. Appl. Cryst.,* vol. 20 (1987), pp. 366-373.

Ward, K.B. et al., "Automatic Preparation of Protein Crystals Using Laboratory Robotics and Automated Visual Inspection", *Journal of Crystal Growth,* vol. 90 (1988), pp. 325-339.

Soriano, T. et al., "ASTEC: an Automated System for Sitting-Drop Protein Crystallization", *J. Appl. Cryst.,* vol. 26 (1993), pp. 558-562.

Newman, A., "Send in the Robots", *Analytical Chemistry,* vol. 62, No. 1, Jan. 1, 1990, pp. 29A-34A.

"Automatic Protein Crystallization System", (Advertising Supplement), Douglas Instruments Ltd., London, (1990), 4 pages.

Stevens, R. C. et al., Research Proposal for development and testing of a system of robotics workstations dedicated to protein crystallization. E.O. Lawrence Berkeley National Laboratory and The Scripps Research Institute, pp. 2, 29-52 (Rev. May 1995).

Sali, A., "100,000 protein structures for the biologist", printed Apr. 1, 1999 from world wide web site http://guitar.rockefeller.edu/avalon/review/avalon.html, 7 pages.

"Functional Genomics", printed Apr. 1, 1999 from world wide web site http://www.bmb.psu.edu/simpson/16genome/Function.htm, 1 page.

Gaasterland, T., "The Role of Computational Biology In High-Throughput Structure Determination: Computation Before, During, and After Structural Genomics", printed Apr. 1, 1999 from world wide web site http://www-fq.mcs.anl.gov/~gaasterland/sg-review-slides.html, 14 pages.

"Crystallization Research Tools", vol. 9, No. 1 (1999), Hampton Research Corp., Laguna Niguel, CA., 63 pgs.

Arakali, Sheela V., Easley, Samantha, Luft, Joseph R. and Detitta, George T., Time Courses of Equilibration for Ammonium Sulfate, Sodium Chloride and Magnesium Sulfate Heptahydrate in the Z/3 Crystallization Plate, Acta Cryst (1994), D50, pp. 472-478.

Arakali, Sheela V., Luft, Joseph R. and Detitta, George T., Non-ideality of Aqueous Solutions of Polyethylene Glycol: Consequences for Its Use as a Macromolecular Crystallizing Agent in Vapor-Diffusion Experiments, Acta Cryst (1995), D51, pp. 772-779.

Barrett, Tracey E., Savva, Renos, Panayotou, George, Barlow, Tom, Brown, Tom, Jiricny, Josef and Pearl, Laurence H., Crystal Structure of a G:T/U Mismatch-Specific DNA Glycosylase: Mismatch Recognition by Complementary-Strand Interactions, Cell (1998), vol. 92, pp. 117-129.

Bauer, Alan J., Rayment, Ivan, Frey, Perry A. and Holden, Hazel M., The Isolation, Purification, and Preliminary Crystallographic Characterization of UDP-Galactose-4-Epimerase from *Escherichia coli*. PROTEINS: Structure, Function and Genetics (1991), vol. 9, pp. 135-142.

Bauer, Alan J., Rayment, Ivan, Frey, Perry A. and Holden, Hazel M., The Molecular Structure of UDP-Galactose 4-Epimerase From *Escherichia coli*, Determined at 2.5 A Resolution, PROTEINS: Structure, Function and Genetics (1992), vol. 12, pp. 372-381.

Blow, D.M., Chayen, N.E., Lloyd, L.F. and Saridakis, E., Control of nucleation of protein crystals, Protein Science (1994), vol. 3, pp. 1638-1643.

Chayen, Naomi E., Radcliffe, Jonathan W. and Blow, David M., Control of nucleation in the crystallization of lysozyme, Protein Science (1993), vol. 2, pp. 113-118.

Chayen, Naomi E., Gordon, Elspeth J., Phillips, Simon E.V., Saridakis, E.G., and Zagalsky, Peter F., Crystallization and initial X-ray analysis of β-crustacyanin, the dimer of apoproteins $A_2$ and $C_1$, each with a bound astaxanthin molecule, Acta Cryst. (1996), D52, pp. 409-410.

Chayen, Naomi E., A novel technique for containerless protein crystallization, Protein Engineering (1996), vol. 9, No. 10, pp. 927-929.

Chayen, Naomi E., Conti, Elena, Vielle, Claire and Zeikus, J. Gregory, Crystallization and initial X-ray analysis of xylose isomerase from *Thermotoga neapolitana*, Acta Cryst. (1997), D53, pp. 229-230.

Chayen, Naomi E., Comparative Studies of Protein Crystallization by Vapour-Diffusion and Microbatch Techniques, Acta Cryst. (1998), D54, pp. 8-15.

Chayen, Naomi E., Recent advances in methodology for the crystallization of biological macromolecules, Journal of Crystal Growth (1999), vol. 198/199, pp. 649-655.

Chayen, Naomi E., Crystallization with oils: a new dimension in macromolecular crystal growth, Journal of Crystal Growth (1999), vol. 196, pp. 434-441.

Conti, Elena, Lloyd, Lesley F., Akins, John, Franks, Nick P. and Brick, Peter, Crystallization and preliminary diffraction studies of firefly luciferase from *Photinus pyralis*, Acta Cryst. (1996), D52, pp. 876-878.

Cowan-Jacob, Sandra W., Rahuel, Joseph, Nagai, Atsuko, Isasaki, Genji and Ohta, Diasaku, Crystallization and preliminary crystallographic analysis of cabbage histidinol dehydrogenase, Acta Cryst. (1996), D52, pp. 1188-1190.

D'Arcy, A., Elmore, C., Stihle, M. and Johnston, J.E., A novel approach to crystallizing proteins under oil, Journal of Crystal Growth (1996), vol. 168, pp. 175-180.

Detitta, George T. and Luft, Joseph R., Rate of Water Equilibration in Vapor-Diffusion Crystallization: Dependence on the Residual Pressure of Air in the Vapor Space, Acta Cryst. (1995), D51, pp. 786-791.

Erlandsen, Heidi, Martinez, Aurora, Knappskog, Per M., Haavik, Jan, Hough, Edward and Flatmark, Torgeir, Crystallization and preliminary diffraction analysis of a truncated homodimer of human phenylalanine hydroxylase, FEBS Letters (1997), vol. 406, pp. 171-174.

Fisher, Andrew J., Raushel, Frank M., Baldwin, Thomas O. and Rayment, Ivan, Three-Dimensional Structure of Bacterial Luciferase from *Vibrio* harveyi at 2.4 Å Resolution, Biochemistry (1995), vol. 34, pp. 6581-6586.

Fisher, Andrew J., Thompson, Thomas B., Thoden, James B., Baldwin, Thomas O. and Rayment, Ivan, The 1.5-Å Resolution Crystal Structure of Bacterial Luciferase in Low Salt Conditions, Journal of Biological Chemistry (1996), vol. 271, No. 36, pp. 21956-21968.

Harata, K., Nagahora, H. and Jigami, Y., X-ray Structure of Wheat Germ Agglutinin Isolectin 3, Acta Cryst. (1995), D51, pp. 1013-1019.

Holden, Hazel M., Ito, Masaaki, Hartshorne, David J. and Rayment, Ivan, X-ray Structure Determination of Telokin, the C-terminal Domain of Myosin Light Chain Kinase, at 2•8 Å Resolution, J. Mol. Biol. (1992), vol. 227, pp. 840-851.

Jurisica, I., Rogers, P., Glasgow, J.I., Fortier, S., Luft, J.R., Wolfley, J.R., Bianca, M.A., Weeks, D.R., Detitta, G.T., Intelligent decision support for protein crystal growth, IBM Systems Journal (2001), vol. 40, No. 2, pp. 394-409.

Kanikula, Agnes M., Liao, Hans H., Sakon, Joshua, Holden, Hazel M. and Rayment, Ivan, Crystallization and Preliminary Crystallographic Analysis of a Thermostable Mutant of Kanamycin Nucleotidyltransferase, Archives of Biochemistry and Biophysics (1992), vol. 295, No. 1, pp. 1-4.

Korkhin, Yakov, Frowlow, Felix, Bogin, Oren, Peretz, Moshe, Kalb, A. Joseph and Burstein, Yigal, Crystalline alcohol dehydrogenases from the mesophilic bacterium *Clostridium beijerinckii* and the thermophilic bacterium *Thermoanaerobium brockii*: preparation, characterization and molecular symmetry, Acta Cryst. (1996), D52, pp. 882-886.

Kostrewa, Dirk and Winkler, Fritz K., $Mg^{2+}$ Binding to the Active Site of *Eco*RV Endonuclease: A Crystallographic Study of Complexes with Substrate and Product DNA at 2 Å Resolution, Biochemistry (1995), vol. 34, pp. 683-696.

Lesburg, Charles A., Cable, Michael B., Ferrari, Eric, Hong, Zhi, Mannarino, Anthony F. and Weber, Patricia C., Crystal structure of the RNA-dependent RNA polymerase from hepatitis C virus reveals a fully encircled active site, Nature Structural Biology (1999), vol. 6, No. 10, pp. 937-943.

Lilley, Glenn G., Barbosa, Joao A.R.G. and Pearce, Lesley A., Expression in *Escherichia coli* of the Putative N-Acetylneuraminate Lyase Gene (nanA) from *Haemophilus influenzae*: Overproduction, Purification, and Crystallization, Protein Expression and Purification (1998), vol. 12, pp. 295-304.

Lorber, Bernard and Giege, Richard, Containerless protein crystallization in floating drops: application to crystal growth monitoring under reduced nucleation conditions, Journal of Crystal Growth (1996). vol. 168, pp. 204-215.

Lloyd, Lesley F., Brick, Peter, Mei-Zhen, Lou, Chayen, Naomi E. and Blow, David M., Many Crystal Forms of Human Immunodeficiency Virus Reverse Transcriptase, J. Mol. Biol. (1991), vol. 217, pp. 19-22.

Lloyd, Lesley F., Brick, Peter and Blow, David M., Crystallization studies on HIB-1 reverse transcriptase, Journal of Crystal Growth (1992), vol. 122, pp. 355-359.

Luft, Joseph R. and Detitta, George T., Hangman: a macromolecular hanging-drop vapor-diffusion technique, J. App. Cryst. (1992), vol. 25, pp. 324-325.

Luft, Joseph R., Arakali, Sheela V., Kirisits, Mary J., Kalenik, Jennifer, Ilona Wawrzk, Cody, Vivian, Pangborn, Walter A. and Detitta, George T., A Macromolecular Crystallization Procedure Employing Diffusion Cells of Varying Depths as Reservoirs to Tailor the Time Course of Equilibration in Hanging- and Sitting-Drop Vapor-Diffusion and Microdialysis Experiments, J. Appl. Cryst. (1994), vol. 27, pp. 443-452.

Luft, Joseph R. and Detitta, George T., Chaperone Salts, Polyethylene Glycol and Rates of Equilibration in Vapor-Diffusion Crystallization, Acta Cryst. (1995), D51, pp. 780-785.

Luft, Joseph R., Albright, Douglas T., Baird, James K. and Detitta, George T., The Rate of Water Equilibration in Vapor-Diffusion Crystallization: Dependence on the Distance from the Droplet to the Reservoir, Acta Cryst. (1996), D52, pp. 1098-1106.

Luft, Joseph R. and Detitta, George T., Kinetic Aspects of Macromolecular Crystallization, Methods in Enzymology (1997), vol. 276, No. 7, pp. 110-130.

Luft, Joseph R. and Detitta, George T., A method to produce microseed stock for use in the crystallization of biological macromolecules, Acta Cryst. (1999), D55, pp. 988-993.

Luft, Joseph R., Rak, Dawn M. and Detitta, George T., Microbatch macromolecular crystallization on a thermal gradient, Journal of Crystal Growth (1999), vol. 196, pp. 447-449.

Luft, Joseph R., Wolfley, Jennifer, Jurisica, Igor, Glasgow, Janice, Fortier, Suzanne and Detitta, George T., Macromolecular crystallization in a high throughput laboratory—the search phase, Journal of Crystal Growth (2001), vol. 232, pp. 591-595.

McPherson, Alexander, Koszelak, Stanley, Axelrod, Herbert, Day, John, Williams, Roger, Robinson, Lindsay, McGrath, Mary and Cascio, Duilio, An Experiment Regarding Crystallization of Soluble Proteins in the Presence of β-Octyl Glucoside, Journal of Biological Chemistry (1986), vol. 261, No. 4, pp. 1969-1975.

O'Hara, Bernard P., Hemmings, Andrew M., Buttle, David j. and Pearl, Laurence H., Crystal Structure of Glycyl Endopeptidase from *Carica papaya*: A Cysteine Endopeptidase of Unusual Substrate Specificity, Biochemistry (1995), vol. 34, pp. 13190-13195.

Panayotou, George, Brown, Tom, Barlow, Tom, Pearl, Laurence H. and Savva, Renos, Direct Measurement of the Substrate Preference of Uracil-DNA Glycosylase, Journal of Biological Chemistry (1998), vol. 273, No. 1, pp. 45-50.

Pearl, Laurence H., Hemmings, Andrew M., Nucci, Roberto and Rossi, Mose, Crystallization and Preliminary X-ray Analysis of the β-Galactosidase from the Extreme Thermophilic Archaebacterium *Sulfolobus solfataricus*, J. Mol. Biol. (1993), vol. 229, pp. 561-563.

Pearl, Laurence H., Demasi, Domenico, Hemmings, Andrew M., Sica, Filomena, Mazzarella, Lelio, Raia, Carlo A., D'Auria, Sabato and Rossi, Mose, Crystallization and Preliminary X-ray Analysis of an NAD+-dependent Alcohol Dehydrogenase from the Extreme Thermophilic Archaebacterium *Sulfolobus solfataricus*, J. Mol. Biol. (1993), vol. 229, pp. 782-784.

Pearl, Laurence, O'Hara, Bernard, Drew, Robert and Wilson, Stuart, Crystal structure of AmiC: the controller of transcription antitermination in the amidase operon of *Pseudomonas aeruginosa*. EMBO Journal (1994), vol. 13, No. 24, pp. 5810-5817.

Pearl, Laurence H. and Prodromou, Chrisostomos, Structure, Function, and Mechanism of the Hsp90 Molecular Chaperone, Section of Structural Biology, Institute of Cancer Research, Chester Beatty Laboratories (2002), pp. 157-186.

Peapus, Diane H., Janes, Robert W. and Wallace, B.A., Preliminary Crystallization and X-ray Analysis of Orthorhombic Human Endothelin, J. Mol. Biol. (1993), vol. 234, pp. 1250-1252.

Petsko, Gregory A., Preparation of Isomorphous Heavy-Atom Derivatives, Methods in Enzymology (1985), vol. 114, No. 13, pp. 147-155.

Prodromou, Chrisostomos, Piper, Peter W. and Pearl, Laurence H., Expression and Crystallization of the Yeast Hsp82 Chaperone, and Preliminary X-Ray Diffraction Studies of the Amino-Terminal Domain, PROTEINS: Structure, Function, and Genetics (1996), vol. 25, pp. 517-522.

Prodromou, Chrisostomos, Roe, S. Mark, O'Brien, Ronan, Ladbury, John E. Piper, Peter W. and Pearl, Laurence H., Identification and Structural Characterization of the ATP/ADP-Binding Site in the Hsp90 Molecular Chaperone, Cell (1997), vol. 90, pp. 65-75.

Sakon, Joshua, Liao, Hans H., Kanikula, Agnes M., Benning, Matthew M., Rayment, Ivan and Holden, Hazel M., Molecular Structure of Kanamycin Nucleotidyltransferase Determined to 3.0-Å Resolution, Biochemistry (1993), vol. 32, pp. 11977-11984.

Savva, Renos and Pearl, Laurence H., Crystallization and Preliminary X-ray Analysis of the Uracil-DNA Glycosylase DNA Repair Enzyme from Herpes Simplex Virus Type 1, J. Mol. Biol. (1993), vol. 234, pp. 910-912.

Savva, Renos and Pearl, Laurence H., Cloning and Expression of the Uracil-DNA Glycosylase Inhibitor (UGI) From Bacteriophage PBS-1 and Crystallization of a Uracil-DNA Glycosylase-UGI Complex, PROTEINS: Structure, Function, and Genetics (1995), vol. 22, pp. 287-289.

Saridakis, Emmanuel E.G., Shaw Stewart, Patrick D., Lloyd, Lesley F. and Blow, David M., Phase Diagram and Dilution Experiments in the Crystallization of Carboxypeptidase $G_2$, Acta Cryst. (1994), D50, pp. 293-297.

Shaw Stewart, P.D. and Khimasia, M., Predisposed Gradient Matrices—a New Rapid Method of Finding Crystallization Conditions, Acta Cryst. (1994), D50, pp. 441-442.

Sica, Filomena, Adinolfi, Salvatore, Vitagliano, Luigi, Zagari, Adriana, Capasso, Sante and Mazzarella, Lelio, Cosolute effect on crystallization of two dinucleotide complexes of bovine seminal ribonuclease from concentrated salt solutions, Journal of Crystal Growth (1996), vol. 168, pp. 192-197.

Sivaraman, J., Coloumbe, Rene, Magny, Marie-Claude, Mason, Patrizia, Mort, John S. and Cygler, Miroslaw, Crystallization of rat procathepsin B, Acta Cryst. (1996), D52, pp. 874-875.

Thomson, James, Ratnaparkhi, Girish S., Varadarajan, Raghavan, Sturtevant, Julian M. and Richards, Frederic M., Thermodynamic and Structural Consequences of Changing a Sulfur Atom to a Methylene Group in the M13Nle Mutation in Ribonuclease-S, Biochemistry (1994), vol. 33, pp. 8587-8593.

Zagari, A., Savino, L., Capasso, S., Sica, F. and Mazzarella, L., Crystallization and preliminary X-ray analysis of the river buffalo (*Bubalus bubalis L.*) BB phenotype carbonmonoxyhaemoglobin, Acta Cryst. (1994), D50, pp. 778-780.

Zhou, Genfa, Parthasarathy, Gopalakrishnan, Somasundaram, Thayumanasamy, Ables, Andrea, Roy, Lance, Strong, Scott J., Ellington, W. Ross and Chapman, Michael S., Expression, purification from inclusion bodies, and crystal characterization of a transition state analog complex of arginine kinase: A model for studying phosphagen kinases, Protein Science (1997), vol. 6, pp. 444-449.

U.S. Appl. No. 10/119,237, filed Apr. 8, 2002, Santarsiero et al.

U.S. Appl. No. 10/323,037, filed Dec. 18, 2002, Santarsiero et al.

U.S. Appl. No. 10/323,319, filed Dec. 18, 2002, Santarsiero et al.

U.S. Appl. No. 10/323,378, filed Dec. 18, 2002, Santarsiero et al.

U.S. Appl. No. 10/322,952, filed Dec. 18, 2002, Santarsiero et al.

U.S. Appl. No. 10/323,949, filed Dec. 18, 2002, Santarsiero et al.

U.S. Appl. No. 10/323,054, filed Dec. 18, 2002, Santarsiero et al.

U.S. Appl. No. 10/324,022, filed Dec. 18, 2002, Santarsiero et al.

U.S. Appl. No. 10/334,336, filed Dec. 31, 2002, Santarsiero et al.

U.S. Appl. No. 10/334,396, filed Dec. 31, 2002, Santarsiero et al.

Abola, Enrique et al., "Automation of X-ray crystallography", Natural Structural Biology, Structural Genomics Supplement, (Nov. 2000), pp. 973-977.

Presentation: "PBD/Research/Research Areas/ AUTOMATION" (Feb. 28, 2002), http://www.lbl.gov/LBL-Programs/pbd/xl_research/automation.html 4 pages.

Chayen, Naomi E., "Tackling the bottleneck of protein crystallization in the post-genomic era", TRENDS in Biotechnology, vol. 20, No. 3 (Mar. 2002), 1 page.

Chayen, Naomi E., "The role of oil in macromolecular crystallization", Structure, vol. 5, No. 10 (1997), pp. 1269-1274.

Chayen, Naomi E. et al., Apocrustacyanin A1 from the lobster carotenoprotein α-cruslacyanin: crystallization and initial X-ray analysis involving softer X-rays, Acta Cryst. D56 (2000), pp. 1064-1066.

Chayen, N.E. et al., "Porous Silicon: an Effective Nucleation-inducing Material for Protein Crystallization", J. Mol. Biol., Academic Press, 312 (2001), pp. 591-595.

Chayen, Naomi E. et al., "Protein crystallization for genomics: towards high-throughput optimization techniques", Acta Cryst. D58 (2002), pp. 921-927.

Chayen, N.E. et al., "Trends and Challenges in Experimental Macromolecular Crystallography", Quarterly Review of Biophysics, 29, 3 (1996), pp. 227-278.

Chayen, Naomi E. et al., "Purification, crystallization and initial X-ray analysis of the $C_1$ subunit of the astaxanthin protein, $V_{600}$, of the chondrophore *Velella velella*", Acta Cryst. D55, (1999), pp. 266-268.

Chayen, Naomi E. et al., "Space-grown crystals may prove their worth", Nature 398, 20 (1999), p. 6722.

Cianci, M. et al., "Structure of lobster apocrustacyanin A, using softer X-rays", Acta Cryst. D57 (2001), pp. 1219-1229.

Press Release: "Crystallomics Core", Crystallomics Core at JCSG, http://bioinfo-core.jcsg.org/bio/links/crystallomics.htm (Apr. 18, 2001), 2 pages.

Delucas, Lawrence J. et al., "New High-throughput Crystallization Technology", http://www.hwi.buffalo.edu/ACA/ACA02/abstracts/text/E0014.html (2002), 1 page.

Dong, Jun et al., "Bound-solvent structures for microgravity-, ground control-, gel- and microbatch-grown hen egg-white lysozyme crystals at 1.8 Å resolution", Acta Cryst., D55 (1999), pp. 745-752.

Douglas Instruments Proposal: Large-scale Xn "The use of Microbatch for Large Scale Crystallization Projects", http://douglas.co.uk/proposal.htm (Feb. 22, 2001), 6 pages.

Douglas Instruments Website: Differences—The Major Differences between Oryx 6 and IMPAX 1-5 (Mar. 2001), 1 page.

Douglas Instruments Website: "Harvesting—Harvesting Crystals from Microbatch for Cryocrystallography", Research Report 3 (Oct. 1995), 4 pages.

Douglas Instruments, Impax—IMPAX 1-5 for Crystallization with Microbatch, www.douglas.co.uk.impax.htm (printed on Feb. 19, 2004), 8 pages.

Douglas Instruments Website: "Oryx 6 for Crystallization with Microbatch and Sitting Drop", http://douglas.co.uk/oryx.htm (printed on Feb. 19, 2004), 7 pages.

Eickhoff, Holger et al. Webpage: "An Automated Platform for Miniaturized Protein Crystallization" (2002), Greiner Bio-One (Abstract), 1 page.

Erlandsen, Heidi et al. "Combining structural genomics and enzymology: completing the picture in metabolic pathways and enzyme active sites"(2000), Current Opinion Structural Biology, 10, pp. 719-730.

Fiehn, Hendrik et al., "Microsystem Technology for Pipetting Systems: Parallel Sample Treatment in the Submicroliter Range (25)", Small Talk the microfluidics and microarrays Conference Final Conference Program, Association for Laboratory Automation, (Jul. 8-Dec. 2000), San Diego, California (Abstract), 2 pages.

Gaasterland, Terry, "Feasibility of Structural Genomics and Impact on Computational Biology: Post-Workshop Review", Mathematics and Computer Science Division, Argonne National Laboratory (Jan. 26, 1998), 7 pages.

Website: "General Interest II—Invited Abstracts", printed from http://www.hwl.buffalo.edu/ACA/ACA01/abstracts (Jul. 26, 2001), 2 pages.

Goodwill, Kenneth E., et al., "High-throughput x-ray crystallography for structure-based drug design", DDT vol. 6, No. 15 (Suppl.) (2001), pp. S113-S118.

Website: "A recipe to grow crystals of lysozyme by the gel acupuncture technique: Granada Crystallization Box", http://lec.ugr.es/GranadaCrystBox/GCB (Apr. 11, 2002), 7 pages.

Heinemann, Udo et al., "The Berlin "Protein Structure Factory" Initiative", Scientific Concepts, http://www.rzpd.de/psf/s_concept2.html (Dec. 21, 2001), 16 pages.

Press Release: "High-throughput protein crystallization screening and polymorph screening", (Abstract) http://www.steinbeis-europa.de/db/ircnet_details.php?BEREICH=LIFE&TYP=Offer&BB (May 7, 2001), 2 pages.

Hosfield, David et al., "A fully integrated protein crystallization platform for small-molecule drug discovery" (2003), Journal of Structural Biology, 142, pp. 207-217.

Jing, Hua et al., "New structural motifs on the chymotrypsin fold and their potential roles in complement factor 8", Euro. Mol. Bio. Org., vol. 19, No. 2 (2000), pp. 164-173.

Jing, Hua et al., "Structures of Native and Complexed Complement Factor D: Implications of the Atypicall His57 Conformation and Self-inhibitory Loop in the Regulation of Specific Serine Protease Activity", J. Mol. Biol. 282 (1998), pp. 1061-1081.

Jing, Hua et al., "Structural basis of profactor D activation: from a highly flexible zymogen to a novel self-inhibited serine protease, complement factor D", Euro. Mol. Bio. Org., vol. 18, No. 4 (1999), pp. 804-814.

Press Release: "Joint Center For Structural Genomics Funded to Advance High-Throughput Protein Structure Determination", http://www.sdsc.edu/Press/00/092600.html (Sep. 25, 2000), 3 pages.

Jones, Ronald et al., Fully Automated Preparation of Hanging Drop Protein Crystallization Plates, Abstract from ACA01 meeting, http://www.hwi.buffalo.edu/ACA/ACA01/abstracts/text/W0352.html (2001), 1 page.

Jurisica, I. et al., "High Throughput Macromolecular Crystallization: An Application of Case-Based Reasoning and Data Mining", Methods in Macromolecular Crystallography, IOS Press (2001), pp. 9-14.

Kam, Z. et al., "On the Crystallization of Proteins", J. Mol. Biol. 123 (1978), pp. 539-555.

Koltay, Peter, "A Novel Fixed Volume Dispenser for the Massive Parallel Liquid Handling of Nanoliter Volumes", Abstract for Presentation, http://www.eurolabautomation.org (Oct. 25, 2001), 2 pages.

Kuhn, Peter et al., "The genesis of high-throughput structure-based drug discovery using protein crystallography" (2002), Curr. Opin. Chem. Biol., 5, 704-710.

Lesley, Scott, A. et al., "Structural genomics of the Thermotoga maritima proteome implemented in a high-throughput structure determination pipeline" (2002), Proc. Natl. Acad. Sci., 99, 11664-11669.

Lowe, Jan. et al., "Capital Equipment MRC Laboratory of Molecular Biology" (Nov. 4, 2001), 4 pages.

Luo, Ming "Structural Genomics of C. *elegans*", www.hwi.buffalo.edu/ACA/ACA02/abstracts/text/W0027.html (2002), (Abstract), 1 page.

Luft, Joseph R. et al., "High Throughput Protein Crystallization: Keeping up with the Genomics", Abstract from the presentation given at Gordon Research Conference "Diffraction Methods in Molecular Biology", http://www.imca.aps.anl.gov/-ahoward/luft_ab.html (Jul. 2000), 1 page.

Luft, Joseph R. et al., "The development of high throughput methods for macromolecular microbatch crystallization", Hampton Research—RAMC 1999 Presentation Abstracts (1999), 1 page.

Mochalkin, Igor et al., "High-Throughput Structure Determination in an Informatics Environment", http://www.acceltys.com/webzine (Aug. 1, 2002), 4 pages.

Mueller, Uwe, et al., "Development of a Technology for Automation and Miniaturization of Protein Crystallization", J. Biotech. (2001), 85, pp. 7-14.

Meeting Summary: "NIGMS Protein Structure Initiative Meeting Summary Apr. 24, 1998", http://www.nigms.nih.gov/news/reports/protein_structure.html (Apr. 24, 1998), 12 pages.

Meeting Summary: "NIGMS Structural Genomics Targets Workshop Feb. 11-12, 1999", http://www.nigms.nih.gov/news/meetings/structural_genomics_targets.html, 18 pages.

Nyarsik, Lajos. et al., "High Throughput Screening Station for Automated Protein Crystallization", (Abstract) (Estimated to be around 2002), 1 page.

Page, Rebecca. et al., "Shotgun crystallization strategy for structural genomics; an optimized two-tiered crystallization screen against the Thermotoga maritima proteome"(2003), Acta Cryst., D59, pp. 1028-1037.

Report: Physical Biosciences Division, particularly section "Protein Microcrystallization Robotic System" (1998), pp. 14-17, http://www-nsd.lbl.gov/LBL/-Publications/LDRD/1998/PB/index.html#iaklevic, 17 pages.

Preuss, Paul, "The Crystal Robot", Berkeley Lab Research Review Summer 2000, http://www.lbl.gov/Science-Articles/Research-Review/Magazine/2000/Winter/features (2000), 3 pages.

Report: "Protein Microcrystallization and Structure Determination", http://www.-nsd.lbl.gov/LBL-Publications/LDRD/1999/PBD.html#Stevens (1999), 3 pages.

Press Release: "RAMC 2001-Poster Abstracts", www.hamptonresearch.com/stuff/RAMC01PA.html (2001), 17 pages.

Rupp, Bernard, "High Throughput Protein Crystallization-EMBL Practical Course on Protein Expression, Purification, and Crystallization-Aug. 14-20$^{th}$, 2000", EMBL Outstation Hamburg, Germany, http://www.structure.lini.gov/Xray/tutorial/High_Throughput_EMBL_full.html (2000), 10 pages.

Sanchez, Roberto et al., "Protein structure modeling for structural genomics", *Nature* Structural Biology, Structural Genomics Supplement (Nov. 2000), pp. 986-990.

Santarsiero, Bernard et al., "An approach to rapid protein crystallization using nanodroplets" J. Appl. Cryst., 35 (2002), pp. 278-281.

Santarsiero, Bernard et al., "Protein Micro-Crystallization Robotics System", W0251: Protein Micro-Crystallization Robotics System, (Abstract for ACA99 meeting) http://www.hwi.buffalo.edu/ACA/ACA99/Abstracts/Text/W0251 (1999), 2 pages.

Saridakis, Emmanuel et al., "Improving protein crystal quality by decoupling nucleation and growth in vapor diffusion", *Protein Sci.* 9, (2000), pp. 755-757.

Schuetz, Andreas J. et al., "A Novel nano-pipelting system for the development of high quality BioChip arrays", http://www.tecan.com/la2000_nanppip.pdf (2000), 1 page.

Selby, Thomas L. et al., "Bioinformatics and High-Throughput Protein Production for Structural Genomics" (2002), Gene Cloning and Expression Technologies, pp. 281-304.

Shaw Stewart, Patrick, "Crystallization of a protein by microseeding after establishing its phase diagram", Research Report 1, www.douglas.co.uk/resrep.htm (Aug. 1995), 7 pages.

Shumate, Christopher, "Low-volume (nanoliter) automated pipetting", Am. Biotechnol Lab. (1993), 11, p. 14.

Snell, E.H. et al., "Partial Improvement of Crystal Quality for Microgravity-Grown Apocrustacyanin $C_1$", Acta. Cryst., D53 (1997), pp. 231-239.

Stevens, Raymond C. et al., "Global Efforts in Structural Genomics", Science (Oct. 5, 2001), 294, pp. 89-92.

Stevens, Raymond C. "High-throughput protein crystallization" (Review), Current Opinion in Structural Biology (2000), 10, pp. 558-563.

Stevens, Raymond C., "Design of high-throughput methods of protein production for structural biology", Structure, vol. 8, No. 9, (2000), pp. R177-R185.

Stevens, Raymond C., "Industrializing Structural Biology", Science, vol. 293 (Jul. 20, 2001), pp. 519-522.

Stevens, Raymond C., "The cost and value of three-dimensional protein structure"(2003), Drug Discovery World, 4, pp. 35-48.

Webpage: "High-throughput Technology Publications", http://stevens.scriops.edu/weboage/hisb/htpubs.html (Jan. 2004), 2 pages.

Stevenson, Robert, "The World of Separation Science—Lab Automation '01: A Market Preparing For Transition?" (2001), 2 pages.

S7-Instrumentation—Instrumentation and techniques for crystallization (Oral Presentation), Nancy 2000 XIX European Crystallographic Meeting Aug. 25-31, 2000, pp. 1-3.

Press Release: "The Robot- X-ray Crystallography in Leiden", http://www.chem.Leidemuniv.nl/bfsc/robot.html (Mar. 2, 2002), 2 pages.

Webpage: "The Society for Biomolecular Screening-7th Annual Conference and Exhibition Poster Session 7—Genomics, Proteomics and New Target Discovery", (2001), see #7014-7015, http://www.hwi.buffalo.edu, 5 pages.

Tisone, T.C. et al., "The Role of Non Contact Microfluidics in High Throughput Protein Crystallization", (Abstract W0282 from ACA 2002 Meeting) http://www.hwi.buffalo.edu/ACA/ACA02/abstracts/text/W0282.html, 1 page.

Van Der Woerd, Mark J. et al., "About Small Streams and Shiny Rocks: Macromolecular Crystal Growth in Microfluidics"(Abstract W0210 from ACA 2002 Meeting) http://www.hwi.buffalo.edu/ACA/ACA02/abstracts/text/W0210.html, 1 page.

Van Der Woerd, Mark J., "Lab-on-a-Chip Based Protein Crystallization [P-66]", (Abstract) SmallTalk 2001 Association for Laboratory Automation Final Conference Program. San Diego, CA, (Aug. 27-31, 2001), 2 pages.

Presentation: Van Der Woerd, Mark J. et al., "Lab-on-a-Chip Based Protein Crystallization" (Oct. 25, 2001), 27 pages.

Villasenor, Armando et al., "Fast Drops: A Speedy Approach to Setting Up Protein Crystallization Trials" (Abstract W0309) from ACA 2001 Meeting) http://www.hwi.buffalo.edu/ACA/ACA01/abstracts/text/W0309.html, 1 page.

Weselak, M. et al., "Robotics for Automated Crystal Formation and Analysis"(2003), Methods in Enzymology, 368, pp. 45-76.

Presentation: "Working Group on Biosciences" Chair: Graham Fleming, University of California, Berkeley, http://www.-als.lbl.gov/als.workshops/scidirecthtml/9BioSci/Word_Work_File_L_646 (1998), pp. 175-198.

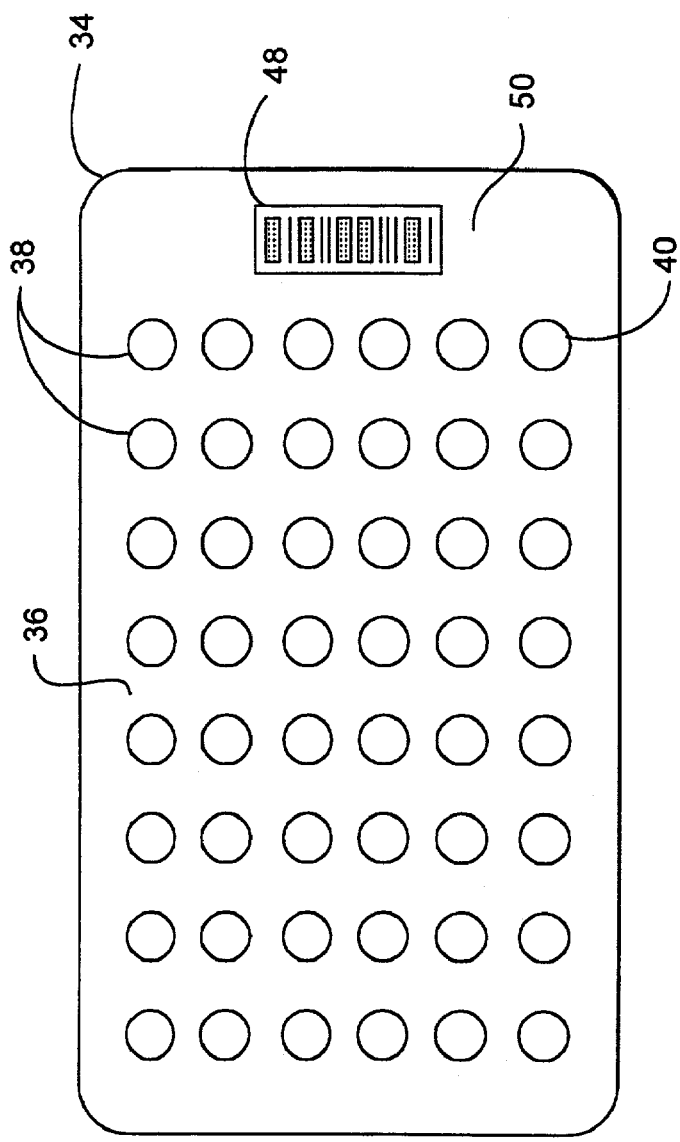
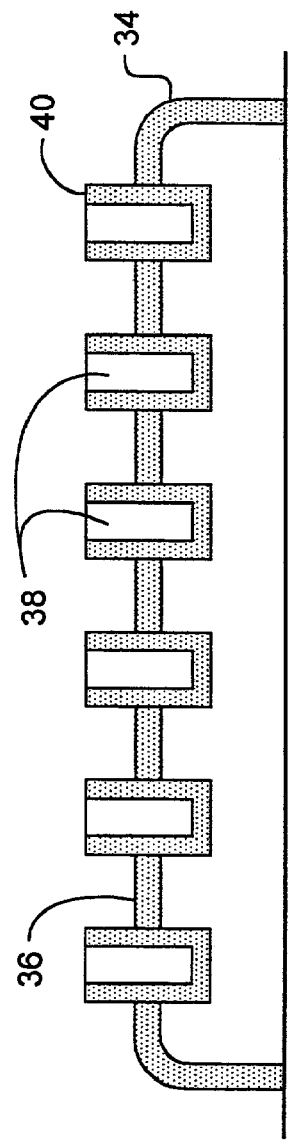
FIG. 3A
FIG. 3B

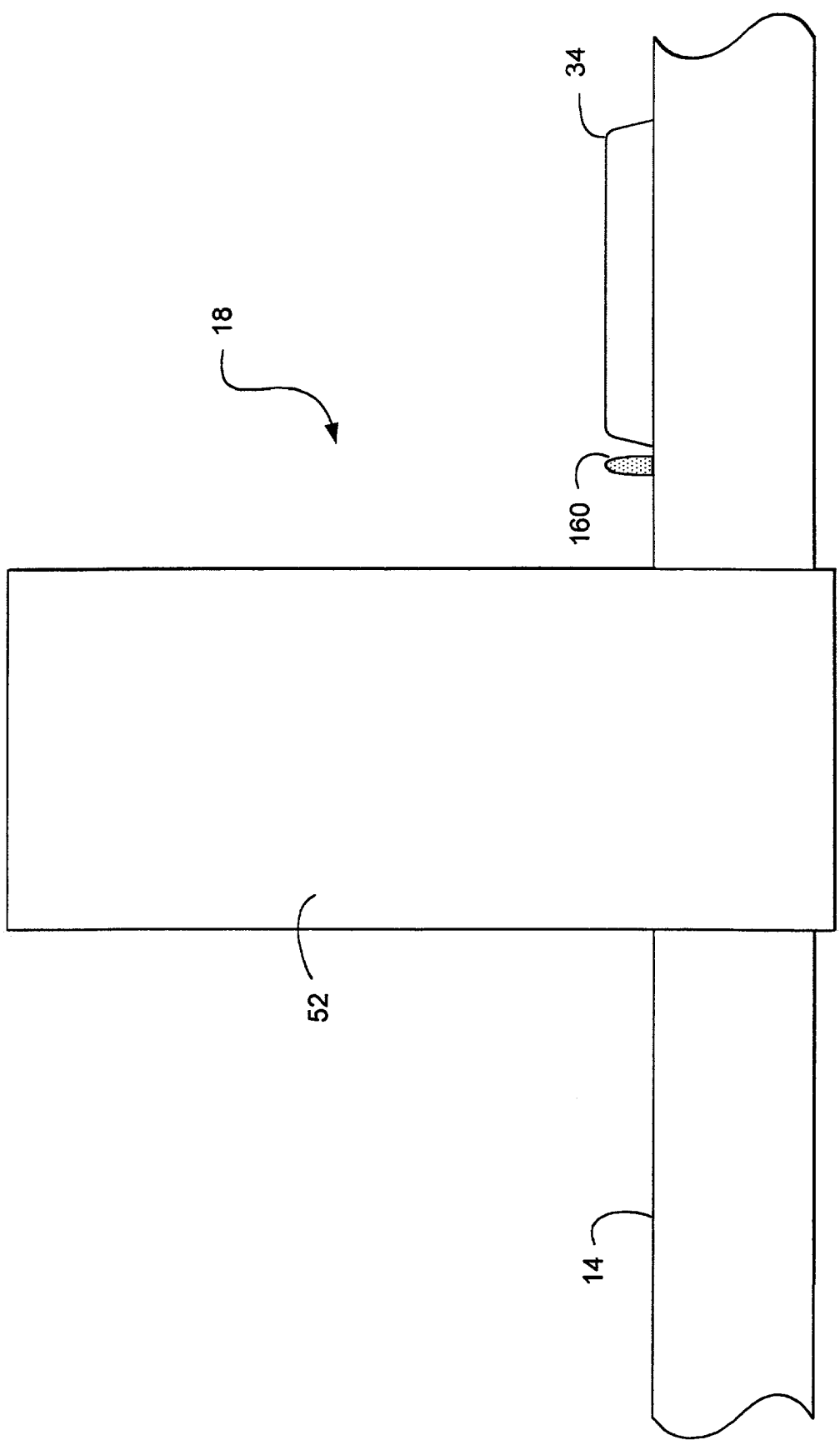

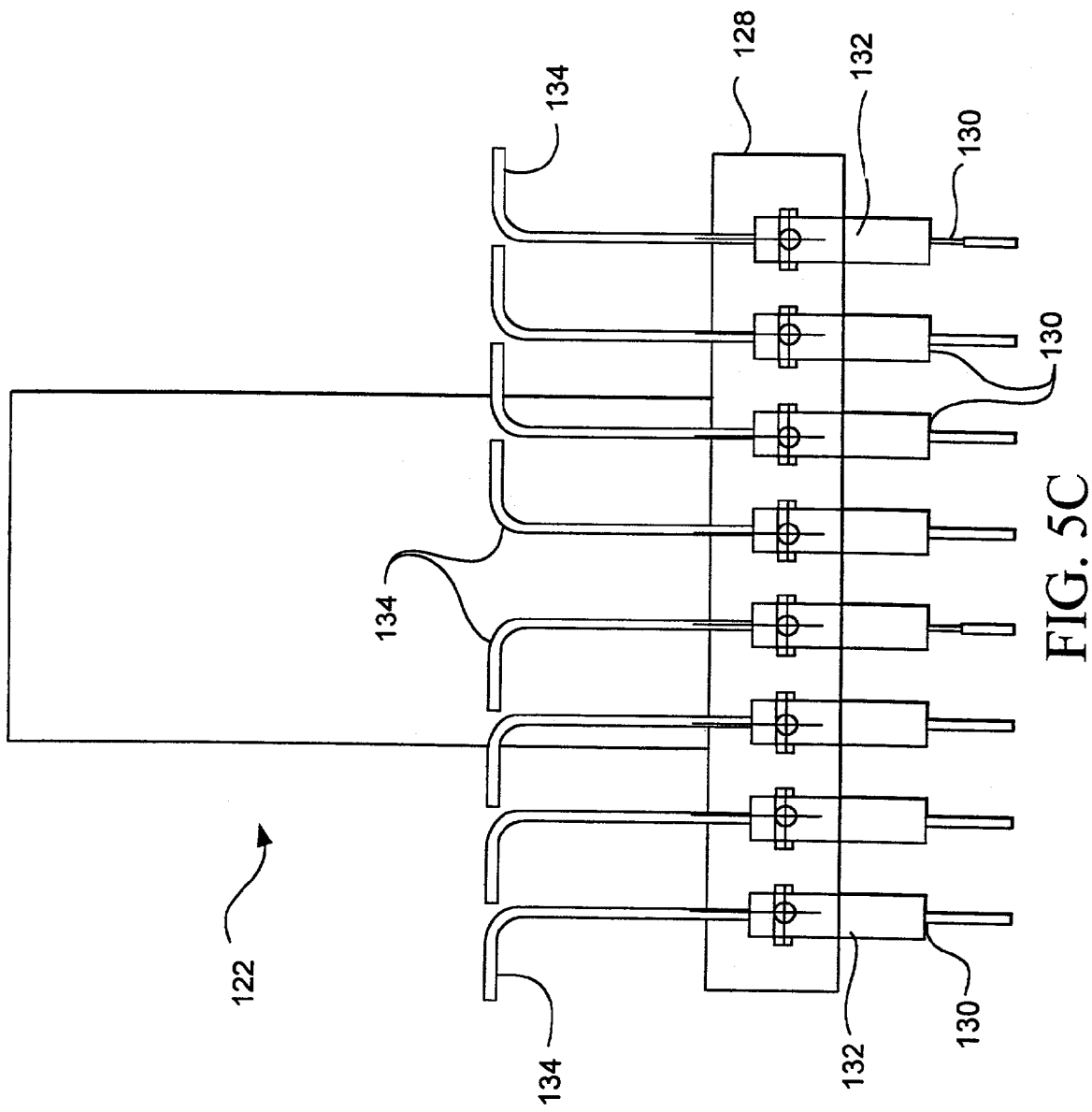

Quik Screen Reagent Formulations

A1. 0.8 M Sodium/Potassium Phosphate pH 5.0
B1. 1.0 M Sodium/Potassium Phosphate pH 5.0
C1. 1.4 M Sodium/Potassium Phosphate pH 5.0
D1. 1.8 M Sodium/Potassium Phosphate pH 5.0
A2. 0.8 M Sodium/Potassium Phosphate pH 5.6
B2. 1.0 M Sodium/Potassium Phosphate pH 5.6
C2. 1.4 M Sodium/Potassium Phosphate pH 5.6
D2. 1.8 M Sodium/Potassium Phosphate pH 5.6
A3. 0.8 M Sodium/Potassium Phosphate pH 6.3
B3. 1.0 M Sodium/Potassium Phosphate pH 6.3
C3. 1.4 M Sodium/Potassium Phosphate pH 6.3
D3. 1.8 M Sodium/Potassium Phosphate pH 6.3
A4. 0.8 M Sodium/Potassium Phosphate pH 6.9
B4. 1.0 M Sodium/Potassium Phosphate pH 6.9
C4. 1.4 M Sodium/Potassium Phosphate pH 6.9
D4. 1.8 M Sodium/Potassium Phosphate pH 6.9
A5. 0.8 M Sodium/Potassium Phosphate pH 7.5
B5. 1.0 M Sodium/Potassium Phosphate pH 7.5
C5. 1.4 M Sodium/Potassium Phosphate pH 7.5
D5. 1.8 M Sodium/Potassium Phosphate pH 7.5
A6. 0.8 M Sodium/Potassium Phosphate pH 8.2
B6. 1.0 M Sodium/Potassium Phosphate pH 8.2
C6. 1.4 M Sodium/Potassium Phosphate pH 8.2
D6. 1.8 M Sodium/Potassium Phosphate pH 8.2

FIG. 9

Detergent Screen 2 Reagent Formulations 1. 10% v/v Pluronic F-68
2. 10% v/v Anapoe 35
3. 10% v/v Anapoe 56
4. 10% v/v Anapoe 58
5. 10% v/v Anapoe X-114
6. 10% v/v Anapoe X-305
7. 10% v/v Anapoe X-405
8. 10% v/v Anapoe 20
9. 10% v/v Anapoe 80
10. 10% v/v Anapoe $C_{10}E_6$
11. 10% v/v Anapoe $C_{10}E_9$
12. 10% v/v Anapoe $C_{12}E_{10}$
13. 10% v/v Anapoe $C_{13}E_6$
14. 10% w/v IPTG
15. 1.5 mM n-Dodecyl-N,N-dimethylglycine
16. 7.0 mM HEGA-10
17. 7.1 mM $C_8E_5$
18. 8.0 mM CHAPS
19. 8.0 mM CHAPSO
20. 11.5 mM C-HEGA 11
21. 39 mM HEGA-9
22. 108 mM C-HEGA 9
23. 109 mM HEGA-8
24. 277 mM C-HEGA-8

Note: [mM] is that of the CMC of the detergent

FIG. 9
(Continued)

Detergent Screen 3 Reagent Formulations 1. 10% w/v BAM
2. 0.006 mM n-Hexadecyl-b-D-maltoside
3. 0.1 mM n-Tetradecyl-b-D-maltoside
4. 0.33 mM n-Tridecyl-b-D-maltoside
5. 0.9 mM Thesit
6. 4.0 mM Zwittergent 3-14
7. 5.9 mM n- Undecyl-b-D-maltoside
8. 9.0 mM n-Decyl-b-D-thiomaltoside
9. 15.0 mM FOS-Choline 12
10. 25 mM n-Decanoylsucrose
11. 29.0 mM I-S-Nonyl-b-D-thioglucoside
12. 32.0 mM n-Nonyl-b-D-thiomaltoside
13. 43.0 mM DDMAB
14. 60.0 mM n-Nonyl-b-D-maltoside
15. 76.0 mM Cymal-4
16. ◇

17. 130 mM FOS-Choline-10
18. 190 mM FOS-Choline-9
19. 250 mM MEGA-9
20. 290 mM I-S-Heptyl-b-D-thioglucoside
21. 1.02 M FOS-Choline-8
22. 1.20 M Cymal-2
23. 3.30 M Zwittergent 3-08
24. 3.40 M Cymal-1

Note: [mM] is that of the CMC of the detergent

FIG. 9
(Continued)

Crystal Screen Reagent Formulations 1. 30% MPD, 0.1 M Na Acetate pH 4.6, 0.02 M Calcium Chloride
2. 0.4 M K, Na Tartrate
3. 0.4 M Ammonium Phosphate
4. 2.0 Ammonium Sulfate, 0.1 M Tris HCl pH 8.5
5. 30% MPD, 0.1 M Na Hepes pH 7.5, 0.2 M Na Citrate
6. 30% PEG 4000, 0.1 M Tris HCl pH 8.5, 0.2 M Mg Chloride
7. 1.4 M Na Acetate, 0.1 M Na Cacodylate pH 6.5
8. 30% 2-Propanol, 0.1 M Na Cacodylate pH 6.5, 0.2 M Na Citrate
9. 30% PEG 4000, 0.1 M Na Citrate pH 5.6, 0.2 Ammonium Acetate
10. 30% PEG 4000. 0.1 M Na Acetate pH 4.6, 0.2 M Ammonium Acetate
11. 1.0 M Ammonium Phosphate, 0.1 M Na Citrate pH 5.6
12. 30% 2-Propanol, 0.1 M Na Hepes pH 7.5, 0.2 M Mg Chloride
13. 30% PEG 400, 0.1 M Tris HCl pH 8.5, 0.2 M Na Citrate
14. 28% PEG 400, 0.1 M Na Hepes pH 7.5, 0.2 M Ca Chloride
15. 30% PEG 8000, 0.1 M Na Cacodylate pH 6.5, 0.2 M Ammonium Sulfate
16. 1.5 M Li Sulfate, 0.1 M Na Hepes pH 7.5
17. 30% PEG 4000, 0.1 M Tris HCl pH 8.5, 0.2 M Li Sulfate
18. 20% PEG 8000, 0.1 M NA Cacodylate pH 6.5, 0.2 M Mg Acetate
19. 30% 2-Propanol, 0.1 M Tris HCl pH 8.5, 0.2 M Ammonium Acetate
20. 25% PEG 4000, 0.1 M Na Acetate pH 4.6, 0.2 M Ammonium Sulfate
21. 30% MPD, 0.1 M Na Cacodylate pH 6.5, 0.2 M Mg Acetate
22. 30% PEG 4000, 0.1 M Tris HCl pH 8.5, 0.2 M Na Acetate
23. 30% PEG 400, 0.1 M Na Hepes pH 7.5, 0.2 M Mg Chloride
24. 20% 2-Propanol, 0.1 M Na Acetate pH 4.6, 0.2 M Ca Chloride FIG. 9
(Continued)

Crystal Screen Reagent Formulations 25. 1.0 M Na Acetate, 0.1 M Imidazole pH 6.5
26. 30% MPD, 0.1 M Na Citrate pH 5.6, 0.2 M Ammonium Acetate
27. 20% 2- Propanol, 0.1 M Na Hepes pH 7.5, 0.2 M Na Citrate
28. 30% PEG 8000, 0.1 M Na Cacodylate pH 6.5, 0.2 M Na Acetate
29. 0.8 M K, Na Tartrate, 0.1 M Na Hepes pH 7.5
30. 30% PEG 8000, 0.2 M Ammonium Sulfate
31. 30% PEG 4000, 0.2 M Ammonium Sulfate
32. 2.0 M Ammonium Sulfate
33. 4.0 M Na Formate
34. 2.0 M Na Formate, 0.1 M Na Acetate pH 4.6
35. 1.6 M Na, K Phosphate, 0.1 M Na Hepes pH 7.5
36. 8% PEG 8000, 0.1 M Tris HCl pH 8.5
37. 8% PEG 4000, 0.1 M Na Acetate pH 4.6
38. 1.4 M Na Citrate, 0.1 M Na Hepes pH 7.5
39. 2% PEG 400, 2.0 M Ammonium Sulfate, 0.1 M Na Hepes pH 7.5
40. 20% 2-Propanol, 20% PEG 4000, 0.1 M Na Citrate pH 5.6
41. 10% 2-Propanol, 20% PEG 4000, 0.1 M Na Hepes pH 7.5
42. 20% PEG 8000, 0.05 M K Phosphate
43. 30% PEG 1500
44. 0.2 M Mg Formate
45. 18% PEG 8000, 0.1 M Na Cacodylate pH 6.5, 0.2 M Zn Acetate
46. 18% PEG 8000, 0.1 M Na Cacodylate pH 6.5, 0.2 M Ca Acetate
47. 2.0 M Ammonium Sulfate, 0.1 M Na Acetate pH 4.6
48. 2.0 M Ammonium Phosphate, 0.1 M Tris HCl pH 8.5

FIG. 9
(Continued)

Grid Screen Ammonium Sulfate Reagent Formulations

A1. 0.1 M Citric Acid pH 4.0, 0.8 M Ammonium Sulfate
B1. 0.1 M Citric Acid pH 4.0, 1.6 M Ammonium Sulfate
C1. 0.1 M Citric Acid pH 4.0, 2.4 M Ammonium Sulfate
D1. 0.1 M Citric Acid pH 4.0, 3.2 M Ammonium Sulfate
A2. 0.1 M Citric Acid pH 5.0, 0.8 M Ammonium Sulfate
B2. 0.1 M Citric Acid pH 5.0, 1.6 M Ammonium Sulfate
C2. 0.1 M Citric Acid pH 5.0, 2.4 M Ammonium Sulfate
D2. 0.1 M Citric Acid pH 5.0, 3.2 M Ammonium Sulfate
A3. 0.1 M MES pH 6.0, 0.8 M Ammonium Sulfate
B3. 0.1 M MES pH 6.0, 1.6 M Ammonium Sulfate
C3. 0.1 M MES pH 6.0, 2.4 M Ammonium Sulfate
D3. 0.1 M MES pH 6.0, 3.2 M Ammonium Sulfate
A4. 0.1 M HEPES pH 7.0, 0.8 M Ammonium Sulfate
B4. 0.1 M HEPES pH 7.0, 1.6 M Ammonium Sulfate
C4. 0.1 M HEPES pH 7.0, 2.4 M Ammonium Sulfate
D4. 0.1 M HEPES pH 7.0, 3.2 M Ammonium Sulfate
A5. 0.1 M Tris pH 8.0, 0.8 M Ammonium Sulfate
B5. 0.1 M Tris pH 8.0, 1.6 M Ammonium Sulfate
C5. 0.1 M Tris pH 8.0, 2.4 M Ammonium Sulfate
D5. 0.1 M Tris pH 8.0, 3.2 M Ammonium Sulfate
A6. 0.1 M Bicine pH 9.0, 0.8 M Ammonium Sulfate
B6. 0.1 M Bicine pH 9.0, 1.6 M Ammonium Sulfate
C6. 0.1 M Bicine pH 9.0, 2.4 M Ammonium Sulfate
D6. 0.1 M Bicine pH 9.0, 3.2 M Ammonium Sulfate FIG. 9
(Continued)

Grid Screen MPD Reagent Formulations

A1. 0.1 M Citric Acid pH 4.0, 10% 2-Methyl-2,4-pentanediol
B1. 0.1 M Citric Acid pH 4.0, 20% 2-Methyl-2,4-pentanediol
C1. 0.1 M Citric Acid pH 4.0, 40% 2-Methyl-2,4-pentanediol
D1. 0.1 M Citric Acid pH 4.0, 65% 2-Methyl-2,4-pentanediol
A2. 0.1 M Sodium Acetate trihydrate pH 5.0, 10% 2-Methyl-2,4-pentanediol
B2. 0.1 M Sodium Acetate trihydrate pH 5.0, 20% 2-Methyl-2,4-pentanediol
C2. 0.1 M Sodium Acetate trihydrate pH 5.0, 40% 2-Methyl-2,4-pentanediol
D2. 0.1 M Sodium Acetate trihydrate pH 5.0, 65% 2-Methyl-2,4-pentanediol
A3. 0.1 M MES pH 6.0, 10% 2-Methyl-2,4-pentanediol
B3. 0.1 M MES pH 6.0, 20% 2-Methyl-2,4-pentanediol
C3. 0.1 M MES pH 6.0, 40% 2-Methyl-2,4-pentanediol
D3. 0.1 M MES pH 6.0, 65% 2-Methyl-2,4-pentanediol
A4. 0.1 M HEPES pH 7.0, 10% 2-Methyl-2,4,pentanediol
B4. 0.1 M HEPES pH 7.0, 20% 2-Methyl-2,4,pentanediol
C4. 0.1 M HEPES pH 7.0, 40% 2-Methyl-2,4,pentanediol
D4. 0.1 M HEPES pH 7.0, 65% 2-Methyl-2,4,pentanediol
A5. 0.1 M Tris pH 8.0, 10% 2-Methyl-2,4-pentanediol
B5. 0.1 M Tris pH 8.0, 20% 2-Methyl-2,4-pentanediol
C5. 0.1 M Tris pH 8.0, 40% 2-Methyl-2,4-pentanediol
D5. 0.1 M Tris pH 8.0, 65% 2-Methyl-2,4-pentanediol
A6. 0.1 M Bicine pH 9.0, 10% 2-Methyl-2,4-pentanediol
B6. 0.1 M Bicine pH 9.0, 20% 2-Methyl-2,4-pentanediol
C6. 0.1 M Bicine pH 9.0, 40% 2-Methyl-2,4-pentanediol
D6. 0.1 M Bicine pH 9.0, 65% 2-Methyl-2,4-pentanediol

FIG. 9
(Continued)

Grid Screen Sodium Chloride Reagent Formulations

A1. 0.1 M Citric Acid pH 4.0, 1.0 M Sodium Chloride
B1. 0.1 M Citric Acid pH 4.0, 2.0 M Sodium Chloride
C1. 0.1 M Citric Acid pH 4.0, 3.0 M Sodium Chloride
D1. 0.1 M Citric Acid pH 4.0, 4.0 M Sodium Chloride
A2. 0.1 M Citric Acid pH 5.0, 1.0 M Sodium Chloride
B2. 0.1 M Citric Acid pH 5.0, 2.0 M Sodium Chloride
C2. 0.1 M Citric Acid pH 5.0, 3.0 M Sodium Chloride
D2. 0.1 M Citric Acid pH 5.0, 4.0 M Sodium Chloride
A3. 0.1 M MES pH 6.0, 1.0 M Sodium Chloride
B3. 0.1 M MES pH 6.0, 2.0 M Sodium Chloride
C3. 0.1 M MES pH 6.0, 3.0 M Sodium Chloride
D3. 0.1 M MES pH 6.0, 4.0 M Sodium Chloride
A4. 0.1 M HEPES pH 7.0, 1.0 M Sodium Chloride
B4. 0.1 M HEPES pH 7.0, 2.0 M Sodium Chloride
C4. 0.1 M HEPES pH 7.0, 3.0 M Sodium Chloride
D4. 0.1 M HEPES pH 7.0, 4.0 M Sodium Chloride
A5. 0.1 M Tris pH 8.0, 1.0 M Sodium Chloride
B5. 0.1 M Tris pH 8.0, 2.0 M Sodium Chloride
C5. 0.1 M Tris pH 8.0, 3.0 M Sodium Chloride
D5. 0.1 M Tris pH 8.0, 4.0 M Sodium Chloride
A6. 0.1 M Bicine pH 9.0, 1.0 M Sodium Chloride
B6. 0.1 M Bicine pH 9.0, 2.0 M Sodium Chloride
C6. 0.1 M Bicine pH 9.0, 3.0 M Sodium Chloride
D6. 0.1 M Bicine pH 9.0, 4.0 M Sodium Chloride FIG. 9
(Continued)

Grid Screen PEG 6000 Reagent Formulations

A1. 0.1 M Citric Acid pH 4.0, 5% Polyethylene Glycol 6000
B1. 0.1 M Citric Acid pH 4.0, 10% Polyethylene Glycol 6000
C1. 0.1 M Citric Acid pH 4.0, 20% Polyethylene Glycol 6000
D1. 0.1 M Citric Acid pH 4.0, 30% Polyethylene Glycol 6000
A2. 0.1 M Citric Acid pH 5.0, 5% Polyethylene Glycol 6000
B2. 0.1 M Citric Acid pH 5.0, 10% Polyethylene Glycol 6000
C2. 0.1 M Citric Acid pH 5.0, 20% Polyethylene Glycol 6000
D2. 0.1 M Citric Acid pH 5.0, 30% Polyethylene Glycol 6000
A3. 0.1 M MES pH 6.0, 5% Polyethylene Glycol 6000
B3. 0.1 M MES pH 6.0, 10% Polyethylene Glycol 6000
C3. 0.1 M MES pH 6.0, 20% Polyethylene Glycol 6000
D3. 0.1 M MES pH 6.0, 30% Polyethylene Glycol 6000
A4. 0.1 M HEPES pH 7.0, 5% Polyethylene Glycol 6000
B4. 0.1 M HEPES pH 7.0, 10% Polyethylene Glycol 6000
C4. 0.1 M HEPES pH 7.0, 20% Polyethylene Glycol 6000
D4. 0.1 M HEPES pH 7.0, 30% Polyethylene Glycol 6000
A5. 0.1 M Tris pH 8.0, 5% Polyethylene Glycol 6000
B5. 0.1 M Tris pH 8.0, 10% Polyethylene Glycol 6000
C5. 0.1 M Tris pH 8.0, 20% Polyethylene Glycol 6000
D5. 0.1 M Tris pH 8.0, 30% Polyethylene Glycol 6000
A6. 0.1 M Bicine pH 9.0, 5% Polyethylene Glycol 6000
B6. 0.1 M Bicine pH 9.0, 10% Polyethylene Glycol 6000
C6. 0.1 M Bicine pH 9.0, 20% Polyethylene Glycol 6000
D6. 0.1 M Bicine pH 9.0, 30% Polyethylene Glycol 6000

FIG. 9
(Continued)

Grid Screen PEG/LiCl Reagent Formulations

A1. 0.1 M Citric Acid pH 4.0, 1.0 M Lithium Chloride
B1. 0.1 M Citric Acid pH 4.0, 10% Polyethylene Glycol 6000, 1.0 M Lithium Chloride
C1. 0.1 M Citric Acid pH 4.0, 20% Polyethylene Glycol 6000, 1.0 M Lithium Chloride
D1. 0.1 M Citric Acid pH 4.0, 30% Polyethylene Glycol 6000, 1.0 M Lithium Chloride
A2. 0.1 M Citric Acid pH 5.0, 1.0 M Lithium Chloride
B2. 0.1 M Citric Acid pH 5.0, 10% Polyethylene Glycol 6000, 1.0 M Lithium Chloride
C2. 0.1 M Citric Acid pH 5.0, 20% Polyethylene Glycol 6000, 1.0 M Lithium Chloride
D2. 0.1 M Citric Acid pH 5.0, 30% Polyethylene Glycol 6000, 1.0 M Lithium Chloride
A3. 0.1 M MES pH 6.0, 1.0 M Lithium Chloride
B3. 0.1 M MES pH 6.0, 10% Polyethylene Glycol 6000, 1.0 M Lithium Chloride
C3. 0.1 M MES pH 6.0, 20% Polyethylene Glycol 6000, 1.0 M Lithium Chloride
D3. 0.1 M MES pH 6.0, 30% Polyethylene Glycol 6000, 1.0 M Lithium Chloride
A4. 0.1 M HEPES pH 7.0, 1.0 M Lithium Chloride
B4. 0.1 M HEPES pH 7.0, 10% Polyethylene Glycol 6000, 1.0 M Lithium Chloride
C4. 0.1 M HEPES pH 7.0, 20% Polyethylene Glycol 6000, 1.0 M Lithium Chloride
D4. 0.1 M HEPES pH 7.0, 30% Polyethylene Glycol 6000, 1.0 M Lithium Chloride
A5. 0.1 M Tris pH 8.0, 1.0 M Lithium Chloride
B5. 0.1 M Tris pH 8.0, 10% Polyethylene Glycol 6000, 1.0 M Lithium Chloride
C5. 0.1 M Tris pH 8.0, 20% Polyethylene Glycol 6000, 1.0 M Lithium Chloride
D5. 0.1 M Tris pH 8.0, 30% Polyethylene Glycol 6000, 1.0 M Lithium Chloride
A6. 0.1 M Bicine pH 9.0, 1.0 M Lithium Chloride
B6. 0.1 M Bicine pH 9.0, 10% Polyethylene Glycol 6000, 1.0 M Lithium Chloride
C6. 0.1 M Bicine pH 9.0, 20% Polyethylene Glycol 6000, 1.0 M Lithium Chloride
D6. 0.1 M Bicine pH 9.0, 30% Polyethylene Glycol 6000, 1.0 M Lithium Chloride

FIG. 9
(Continued)

PEG/Ion Screen Reagent Formulations 1. 0.2 M Sodium Fluoride, 20% PEG 3350
2. 0.2 M Potassium Fluoride, 20% PEG 3350
3. 0.2 M Ammonium Fluoride, 20% PEG 3350
4. 0.2 M Lithium Chloride, 20% PEG 3350
5. 0.2 M Magnesium Chloride, 20% PEG 3350
6. 0.2 M Sodium Chloride, 20% PEG 3350
7. 0.2 M Calcium Chloride, 20% PEG 3350
8. 0.2 M Potassium Chloride, 20% PEG 3350
9. 0.2 M Ammonium Chloride, 20% PEG 3350
10. 0.2 M Sodium Iodide, 20% PEG 3350
11. 0.2 M Potassium Iodide, 20% PEG 3350
12. 0.2 M Ammonium Iodide, 20% PEG 3350
13. 0.2 M Sodium Thiocyanate, 20% PEG 3350
14. 0.2 M Potassium Thiocyanate, 20% PEG 3350
15. 0.2 M Lithium Nitrate, 20% PEG 3350
16. 0.2 M Magnesium Nitrate, 20% PEG 3350
17. 0.2 M Sodium Nitrate, 20% PEG 3350
18. 0.2 M Potassium Nitrate, 20% PEG 3350
19. 0.2 M Ammonium Nitrate, 20% PEG 3350
20. 0.2 M Magnesium Formate, 20% PEG 3350
21. 0.2 M Sodium Formate, 20% PEG 3350
22. 0.2 M Potassium Formate, 20% PEG 3350
23. 0.2 M Ammonium Formate, 20% PEG 3350
24. 0.2 M Lithium Acetate, 20% PEG 3350

FIG. 9
(Continued)

PEG/Ion Screen Reagent Formulations 25. 0.2 M Magnesium Acetate, 20% PEG 3350
26. 0.2 M Zinc Acetate, 20% PEG 3350
27. 0.2 M Sodium Acetate, 20% PEG 3350
28. 0.2 M Calcium Acetate, 20% PEG 3350
29. 0.2 M Potassium Acetate, 20% PEG 3350
30. 0.2 M Ammonium Acetate, 20% PEG 3350
31. 0.2 M Lithium Sulfate, 20% PEG 3350
32. 0.2 M Magnesium Sulfate, 20% PEG 3350
33. 0.2 M Sodium Sulfate, 20% PEG 3350
34. 0.2 M Potassium Sulfate, 20% PEG 3350
35. 0.2 M Ammonium Sulfate, 20% PEG 3350
36. 0.2 M di-Sodium Tartrate, 20% PEG 3350
37. 0.2 M Potassium Sodium Tartrate, 20% PEG 3350
38. 0.2 M di-Ammonium Tartrate, 20% PEG 3350
39. 0.2 M Sodium dihydrogen Phosphate, 20% PEG 3350
40. 0.2 M di-Sodium hydrogen Phosphate, 20% PEG 3350
41. 0.2 M Potassium dihydrogen Phosphate, 20% PEG 3350
42. 0.2 M di-Potassium hydrogen Phosphate, 20% PEG 3350
43. 0.2 M Ammonium dihydrogen Phosphate, 20% PEG 3350
44. 0.2 M di-Ammonium hydrogen Phosphate, 20% PEG 3350
45. 0.2 M tri-Lithium Citrate, 20% PEG 3350
46. 0.2 M tri-Sodium Citrate, 20% PEG 3350
47. 0.2 M tri-Potassium Citrate, 20% PEG 3350
48. 0.2 M di-Ammonium hydrogen Citrate, 20% PEG 3350

FIG. 9
(Continued)

MembFac Reagent Formulations

1. 12% MPD, 0.1 M Na Acetate pH 4.6, 0.1 M Na Chloride
2. 12% PEG 4000, 0.1 M Na Acetate pH 4.6, 0.1 M Zn Acetate
3. 10% PEG 4000, 0.1 M Na Acetate pH 4.6, 0.2 M Ammonium Sulfate
4. 12% Isopropanol, 0.1 M Na Acetate pH 4.6, 0.1 M Na Chloride
5. 12% PEG 4000, 0.1 M Na Acetate pH 4.6
6. 1.0 M Ammonium Sulfate, 0.1 M Na Acetate pH 4.6
7. 1.0 M Mg Sulfate, 0.1 M Na Acetate pH 4.6
8. 18% PEG 400, 0.1 M Na Acetate pH 4.6, 0.1 M Mg Chloride
9. 1.0 M Ammonium Phosphate, 0.1 M Na Acetate pH 4.6, 0.1 M Li Sulfate
10. 12% PEG 6000, 0.1 M Na Acetate pH 4.6, 0.1 M Na Chloride
11. 12% PEG 6000, 0.1 M Na Acetate pH 4.6, 0.1 M Mg Chloride
12. 18% PEG 400, 0.1 M Na Citrate pH 5.6, 0.1 M Na Chloride
13. 12% PEG 4000, 0.1 M Na Citrate pH 5.6, 0.1 M Li Sulfate
14. 10% Isopropanol, 0.1 M Na Citrate pH 5.6, 0.1 M Na Citrate
15. 12% MPD, 0.1 M Na Citrate pH 5.6, 0.1 M Na Chloride
16. 1.0 M Mg Sulfate, 0.1 M Na Citrate pH 5.6
17. 12% PEG 4000, 0.1 M Na Citrate pH 5.6, 0.1 M Na Chloride
18. 12% PEG 6000, 0.1 M Na Citrate pH 5.6, 0.1 M Li Sulfate
19. 4% MPD, 0.1 M Na Citrate pH 5.6, 0.1 M Mg Chloride
20. 0.1 M Na Chloride, 0.1 M Na Citrate pH 5.6
21. 4% PEG 400, 0.1 M Na Citrate pH 5.6, 0.1 M Li Sulfate
22. 1.0 M Ammonium Sulfate, 0.1 M ADA pH 6.5
23. 12% PEG 4000 2% Isopropanol, 0.1 M ADA pH 6.5, 0.1 M Li Sulfate
24. 1.0 M di-Ammonium Phosphate, 0.1 M ADA pH 6.5

FIG. 9
(Continued)

MembFac Reagent Formulations 25. 12% PEG 6000, 0.1 M ADA pH 6.5, 0.1 M Mg Chloride
26. 12% MPD, 0.1 M ADA pH 6.5
27. 1.0 M Mg Sulfate, 0.1 M ADA pH 6.5, 0.1 M Li Sulfate
28. 4% PEG 400, 0.1 M ADA pH 6.5, 0.3 M Li Sulfate
29. 1.0 M di-Na/K Phosphate, 0.1 Na Hepes pH 7.5, 0.1 M Ammonium Sulfate
30. 10% PEG 4000, 0.1 Na Hepes pH 7.5, 0.1 M Na Chloride
31. 18% PEG 400, 0.1 Na Hepes pH 7.5, 0.1 M Mg Chloride
32. 1.0 M K/Na Tartrate, 0.1 Na Hepes pH 7.5
33. 18% PEG 400, 0.1 Na Hepes pH 7.5, 0.1 M Ammonium Sulfate
34. 10% PEG 4000, 0.1 Na Hepes pH 7.5, 0.1 M Ammonium Sulfate
35. 12% MPD, 0.1 Na Hepes pH 7.5, 0.1 M Na Citrate
36. 1.0 M Na Citrate, 0.1 Na Hepes pH 7.5
37. 4% PEG 400, 0.1 Na Hepes pH 7.5, 0.6 M Mg Sulfate
38. 4% MPD, 0.1 Na Hepes pH 7.5, 0.6 M Mg Sulfate
39. 0.1 M K/Na Tartrate, 0.1 Na Hepes pH 7.5, 0.1 M Li Sulfate
40. 12% MPD, 0.1 M Tris HCl pH 8.5, 0.1 M Li Sulfate
41. 0.5 M di-Na/K Phosphate, 0.1 Tris HCl pH 8.5, 0.1 Ammonium Phosphate
42. 0.1 M Na Acetate, 0.1 Tris HCl pH 8.5
43. 0.1 M Na Chloride, 0.1 Tris HCl pH 8.5
44. 12% PEG 6000, 0.1 Tris HCl pH 8.5, 0.1 M Ammonium Phosphate
45. 0.4 M Mg Sulfate, 0.1 Tris HCl pH 8.5, 0.1 M K/Na Tartrate
46. 0.2 M Li Sulfate, 0.1 Tris HCl pH 8.5
47. 0.5 M Ammonium Sulfate, 0.1 Tris HCl pH 8.5
48. 5% PEG 400, 0.1 Tris HCl pH 8.5, 0.1 M Na Citrate FIG. 9
(Continued)

Detergent Screen 1 Reagent Formulations 1. 0.08 mM $C_{12}E_9$
2. 0.11 mM $C_{12}E_8$
3. 0.17 mM n-Dodecyl-b-D-maltoside
4. 0.20 mM Sucrose monolaurate
5. 0.56 mM CYMAL-6
6. 0.90 mM TRITON X-100
7. 1.00 mM CTAB
8. 1.40 mM Deoxy BigChap
9. 1.80 mM n-Decyl-b-D-maltoside
10. 2.00 mM LDAO
11. 2.40 mM CYMAL-5
12. 4.00 mM ZWITTERGENT 3-12
13. 6.50 mM Nonyl-b-D-glucoside
14. 9.00 mM l-S-octyl-b-D-thioglucoside
15. 10.4 mM DDAO
16. 19.5 mM HECAMEG
17. 24.4 mM n-Octanoylsucrose
18. 30.0 mM Heptyl-b-D-thioglucoside
19. 24.5 mM n-Octyl-b-D-glucoside
20. 34.5 mM CYMAL-3
21. 35.0 mM C-HEGA-10
22. 40.0 mM ZWITTERGENT 3-10
23. 79.0 mM MEGA-8
24. 250.0 mM n-Hexyl-b-D-glucoside

Note: [mM] is that of the CMC of the detergent

FIG. 9
(Continued)

Crystal Screen Cryo Reagent Formulations 1. 30% MPD, 0.1 M Na Acetate pH 4.6, 0.02 M Calcium Chloride
2. 0.26 M K, Na Tartrate, 35% Glycerol
3. 0.26 M Ammonium Phosphate, 35% Glycerol
4. 1.5 M Ammonium Sulfate, 0.075 M Tris HCl pH 8.5, 25% Glycerol
5. 30% MPD, 0.1 M Sodium Hepes pH 7.5, 0.2 M sodium Citrate
6. 24% PEG 4000, 0.08 M Tris HCl pH 8.5, 0.16 M Magnesium Chloride, 20% Glycerol
7. 0.98 M Sodium Acetate, 0.07 M Na Cacodylate pH 6.5, 30% Glycerol
8. 21% iso-Propanol, 0.07 M Na Cacodylate pH 6.5, 0.14 M Sodium Citrate, 30% Glycerol
9. 25.5% PEG 4000, 0.085 M Na Citrate pH 5.6, 0.17 M Ammonium Acetate, 15% Glycerol
10. 25.5% PEG 4000, 0.085 M Na Acetate pH 4.6, 0.17 M Ammonium Acetate, 15% Glycerol
11. 0.7 M Ammonium Phosphate, 0.07 M Na Citrate pH 5.6, 30% Glycerol
12. 27% iso-Propanol, 0.09 M Na Hepes pH 7.5, 0,18 M Magnesium Chloride, 10% Glycerol
13. 30% PEG 400, 0.1 M Tris HCl pH 8.5, 0.2 M Sodium Citrate
14. 26.6% PEG 400, 0.095 M Na Hepes pH 7.5, 0.19 M Calcium Chloride, 5% Glycerol
15. 25.5% PEG 8000, 0.085 M Na Cacodylate pH 6.5, 0.17 M Ammonium Sulfate, 15 % Glycerol
16. 1.125 M Lithium Sulfate, 0.075 M Na Hepes pH 7.5, 25% Glycerol
17. 25.5% PEG 4000, 0.085 M Tris HCl pH 8.5, 0.17 M Lithium Sulfate, 15% Glycerol
18. 16% PEG 8000, 0.08 M Na Cacodylate pH 6.5, 0.16 M Magnesium Acetate, 20% Glycerol
19. 24% iso-Propanol, 0.08 M Tris HCl pH 8.5, 0.16 M Ammonium Acetate, 20% Glycerol
20. 20% PEG 4000, 0.08 M Na Acetate pH 4.6, 0.16 M Ammonium Sulfate, 20% Glycerol
21. 30% MPD, 0.1 M Na Cacodylate pH 6.5, 0.2 M Magnesium Acetate
22. 25.5% PEG 4000, 0.085 M Tris HCl pH 8.5, 0.17 M Sodium Acetate, 15% Glycerol
23. 30% PEG 400, 0.1 M NA Hepes pH 7.5, 0.2 M Magnesium Chloride
24. 14% iso-Propanol, 0.07 M Na Acetate pH 4.6, 0.14 M Calcium Chloride, 30% Glycerol FIG. 9
(Continued)

Crystal Screen Cryo Reagent Formulations

25. 0.7 M Sodium Acetate, 0.07 M Imidazole pH 6.5, 30% Glycerol

26. 30% MPD, 0.1 M Na Citrate pH 5.6, 0.2 M Ammonium Acetate

27. 14% iso-Propanol, 0.07 M NA Hepes pH 7.5, 0.14 M Sodium Citrate, 30% Glycerol

28. 25.5% PEG 8000, 0.085 M Na Cacodylate pH 6.5, 0.17 M Sodium Acetate, 15% Glycerol

29. 0.52 M K, Na Tartrate, 0.065 M Na Hepes pH 7.5, 35% Glycerol

30. 25.5% PEG 8000, 0.17 M Ammonium Sulfate, 15% Glycerol

31. 25.5% PEG 4000, 0.17 M Ammonium Sulfate, 15% Glycerol

32. 1.5 M Ammonium Sulfate, 25% Glycerol

33. 3.6 M Sodium Formate, 10% Glycerol

34. 1.4 M Sodium Formate, 0.07 M Na Acetate pH 4.6, 30% Glycerol

35. 1.2 M Na, K Phosphate, 0.075 M Na Hepes pH 7.5, 25% Glycerol

36. 5.2% PEG 8000, 0.065 M Tris Hcl pH 8.5, 35% Glycerol

37. 5.6% PEG 4000, 0.07 M Na Acetate pH 4.6, 30% Glycerol

38. 1.26 M Sodium Citrate, 0.09 M Na Hepes pH 7.5, 10% Glycerol

39. 1.7% PEG 400, 0.085 M Na Hepes pH 7.5, 1.7 M Ammonium Sulfate, 15% Glycerol

40. 19% iso-Propanol, 0.095 M Na Citrate pH 5.6, 19% PEG 4000, 5% Glycerol

41. 8.5% iso-Propanol, 0.085 M Na Hepes pH 7.5, 17% PEG 4000, 15% Glycerol

42. 16% PEG 8000, 0.04 M Potassium Phosphate, 20% Glycerol

43. 24% PEG 1500, 20% Glycerol

44. 0.1 M Magnesium Formate, 50% Glycerol

45. 14.4% PEG 8000, 0.08 M Na Cacodylate pH 6.5, 0.16 M Zinc Acetate, 20% Glycerol

46. 14.4% PEG 8000, 0.08 M Na Cacodylate pH 6.5, 0.16 M Calcium Acetate, 20% Glycerol

47. 1.6 M Ammonium Sulfate, 0.08 M Na Acetate pH 4.6, 20% Glycerol

48. 1.6 M Ammonium Phosphate, 0.08 M Tris HCl pH 8.5, 20% Glycerol

FIG. 9
(Continued)

Low Ionic Strength Screen Reagent Formulations

Buffers

1. 0.05 M Potassium chloride pH 2.0
2. 0.05 M Citric acid pH 3.0
3. 0.05 M Citric acid pH 3.5
4. 0.05 M Citric acid pH 4.0
5. 0.05 M Citric acid pH 4.5
6. 0.05 M Citric acid pH 5.0
7. 0.05 M Citric acid pH 5.5
8. 0.05 M MES pH 6.0
9. 0.05 M Bis-Tris pH 6.5
10. 0.05 M Imidazole pH 7.0
11. 0.05 M Hepes pH 7.5
12. 0.05 M Tris pH 8.0
13. 0.05 M Tris pH 8.5
14. 0.05 M Glycine pH 9.0
15. 0.05 M Glycine pH 9.5
16. 0.05 M Glycine pH 10.0
17. 0.05 M di-sodium hydrogen phosphate pH 11.0
18. 0.05 M di-sodium hydrogen phosphate pH 12.0

Precipitants

A. 4% w/v Polyethylene glycol 3350
B. 8% w/v Polyethylene glycol 3350
C. 12% w/v Polyethylene glycol 3350
D. 16% w/v Polyethylene glycol 3350
E. 20% w/v Polyethylene glycol 3350
F. 24% w/v Polyethylene glycol 3350

Dehydrant

24% w/v Polyethylene glycol 3350

FIG. 9
(Continued)

| Concentration of CaCl₂ (mM) \ pH | 4.1 | 4.3 | 4.5 | 4.7 | 4.9 | 5.1 |
|---|---|---|---|---|---|---|
| 12.5 | 1.6 A<br>8.3 B<br>75.0 C<br>19.3 D<br>145.8 W | 1.6 A<br>8.3 B<br>75.0 C<br>16.9 D<br>148.3 W | 1.6 A<br>8.3 B<br>75.0 C<br>14.1 D<br>151.0 W | 1.6 A<br>8.3 B<br>75.0 C<br>11.4 D<br>153.7 W | 1.6 A<br>8.3 B<br>75.0 C<br>8.7 D<br>156.4 W | 1.6 A<br>8.3 B<br>75.0 C<br>6.3 D<br>158.8 W |
| 17.5 | 2.2 A<br>8.3 B<br>75.0 C<br>19.3 D<br>145.2 W | 2.2 A<br>8.3 B<br>75.0 C<br>16.9 D<br>147.6 W | 2.2 A<br>8.3 B<br>75.0 C<br>14.1 D<br>150.3 W | 2.2 A<br>8.3 B<br>75.0 C<br>11.4 D<br>153.1 W | 2.2 A<br>8.3 B<br>75.0 C<br>8.7 D<br>155.8 W | 2.2 A<br>8.3 B<br>75.0 C<br>6.3 D<br>158.2 W |
| 22.5 | 2.8 A<br>8.3 B<br>75.0 C<br>19.3 D<br>144.6 W | 2.8 A<br>8.3 B<br>75.0 C<br>16.9 D<br>147.0 W | 2.8 A<br>8.3 B<br>75.0 C<br>14.1 D<br>149.7 W | 2.8 A<br>8.3 B<br>75.0 C<br>11.4 D<br>152.5 W | 2.8 A<br>8.3 B<br>75.0 C<br>8.7 D<br>155.2 W | 2.8 A<br>8.3 B<br>75.0 C<br>6.3 D<br>157.6 W |
| 27.5 | 3.4 A<br>8.3 B<br>75.0 C<br>19.3 D<br>143.9 W | 3.4 A<br>8.3 B<br>75.0 C<br>16.9 D<br>146.4 W | 3.4 A<br>8.3 B<br>75.0 C<br>14.1 D<br>149.1 W | 3.4 A<br>8.3 B<br>75.0 C<br>11.4 D<br>151.9 W | 3.4 A<br>8.3 B<br>75.0 C<br>8.7 D<br>154.5 W | 3.4 A<br>8.3 B<br>75.0 C<br>6.3 D<br>157.0 W |

FIG. 11

A = volume of 2M CaCl2
B = volume of 3M NaOAc
C = volume of 100% MPD
D = volume of 1M HCl
W = volume of 100% water

Crystal Screen 2 Reagent Formulations 1. 10% PEG 6000, 2.0 M Na chloride
2. 0.5 M NaCl, 0.01 M CTAB, 0.01 M Mg chloride
3. 25% Ethylene glycol
4. 35% Dioxane
5. 5% Isopropanol, 2.0 M Ammonium sulfate
6. 1.0 M Imidazole pH 7.0
7. 10% PEG 1000, 10% PEG 8000
8. 10% Ethanol, 1.5 M Na chloride
9. 2.0 M Na chloride, 0.1 M Na acetate pH 4.6
10. 30% MPD, 0.1 M Na Acetate pH 4.6, 0.2 M NaCl
11. 1.0 M 1,6 Hexanediol, 0.1 M Na Acetate pH 4.6, 0.01 M Co chloride
12. 30% PEG 400, 0.1 M Na acetate pH 4.6, 0.1 M Cd chloride
13. 30% PEG MME 2000, 0.1 M Na Acetate pH 4.6, 0.2 M Ammonium sulfate
14. 2.0 M Ammonium sulfate, 0.1 M Na Citrate pH 5.6, 0.2 M K/Na Tartrate
15. 1.0 M Li sulfate, 0.1 M Na Citrate pH 5.6, 0.5 M Ammonium sulfate
16. 2% Polyethyleneimine, 0.1 M Na Citrate pH 5.6, 0.5 M NA chloride
17. 35% tert-butanol, 0.1 M Na citrate pH 5.6
18. 10% Jeffamine M-600, 0.1 M Na citrate pH 5.6, 0.01 M Ferric chloride
19. 2.5 M 1,6 Hexanediol, 0.1 M Na citrate pH 5.6
20. 1.6 M Mg sulfate, 0.1 M MES pH 6.5
21. 2.0 M Na chloride, 0.1 M MES pH 6.5, 0.2 M Na/K Phosphate
22. 12% PEG 20,000, 0.1 M MES pH 6.5
23. 10% Dioxane, 0.1 M MES pH 6.5, 1.6 M Ammonium sulfate
24. 30% Jeffamine M-600, 0.1 M MES pH 6.5, 0.05 M Cs chloride

FIG. 11
(Continued)

Crystal Screen 2 Reagent Formulations 25. 1.8 M Ammonium sulfate, 0.1 M MES pH 6.5, 0.01 M Co chloride
26. 30% PEG MME 5000, 0.1 M MES pH 6.5, 0.2 M Ammonium sulfate
27. 25% PEG MME 550, 0.1 M MES pH 6.5, 0.01 M Zn sulfate
28. 1.6 M Sodium citrate pH 6.5
29. 30% MPD, 0.1 M Hepes pH 7.5, 0.5 M Ammonium sulfate
30. 10% PEG 6000, 0.1 M Hepes pH 7.5, 5% MPD
31. 20% Jeffamine M-600, 0.1 M Hepes pH 7.5
32. 1.6 M Ammonium sulfate, 0.1 M Hepes pH 7.5, 0.1 M Na chloride
33. 2.0 M Ammonium formate, 0.1 M Hepes pH 7.5
34. 1.0 M Na acetate, 0.1 M Hepes pH 7.5, 0.05 M Cd sulfate
35. 70% MPD, 0.1 M Hepes pH 7.5
36. 4.3 M Na chloride, 0.1 M Hepes pH 7.5
37. 10% PEG 8000, 0.1 M Hepes pH 7.5, 8% Ethylene glycol
38. 20% PEG 10,000, 0.1 M Hepes pH 7.5
39. 3.4 M 1,6 Hexanediol, 0.1 M Tris pH 8.5, 0.2 M Mg chloride
40. 25% tert-butanol, 0.1 M Tris pH 8.5, 0.1 M Ca chloride
41. 1.0 M Li sulfate, 0.1 M Tris pH 8.5, 0.01 M Ni chloride
42. 12% Glycerol, 0.1 M Tris pH 8.5, 1.5 M Ammonium sulfate
43. 50% MPD, 0.1 M Tris pH 8.5, 0.2 M Ammonium phosphate
44. 20% Ethanol, 0.1 M Tris pH 8.5
45. 20% PEG MME 2000, 0.1 M Tris pH 8.5, 0.01 M Ni chloride
46. 30% PEG MME 550, 0.1 M Bicine pH 9.0, 0.1 M Na chloride
47. 2.0 M Mg chloride, 0.1 M Bicine pH 9.0
48. 10% PEG 20,000, 0.1 M Bicine pH 9.0, 2% Dioxane FIG. 11
(Continued)

METHOD FOR PERFORMING SUBMICROLITER CRYSTALLIZATION EXPERIMENTS WITH HIGH EXPERIMENT TO EXPERIMENT PRECISION

CROSS-REFERENCE TO RELATED APPLICATIONS

This application is a Continuation of U.S. application Ser. No. 09/851,397, filed May 7, 2001, now U.S. Pat. No. 6,630,006 which is Continuation-in-Part of U.S. application Ser. No. 09/336,134, filed June 18, 1999, now U.S. Pat. No. 6,296,673, which is incorporated herein by reference.

BACKGROUND OF THE INVENTION

1. Field of the Invention

The present invention relates to methods and apparatuses for crystallizing molecules and, more particularly, to methods and apparatuses for automating the crystallization of molecules, particularly macromolecules such as proteins.

2. Description of Related Art

Fast progress in the area of genomics has provided explosively growing databases of information on genes of human and other organisms by mapping, sequencing and analyzing their genomes. Many genes that may be critical for identifying people predisposed to certain diseases such as cancer have been discovered and their biological functions have been assessed in vitro and/or in vivo. Recently, a new area of genomics. functional genomics, has been developed, which involves a genome wide analysis of gene function by using information and reagents from the genomic analysis and expressing the genes in various organisms such as yeast. Functional genomics has generated important information regarding the expression pattern of genes by using high throughput screening techniques such as DNA oligonucleotide chips for specific genes or high density microarrays. An understanding of the network of interactions between a protein expressed by a target gene and other macromolecules in the cell is also being expanded at an unprecedented rate by using efficient screening methods such as the yeast hybrid systems.

One of the ultimate goals of these genome projects is the development of efficacious therapeutics against proteins expressed by disease genes. Among various methods of drug discovery and development, structure-based drug development has become one of the most important approaches, thanks to rapidly advancing computation techniques. It is well recognized that understanding of the detailed three-dimensional structure of a protein not only assists in rational drug design and development in the laboratory but also provides a well-defined target in high throughput drug screening by using computer-aided docking analysis.

Solving high resolution structures of protein in a high throughput fashion presents a major bottleneck in such a chain of genomics and drug development. High resolution structures of proteins are solved by X-ray crystallography, and more recently by using multi-dimensional NMR spectroscopy on high-field NMR machines for smaller proteins or peptides.

Various methods for X-ray crystallography have been developed, including the free interface diffusion method (Salemme, F. R. (1972) Arch. Biochem. Biophys. 151: 533–539), vapor diffusion in the hanging or sitting drop method (McPherson, A. (1982) Preparation and Analysis of Protein Crystals, John Wiley and Son, New York, pp 82–127), and liquid dialysis (Bailey, K. (1940) Nature 145:934–935).

Presently, the hanging drop method is the most commonly used method for growing macromolecular crystals from solution, especially for protein crystals. Generally, a droplet containing a protein solution is spotted on a cover slip and suspended in a sealed chamber which contains a reservoir with a higher concentration of precipitating agent. Over time, the solution in the droplet equilibrates with the reservoir by diffusing water vapor from the droplet, thereby slowly increasing the concentration of the protein and precipitating agent within the droplet, which in turn results in precipitation or crystallization of the protein.

The process of growing crystals with high diffraction quality is time-consuming and involves trial-and-error experimentations on multiple solution variables such as pH, temperature, ionic strength, and specific concentrations of salts, organic additives, and detergents. In addition, the amount of highly purified protein is usually limited, multi-dimensional trials on these solution conditions is unrealistic, labor-intensive and costly.

A few automated crystallization systems have been developed based on the hanging drop methods, for example Cox, M. J. and Weber, P. C. (1987) J. Appl. Cryst. 20:366; and Ward, K. B. et al. (1988) J. Crystal Growth 90:325–339. A need exists for improved automated crystallization systems for proteins and other macromolecules.

SUMMARY OF THE INVENTION

The present invention relates to a method for performing array microcrystallizations to determine suitable crystallization conditions for a molecule. The molecule may be a molecule for which an x-ray crystal structure is needed. Determining high-resolution structures of molecules by a high-throughput method such as the one of the present invention can be used to accelerate drug development. The molecule to be crystalized may also be a molecule for which a crystalline form of the molecule is needed. For example, it may be desirable to create a crystalline form of a molecule or to identify new crystalline forms of a molecule. In some instances, particular crystalline forms of a molecule may have more bioactive, dissolve faster, decompose less readily, and/or be easier to purify, The molecule is preferably a macromolecule such as a protein but may also be other types of macromolecules. The molecule preferably has a molecular weight of at least 500 Daltons, more preferably at least 1000 Daltons, although smaller molecular weight molecules may also be crystallized.

In one embodiment, the method comprises: forming an array of microcrystallizations, each microcrystallization including a drop containing a molecule to be crystallized and a mother liquor solution whose composition varies within the array, the drop having a volume of less than 1 $\mu$L; storing the array of microcrystallizations under conditions suitable for molecule crystals to form in the drops in the array; and detecting molecule crystal formation in the drops.

In one variation, the method comprises: forming an array of microcrystallizations, each microcrystallization comprising a well including a mother liquor solution whose composition varies within the array, and drop region including a drop containing the molecule to be crystallized, the drop having a volume of less than 1 $\mu$L; storing the array of microcrystallizations under conditions suitable for molecule crystals to form in the drops in the array; and detecting molecule crystal formation in the drops.

In another variation, the method comprises: forming an array of microcrystallizations, each microcrystallization comprising a well including a mother liquor solution whose composition varies within the array, and a coverslip including a drop containing the molecule to be crystallized, the drop having a volume of less than 1 $\mu$L; storing the array of microcrystallizations under conditions suitable for molecule crystals to form in the drops in the array; and detecting molecule crystal formation in the drops.

In yet another variation, the method comprises: forming an array of microcrystallizations, each microcrystallization comprising a well including a mother liquor solution whose composition varies within the array, and sitting drop region including a drop containing the molecule to be crystallized, the drop having a volume of less than 1 $\mu$L; storing the array of microcrystallizations under conditions suitable for molecule crystals to form in the drops in the array; and detecting molecule crystal formation in the drops.

According to any of the above methods, the volume of the drop containing the molecule to be crystallized is less than about 1 $\mu$L, preferably less than about 750 nL, more preferably less than about 500 $\mu$L, and most preferably less than about 250 nL. In one variation, the drop volume is between 1 nL and 1000 nL, preferably between 1 nL–750 nL, more preferably between 1 nL–500 nL, more preferably between 1 nL–250 nL, and most preferably between 10 nL–250 nL.

The present invention also relates to plates for performing array microcrystallizations to determine suitable crystallization conditions for a molecule. According to one embodiment, the plate comprises an array of at least 36 wells for holding a mother liquor solution, each well having a reservoir volume of less than about 500 $\mu$L, preferably less than about 400 $\mu$L, more preferably less than about 300 $\mu$L and optionally less than about 250 $\mu$L. Ranges of well volumes that may be used include, but are not limited to 25 $\mu$L–500 $\mu$L and 25 $\mu$L–300 $\mu$L. In one variation, the plate is designed to perform a hanging drop crystallization. In another variation, the plate is designed to perform a sitting drop crystallization and includes a mother liquor well as well as an adjacent sitting drop well.

The present invention also relates to various apparatuses for forming submicroliter drops used in an array microcrystallization to determine suitable crystallization conditions for a molecule.

In one embodiment, the apparatus comprises:

a platform on which a multiwell plate is positionable;

a mother liquor drop station capable of removing mother liquor from a plurality of wells of the multiwell plate and delivering submicroliter volumes of mother liquor to drop regions on the multiwell plate within a volume range of less than about 25 nL; and a molecule drop station capable of delivering submicroliter volumes of a solution containing a molecule to be crystallized to the drop regions within a volume range of less than about 25 nL.

In another embodiment the apparatus is designed for preparing submicroliter hanging drops on cover slips used in an array microcrystallization, the apparatus comprising:

a platform on which a multiwell plate is positionable;

a cover slip station on which a plurality of coverslips are positionable;

a mother liquor drop station capable of removing mother liquor from a plurality of wells of the multiwell plate and delivering submicroliter volumes of mother liquor to the plurality of coverslips within a volume range of less than about 25 nL; and a molecule drop station capable of delivering submicroliter volumes of a solution containing a molecule to be crystallized to the plurality of coverslips within a volume range of less than about 25 nL.

In yet another embodiment the apparatus is designed for preparing submicroliter sitting drops used in an array microcrystallization, the apparatus comprising:

a platform on which a multiwell plate is positionable;

a mother liquor drop station capable of removing mother liquor from a plurality of wells of the multiwell plate and delivering submicroliter volumes of mother liquor to drop regions on the multiwell plate within a volume range of less than about 25 nL; and a molecule drop station capable of delivering submicroliter volumes of a solution containing a molecule to be crystallized to the drop regions within a volume range of less than about 25 nL.

According to any of the above embodiments, the mother liquor drop station and the molecule drop station are each capable of delivering submicroliter volumes within a volume range of less than about 20 nL, more preferably less than 15 nL, and most preferably less than 10 nL.

Also according to any of the above embodiments, a sensor may be included in the apparatus for preparing submicroliter drops which is detects whether mother liquor drops and/or molecule drops have been formed.

The mother liquor drop station and the molecule drop station are preferably each independently capable of delivering submicroliter volumes to at least four coverslips at a time, more preferably at least eight coverslips at a time.

The present invention also relates to methods for forming submicroliter drops for use in an array microcrystallization to determine suitable crystallization conditions for a molecule. According to one embodiment, the method includes: removing mother liquor from a plurality of wells of a multiwell plate; delivering submicroliter volumes of the mother liquor to drop regions of the multiwell plate within a volume range of less than about 25 nL; and delivering submicroliter volumes of a solution containing a molecule to be crystallized to the drop regions of the multiwell plate within a volume range of less than about 25 nL; wherein a total volume of the submicroliter volumes delivered to each drop region is less than 1 $\mu$L.

According to another embodiment, the method is for a hanging drop crystallization and includes: taking a plurality of coverslips; removing mother liquor from a plurality of wells of a multiwell plate; delivering submicroliter volumes of the mother liquor to the plurality of coverslips within a volume range of less than about 25 nL; and delivering submicroliter volumes of a solution containing a molecule to be crystallized to the plurality of coverslips within a volume range of less than about 25 nL; wherein a total volume of the submicroliter volumes delivered to each coverslip is less than 1 $\mu$L.

According to another embodiment, the method is for a sitting drop crystallization and includes: removing mother liquor from a plurality of wells of a multiwell plate; delivering submicroliter volumes of the mother liquor to sitting drop regions of the multiwell plate within a volume range of less than about 25 nL; and delivering submicroliter volumes of a solution containing a molecule to be crystallized to the sitting drop regions within a volume range of less than about 25 nL; wherein a total volume of the submicroliter volumes delivered to each sitting drop region is less than 1 $\mu$L.

According to any of the above method embodiments, the total volume of the submicroliter volumes delivered is preferably less than about 750 nL, more preferably less than about 500 nL, and most preferably less than about 250 nL. It is noted that the drop volumes may be as small as 380 pL. The volumes delivered preferably range between 1 nL–750 nL, more preferably between 1 nL–500 nL. more preferably between 1 nL–250 nL, and most preferably between 10 nL–250 nL.

According to any of the above apparatus and method embodiments, the precision of the volumes delivered is preferably less than about 25 nL, more preferably less than 20 nL, more preferably less than 15 nL, and most preferably less than 10 nL. The precision of the volumes delivered may also be between 380 pL and 25 nL, more preferably between 380pL and 20 nL. more preferably between 380pL and 15 nL, and most preferably between 380 pL and 10 nL.

BRIEF DESCRIPTION OF THE FIGURES

FIG. 3A illustrates a top view of a multiwell plate which may be used to perform a hanging drop array microcrystallization.

FIG. 3B is a sideview of the multiwell plate illustrated in FIG. 3A.

FIGS. 4A–4J illustrate the various stations which can be included in a mother liquor delivery system.

FIG. 4A is a sideview of a plate loading station looking across a plate track positioned adjacent to the plate loading station.

FIG. 4B is a sideview of a plate loading station looking along the longitudinal axis of the plate track.

FIG. 4C is a sideview of a bar code reading station for reading a bar code included on a multiwell plate.

FIG. 4D is a sideview of a sealing medium station for applying a sealing medium to an upper edge of wells defined in a multiwell plate.

FIG. 4E is a sideview of a plate cover removal station for removing a plate cover from a multiwell plate.

FIG. 4F is a topview of a mother liquor delivery station.

FIG. 4G is a topview of a delivery block for delivery of a mother liquor into multiwell plates.

FIG. 4H is a cross section of a delivery block for delivery of a mother liquor into a multiwell plates.

FIG. 4I is a sideview of a mother liquor source storage bank.

FIG. 4J is a sideview of a syringe pump for delivering a mother liquor from a mother liquor source to a fluid injector.

FIGS. 5A–5E illustrate the various stations which can be included in a drop formation system.

FIG. 5A is a top view of a drop formation station.

FIG. 5B is a sideview of the drop formation station.

FIG. 5C is a sideview of a pipette holder.

FIG. 5D is a sideview of a well cover holder.

FIG. 5E is a sideview of a well cover magazine for storing well covers to be positioned over the wells in a multiwell plate.

FIG. 6A illustrates a drop formation station in the rest position.

FIG. 6B illustrate the drop formation station with a multiwell plate has been moved into position for drop formation and a pipette holder is moved into position over the wash basin.

FIG. 6C illustrates the pipette holder moved into position over a column of wells in the multiwell plate.

FIG. 6D illustrates the pipette holder moved into position over the well cover holder.

FIG. 6E illustrates the pipette holder returned to its rest position and a protein delivery pipette moved into position over a well cover.

FIG. 6F illustrates the protein delivery pipette moved into its rest position and the cover holder inverted and moved into position over the column of wells on the multiwell plate.

FIG. 6G illustrates hanging drops suspended from well covers over the wells of a plate.

FIG. 6H illustrates the cover holder moved into position over a well cover storage component.

FIG. 6I illustrates the cover holder returned to its rest position.

FIG. 7A illustrates a drop formation station in the rest position.

FIG. 7B illustrate the drop formation station with a multiwell plate adapted to perform a sitting drop array microcrystallization in position for drop formation and a pipette holder moved into position over the wash basin.

FIG. 7C illustrates the pipette holder moved into position over a column of wells in the multiwell plate.

FIG. 7D illustrates pipettes in the pipette holder aligned with the well regions of wells in a column of the plate.

FIG. 7E illustrates pipettes in the pipette holder aligned with the sitting drop regions of wells in a column of the plate.

FIG. 7F illustrates the protein delivery pipette moved into position over the sitting drop region of a well in the column of wells.

FIG. 7G illustrates a sitting drop formed in the sitting drop region of a well.

FIG. 9 illustrates the composition of 480 mother liquor solutions for a preferred coarse screen.

FIG. 11 lists the mother liquor compositions for 24 mother liquors used in the fine screen stage of a crystallization trial.

DETAILED DESCRIPTION

Figure 1:
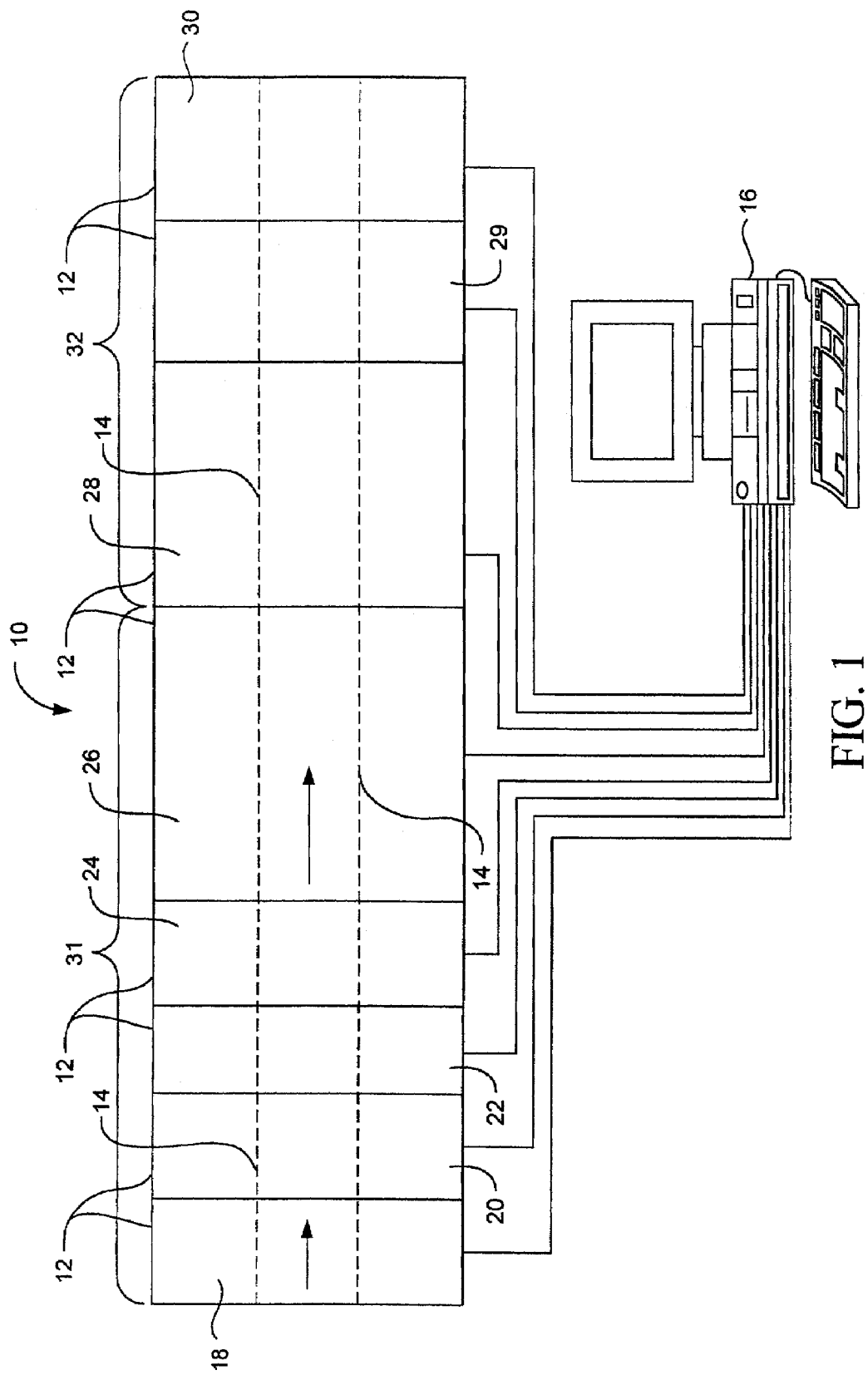
FIG. 1 is a block diagram of a crystallization system according to the present invention.

The present invention relates to a method for performing array microcrystallizations to determine suitable crystallization conditions for a molecule. The molecule is preferably a macromolecule, such as a protein. Other types of molecules and macromolecules may also be crystallized according to the present invention. The molecule preferably has a molecular weight of at least 500 Daltons, more preferably at least 1000 Daltons, although it is noted that the invention can be applied to molecules with lower molecular weights.

The method involves forming an array of microcrystallizations where each microcrystallization includes a drop containing a molecule to be crystallized and a mother liquor solution whose composition varies within the array, the drop having a volume of less than 1 µL. The array of microcrystallizations are stored under conditions suitable for molecule crystals to form in the drops in the array. Molecule crystal formation is then detected in the drops. As will be described herein, this method can be employed in any crystallization method involving drops, including, but not limited to hanging drop crystallization methods and sitting drop crystallization methods. Example sitting drop crystallization methods are provided in U.S. Pat. No. 5,096,676 (McPherson et al.) and U.S. Pat. No. 5,419,278 (Carter).

An important feature of the present invention is the utilization of small drop volumes. For example, the volume of the drop containing the molecule to be crystallized is less than about 1 µL, preferably less than about 750 nL, more preferably less than about 500 nL, and most preferably less than about 250 nL. In one variation, the drop volume is between 1 nL and 1000 nL, preferably between 1 nL–750 nL, more preferably between 1 nL–500 nL, more preferably between 1 nL–250 nL, and most preferably between 10 nL–250 nL.

Applicants believe that the rate of crystallization is dependent on the drop volume where crystals form faster when smaller drop volumes are used. As a result, crystals can be formed more rapidly by using the smaller drop volumes used in the present invention. This significantly increases the through-put rate of the method for determining crystallization conditions.

Without being bound by theory, it is believed that smaller drops will equilibrate faster than larger drops and that this causes crystals to form more rapidly. The rate of equilibration is believed to be related to a relationship between the rate of drop evaporation and drop volume. Meanwhile, the rate of drop evaporation is dependent on drop surface area. The surface area of a drop does not decrease linearly with the drop's volume. As a result, a larger drop having twenty times the volume of a smaller drop (e.g., 1 µL vs. 50 nL) will have significantly less than twenty times the surface area of the smaller drop. By reducing drop volume, one is able to improve the relationship between the rate of drop evaporation (surface area dependent) and drop volume, thereby accelerating equilibration and crystal formation.

A further advantage of the present invention is that smaller drop volumes allow fewer molecules to be used to perform each crystallization trial. As a result, a greater number of crystallization trials can be performed using the same amount of molecule. This is of great significance when it is difficult to obtain the molecule to be crystallized and when a large number of crystallization trials are needed in order to successfully crystallize the molecule.

It is frequently difficult to produce and purify the molecule being crystallized. In the case of protein crystallization, it can require one to two weeks of lab work to produce and purify enough protein to perform 48 crystallization trials using drops greater than 1 µL in size. By reducing the drop volume and hence the amount of molecule used per crystallization trial, it becomes feasible to significantly increase the number of crystallization trials that can be performed. As a result, it becomes feasible to take a more combinatorial, shotgun approach to molecule crystallization trials since the pressure to conserve molecule usage is reduced. By contrast, prior to the present invention's utilization of sub microliter drop volumes, a need existed to minimize the number of trials that were performed at one time due to a shortage of available molecule.

By reducing the drop volume, the number of microcrystallizations that can be performed in the array is increased. The number of microcrystallizations in the array is typically greater than 48, preferably greater than 96, more preferably greater than 144. most preferably greater than 192. It is noted that the number of microcrystallizations in the array can also exceed 288 or 384. For example, an apparatus for preparing arrays which include 480 microcrystallizations is described herein.

Increasing the number of microcrystallizations that can be performed in the array also allows a greater number of different stock solutions to be used to form the mother liquor solutions used in the array. For example, forming the array of microcrystallizations can include using greater than 48 stock solutions to form the mother liquor solutions used in the array. Optionally, greater than 96, more preferably greater than 144, most preferably greater than 192 different stock solutions may be used. It is noted that the number of stock solutions can also exceed 288 or 384. For example, an apparatus described herein uses 480 different stock solutions.

Smaller volumes of mother liquor may also be used in the wells. The volume of mother liquor used in the wells is preferably less than about 500 µL, preferably less than about 400 µL, more preferably less than about 300 µL and optionally less than about 250 µL. Ranges of mother liquor volumes that may be used include, but are not limited to 25 µL–500 µL and 25 µL–300 µL. In this regard, forming the array of microcrystallizations may include forming the microcrystallizations in a plate including a plurality of wells each having a volume less than about 500 µL, preferably less than about 400 µL, more preferably less than about 300 µL.

The use of small volumes of mother liquor allows the wells in multiwell plates to be made smaller, thereby allowing more wells to be positioned on a multiwell plate per unit area. For example, the 48 well plates having a well volume less than about 500 µL has approximately the same footprint as 24 well plates typically used to perform protein crystallization. Further reduction of the mother liquor volumes may be employed in order to further reduce plate sizes.

By utilizing small drop volumes, a significantly greater number of crystallization trials can be performed using the same amount of molecule. As a result, it is feasible to perform a greater number of crystallization trials, which in turn allows the mother liquor solution to be more widely varied in its composition. This allows the mother liquor solution to be formed of 1, 2, 3, 4, 5, 6 or more components which are varied within the array.

Also according to this method, the array of microcrystallizations is formed of one or more multiwell plates. Each plate preferably has at least 24 wells, more preferably at least 36 wells, and most preferably at least 48 wells. By utilizing less mother liquor, smaller wells can be used which allows the same size plate to contain more wells.

Also according to this method, detecting crystal formation can include characterizing the crystal formed (needle, cube, etc.), the size of the crystal, and the quality of the crystal's structure. Characterization of the crystal can be performed manually, or by taking images of the drops and analyzing those images for the structure of crystals contained within those drops.

As noted elsewhere, an objective of the present invention is to provide a high throughput methodology for testing crystallization conditions. By reducing crystallization volumes, the present invention allows one to perform many more crystallization experiments using the same amount of protein. However, when one performs many more crystallization experiments, it then becomes necessary to screen these many more crystallization experiments for crystals.

Figure 12A:
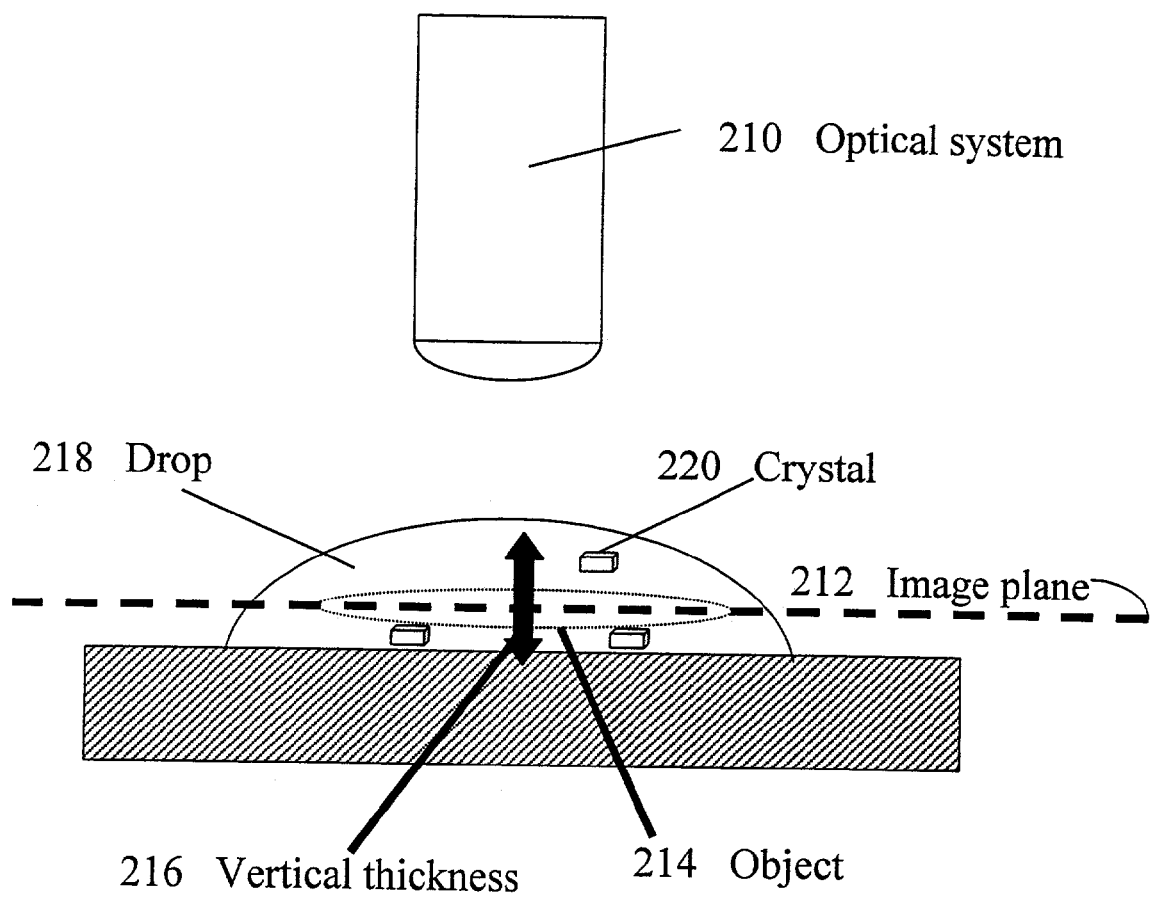
FIG. 12A illustrates an optical system for screening crystallization experiments for crystals.

FIG. 12A illustrates an optical system 210 for screening crystallization experiments for crystals. As illustrated, the optical system 210 has an image plane 212. Objects 214 which are transected by the image plane 212 are in focus. Objects outside the image plane 212 are not in focus. Depending on the depth of field of the optics used, objects outside the image plane can be seen, but with decreased resolution. Ultimately, the depth of field that can be imaged is dependent on the nuerical aperture of the optical system.

The positioning of the image plane 212 is dependent upon the focal length of the optics used in the optical system and the positioning of the optical system 210 relative to the object 214 to be imaged. Focusing the optical system 210 causes the image plane 212 to move vertically toward or away from the optical system 210.

FIG. 12A illustrates a crystallization experiment where the crystallization volume employed (in this case a drop) is larger than those used in the present invention. As illustrated, when larger drop volumes are employed, the vertical thickness 216 of the drop 218 is such that crystals 220 can be present in the drop and outside of the image plane 212 of optical system 210. As a result, it is necessary to adjust the focus of the optical system 210. This causes the image plane 212 to move vertically across the vertical thickness 216 of the drop 218 so that the entire drop can be screened for crystals.

Figure 12B:
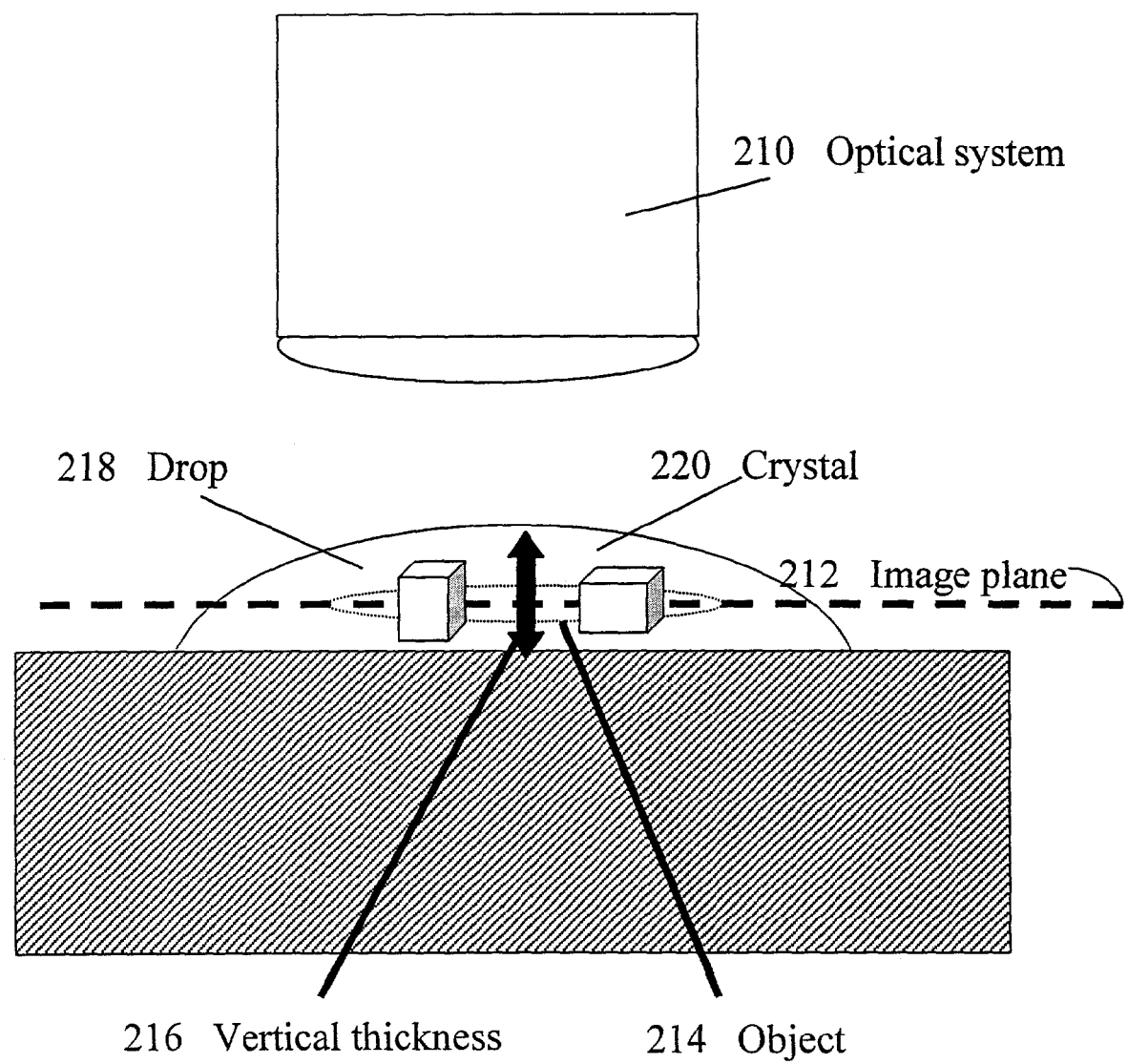
FIG. 12B illustrates an optical system for screening small drop volume crystallization experiments for crystals.

An advantageous feature of performing crystallizations using small drop volumes according to the present invention is that the need to focus the optical system in order to screen for crystals within the drop is eliminated. As illustrated in FIG. 12B, when one images a drop having a small drop volume, the vertical thickness 216 of the drop 218 is sufficiently small that a crystal, if present, will transect the focal plane 212 of the optical system if the focal plane is positioned within the drop, preferably around the middle of the drop. This is shown experimentally herein with regard to FIGS. 10A–10D. As a result, it is unnecessary to adjust the focus the optical system in order scan a drop for crystals. As a result, a single image of a drop can be taken in order to evaluate whether crystals are present in the drop.

As noted above, by reducing drop volumes, the present invention allows one to perform many more crystallization experiments using the same amount of protein. At the same time, the reduced drop volumes of the present invention also allows one to screen crystallization experiments for crystals more rapidly by eliminating the need to adjust the focus of an optical system used to image the crystallization experiments.

The method can also include identifying the compositions of those mother liquor solutions in which crystals were detected and performing additional crystallization trials where the formulation of the mother liquor solutions in which crystals were detected is further varied.

FIG. 1 illustrates a crystallization system 10 for performing a crystallization trial. The crystallization system 10 can be divided into various stations 12 described below. During operation of the crystallization system 10, multiwell plates are positioned on a plate track 14. A transport assembly (not shown) moves the multiwell plates along the plate track 14 to the various stations 12.

The crystallization system 10 also includes a processing unit 16 in electrical communication with the various stations 12. Suitable processing units 16 for use with the crystallization system 10 include, but are not limited to, PCs and computer workstations. The processing unit 16 includes process control logic for controlling the operation of each station and the transport assembly. An operator can use one or more user interfaces to interact with, disengage and/or to alter the process control logic. Suitable user interfaces include, but are not limited to computer monitors, keyboards, mouses, and trackballs.

During operation of the crystallization system 10, the transport assembly moves a multiwell plate past the stations 12 which each perform a particular function. For instance, the crystallization system 10 includes a plate loading station 18 where multiwell plates are sequentially loaded onto the plate track 14. The crystallization system 10 also includes a bar code reading station 20 where a bar code on the multiwell plates can be read. The crystallization system 10 further includes a sealing medium station 22. The sealing medium station 22 can be used to apply a sealing medium to the multiwell plates. Specifically, the sealing medium can be applied to the upper edge of liquid receiving wells defined in each multiwell plate. The sealing medium serves to form a seal between the upper edges of each well and a well cover, commonly referred to as a coverslip, which is positioned over each well at a later station of the crystallization system 10. The crystallization system 10 also includes a plate cover removal station 24 where plate covers 44 are delivered to or removed from the multiwell plates.

The crystallization system 10 also includes a mother liquor delivery station 26 where mother liquors are delivered into the wells defined in the multiwell plates. Different mother liquors can be delivered into different wells or the same mother liquor can be delivered into more than one well. Further, mother liquor can be delivered into a portion of the wells on a single multiwell plate so the remaining wells are empty.

The crystallization system 10 also includes a drop formation station 28 where mother liquors from the various wells are used to form one or more drops on a plurality of coverslips that will be placed over the wells. The drop formation station 28 also adds a solution containing the molecule to be crystallized to the coverslips. Once drops containing mother liquor and the molecule to be crystallized are formed on the coverslips, the coverslips are positioned over each well such that the one or more drops hang from the coverslip into the well. These drops are called hanging drops.

It is noted that the drop formation station can be readily adapted to form sitting drops in a sitting drop regions of a multiwell plate by delivering mother liquors from the various wells and the solution containing the molecule to be crystallized to the sitting drop regions.

The crystallization system 10 also includes a plate cover delivery station 29 where plate covers 44 can be positioned on each multiwell plate. The multiwell plate can then by transported to a plate unloading station 30 where the multiwell plates can be removed from the plate track 14 and stored.

Although the crystallization system 10 illustrated in FIG. 1 has the various stations 12 positioned around a single plate track 14, it is noted that the various stations 12 can be divided into one or more sub-systems, each optionally having its own track. It is further noted that many of the stations 12 may optionally be included or excluded from the crystallization system 10. Further, the stations 12 can be positioned in a sequence other than the sequence illustrated in FIG. 1. For instance, the plate cover removal station 24 can be positioned before the bar code reading station 20. Additionally, several of the described functions can be carried out at a single station. For instance, a plate cover delivery station 29 can be formed integrally with the drop formation station 28 or the plate unloading station 30.

The above stations 12 can be included in a single system or can each be included in different independent sub-systems. For instance, the tray loading station, bar code reading station 20, sealing medium station 22 and mother liquor delivery station 26 can be included in a single mother liquor delivery system 31 while the drop formation station 28 and the plate unloading station 30 can be included in an independent drop formation system 32. Additionally, the functions associated with a particular station need not be carried out during operation of the crystallization system 10. For instance, the mother liquors can be delivered into the wells of a multiwell plate by an external apparatus before the multiwell plate enters the crystallization system 10. In such an instance, when a multiwell plate already containing mother liquor reaches the mother liquor delivery station 26, the mother liquor delivery station 26 can be operated to not deliver mother liquors into the wells.

After a microcrystallization array has been prepared by processing a multiwell plate through a crystallization system 10 such as the one illustrated in FIG. 1, drops in the microcrystallization array can be observed for the formation of crystals. When crystals are formed in a drop of a particular well, the quality of crystals within the drop can be graded for various characteristics such as shape, size or time for crystal formation. When the mother liquors used in each well are different, the crystal grades can be compared to determine which mother liquor was associated with the most desirable crystals. Accordingly, each well serves as a different crystallization experiment which produces results which can be compared with the results of other crystallization experiments.

Figure 2:
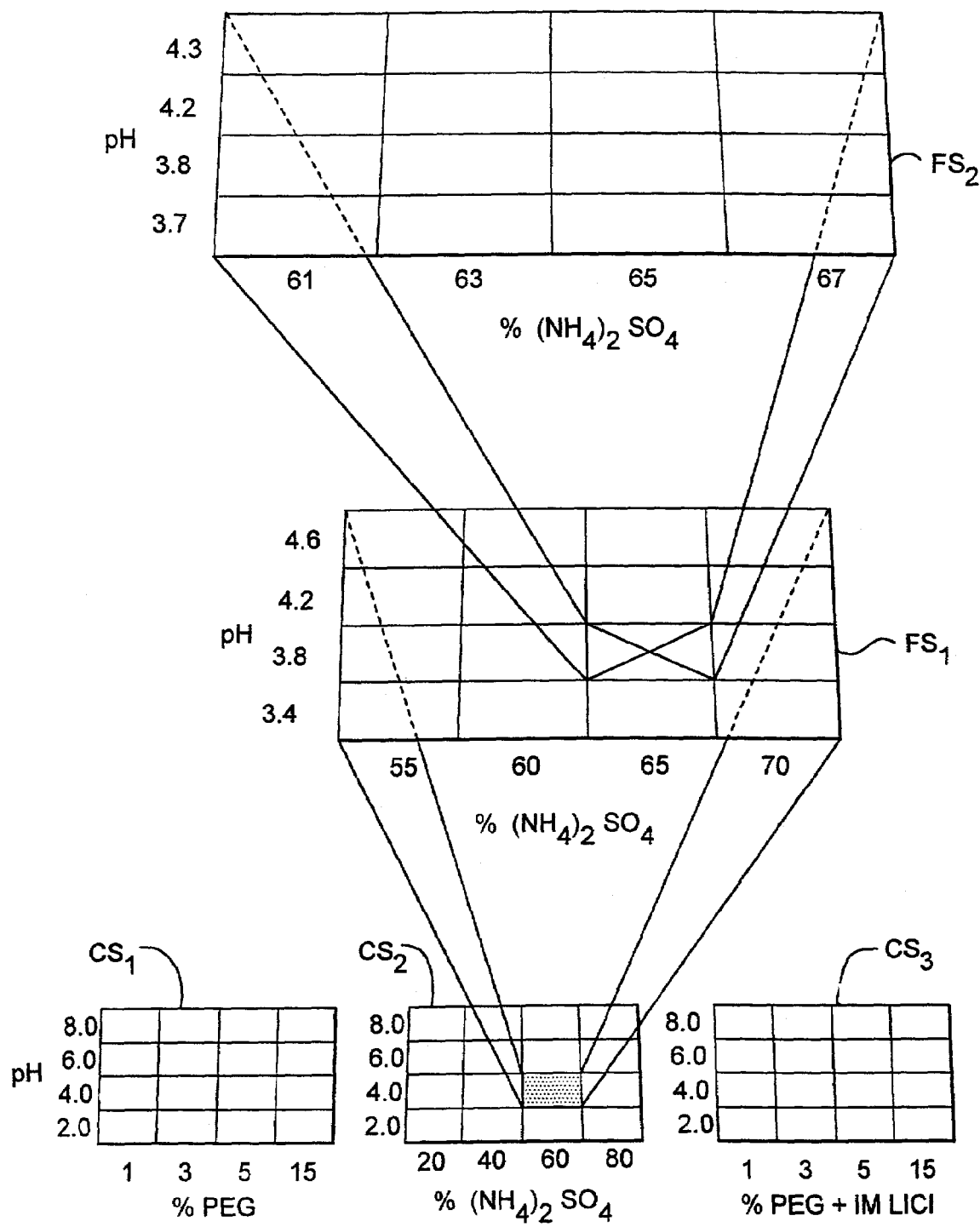
FIG. 2 illustrates a method for using the crystallization system of FIG. 1 to perform a protein crystallization trial.

A crystallization trial includes comparing the results of several crystallization experiments in order to optimize the composition of the mother liquor used for crystallization of a particular molecule. FIG. 2 illustrates a technique for performing a crystallization trial. A coarse screen is performed at an initial stage of the trial. In FIG. 2, the crystallization experiments associated with the coarse screen are illustrated as a plurality of boxes set out in three different arrays which are labeled $CS_1$, $CS_2$ and $CS_3$. In each array two variables of the mother liquor composition are incrementally varied as shown along the x and y axis associated with each array. For instance, in $CS_1$ several crystallization experiments are performed where the pH is varied from 2–8 in intervals of 2 and the % $(NH_4)_2SO_4$ is varied from 20–80 in intervals of 20.

The crystallization experiments in the coarse screen are analyzed to select one or more crystallization experiments which yield the best crystals or, if no crystals form, the best crystal-like precipitate. A coarse screen experiment selected as producing a promising crystal or crystal-like precipitate is illustrated as a black box in FIG. 2. Fine screens are then performed for the crystallization experiments selected through the course screen.

A fine screen crystallization experiment is performed by designing a crystallization array based on the mother liquor composition used in a crystallization experiment selected through the course screen, indicated in FIG. 2 as the array labeled $FS_1$. The compositions of the mother liquors used in the fine screen crystallization array are selected by making small variations in the composition of the mother liquor used in the selected experiment from the course screen. For example, if the mother liquors used in the course screen had a pH between 2–8 and the mother liquor in the selected crystallization had a pH of 4.0, the mother liquors used in the fine screen experiments might have a pH between 3.4 to 4.6. Further, by focusing the array around mother liquors having a pH of about 4, one can reduce the incremental change in the value in the fine screen $FS_1$. For instance, the incremental change in the pH during the coarse screen $CS_2$ shown in FIG. 2 is 2.0 while the incremental change of the pH during the fine screen also shown in FIG. 2 is 0.4.

Crystals formed in each crystallization experiment in the fine screen are analyzed in order to select the one or more crystallization experiments yielding the best crystals or crystal-like precipitate. A crystallization experiment selected during the fine screen experiment is illustrated in FIG. 2 as a box having an X. If the crystals formed during the fine screen are of a sufficiently high quality, one might isolate the crystals formed in the experiment and perform x-ray diffraction on the isolated crystals to resolve the molecule's crystal structure. Alternatively, one might use the mother liquor used in the selected fine screen experiment in order to grow additional crystals. However, if the crystals formed during the fine screen are not of a sufficiently high quality, the mother liquor can be further optimized by taking the mother liquor used in the selected fine screen experiment as the starting point for an additional fine screen. FIG. 2 illustrates a second array of fine screen crystallization experiments labeled $FS_2$. It is noted that this iterative process of selecting a fine screen experiment and performing a finer screen array based on a selected experiment can be repeated until a suitable mother liquor is identified for use in preparing crystals.

The microcrystallization methods and apparatuses of the present invention may be used to perform the course screen array experiments described in regard to FIG. 2 in order to analyze a larger set of mother liquors than had previously been feasible with drop sizes larger than 1 microliter. It is noted that the fine screen array experiments may also be performed using the microcrystallization methods and apparatuses of the present invention or may be performed where drop sizes are larger than 1 microliter.

FIG. 3A illustrates a top view of a multiwell plate 34 which may be used with the methods and apparatuses of the present invention to perform a hanging drop array microcrystallization. As illustrated, the multiwell plate 34 includes a support structure 36 defining wells 38 arranged in 6 columns and 8 rows. Although FIG. 3A illustrates a multiwell plate 34 with a total of 48 wells 38, the multiwell plate 34 can include a different number of wells 38.

FIG. 3B provides a sideview of the multiwell plate 34 illustrated in FIG. 3A. Each well 38 includes an upper edge 40 extending above the support structure 36. The upper edge 40 is preferably wide enough that a layer of a sealing medium, such as grease, can be applied to the upper edge 40. The support structure 36 preferably has a geometry which allows multiwell plates 34 to be stacked on top of one another without one multiwell plate 34 interfering with the well contents of an adjacent multiwell plate 34.

Figure 3C:
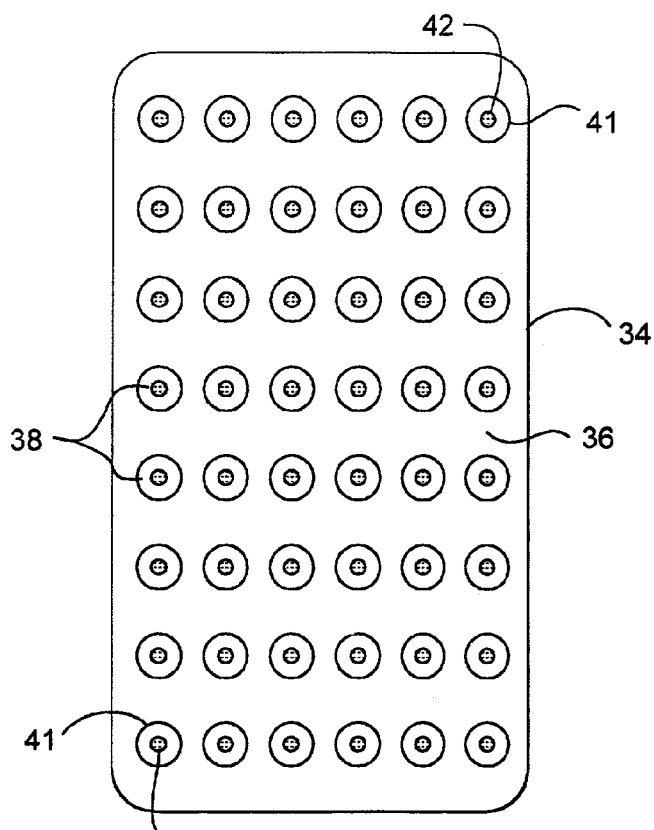
FIG. 3C illustrates a top view of a multiwell plate which may be used to perform a sitting drop array microcrystallization.

FIG. 3C illustrates a top view of a multiwell plate 34 which may be used with the methods and apparatuses of the present invention to 20 perform a sitting drop array microcrystallization. As illustrated, the multiwell plate 34 includes a support structure 36 defining 48 wells 38 arranged in 6 columns and 8 rows. Although a multiwell plate 34 with 48 wells 38 is illustrated the multiwell plate 34 can include a different number of wells 38. A well region 41 is adjacent to a sitting drop region 42. Although the sitting drop region 42 is illustrated as being centrally positioned within the well 38, the sitting drop region 42 can be positioned to one side of the well 38.

Figure 3D:
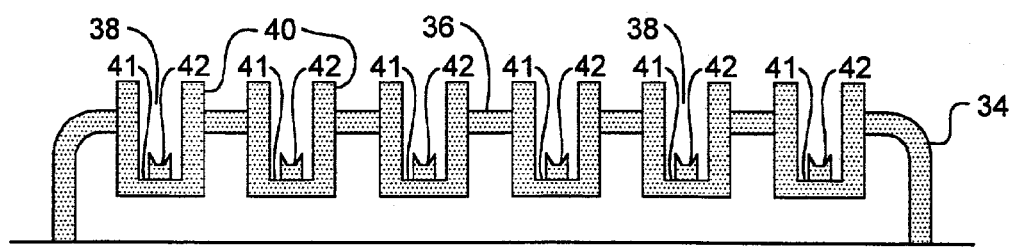
FIG. 3D is a sideview of the multiwell plate illustrated in FIG. 3C.

FIG. 3D provides a sideview of the multiwell plate 34 illustrated in FIG. 3C. The sitting drop region 42 extends upward from the bottom of the well 38. As illustrated by the cut-away, the sitting drop region 42 can include a recess where a sitting drop can be formed. Each well 38 includes an upper edge 40 extending above the support structure 36. The upper edge 40 is preferably wide enough that a layer of a sealing medium, such as grease, can be applied to the upper edge 40. The support structure 36 preferably has a geometry which allows multiwell plates 34 to be stacked on top of one another without one multiwell plate 34 interfering with the well 38 contents of an adjacent multiwell plate 34.

Figure 3E:
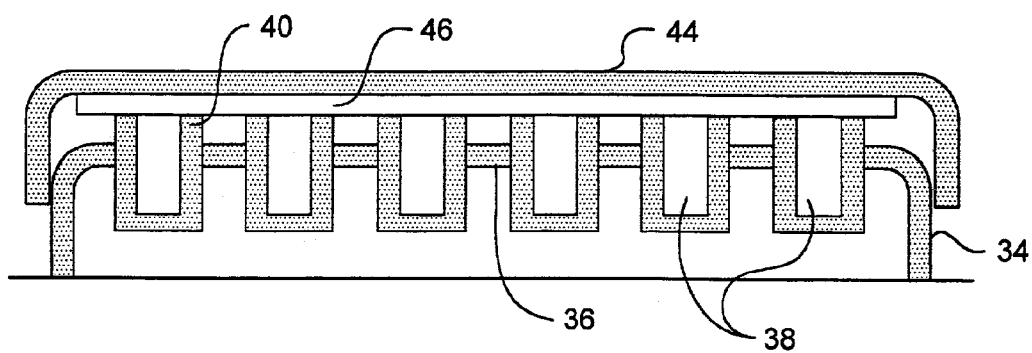
FIG. 3E is a cross section of a multiwell plate with a plate cover.

A plate cover 44 can be positioned over each multiwell plate 34 as illustrated in FIG. 3E. The plate cover 44 can be designed so the cover rests on the upper edges 40 of the wells 38. As illustrated in FIG. 3E an insert 46 can be positioned between the plate cover 44 and the multiwell plate 34 so the insert 46 rests on the upper edges 40 of the wells 38. The insert 46 can be removable from the plate cover 44 or can be permanently attached to the plate cover 44. The insert 46 can be formed from a flexible material so the insert 46 provides a seal between the insert 46 and the upper edges 40 of the wells 38 in order to reduce evaporation from the wells 38. Suitable materials for the insert 46 include, but are not limited to, soft rubbers and other gasket material.

As illustrated in FIG. 3A, the multiwell plate 34 can include a bar code 48 formed on the support structure 36. The multiwell plate 34 can also include a surface 50 sized to receive a bar code sticker. Alternatively, a bar code can be formed on a plate cover 44 or the plate cover 44 can include a surface sized to receive a bar code sticker. When the multiwell plate 34 or plate cover 44 includes a surface for receiving a bar code sticker, the bar code sticker is preferably removable from the multiwell plate 34 so different bar codes can be fixed to a single multiwell plate 34. As will be discussed later, these bar codes can be used to identify the multiwell plate 34 and/or the contents of the multiwell plate 34 to the system control logic.

Figure 4B:
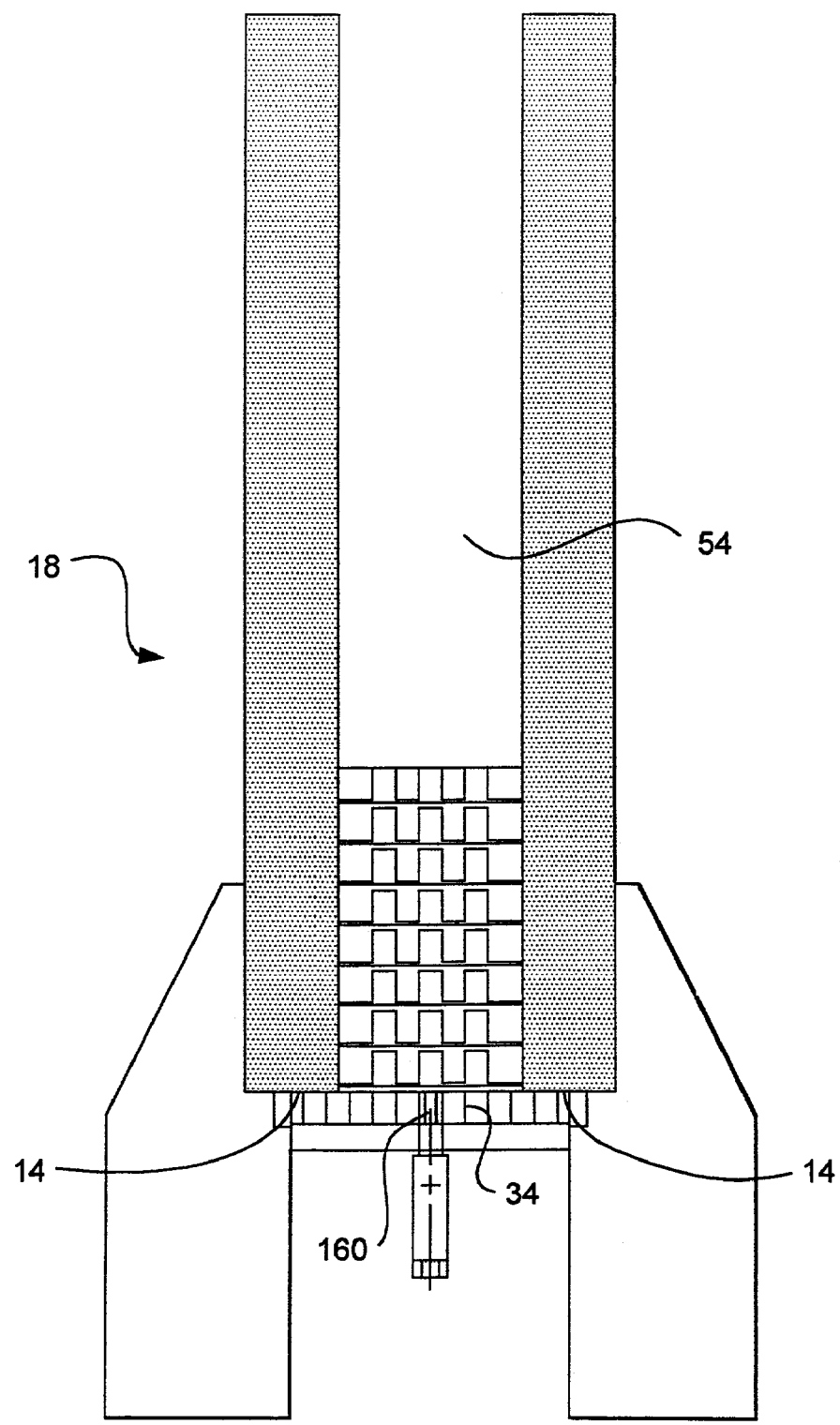

FIGS. 4A–4J illustrate embodiments of the various stations 12 of the mother liquor delivery system 31 illustrated in FIG. 1. FIGS. 4A and 4B illustrate a plate loading station 18 for sequentially loading multiwell plates 34 onto a plate track 14. FIG. 4A is a sideview of the plate loading station 18 looking across the plate track 14 and FIG. 4B is a sideview of the plate loading station 18 looking down the longitudinal axis of the plate track 14. The plate loading station 18 includes a tower 52 positioned over the plate track 14 so the plate track 14 extends outward from the base of the tower 52. The tower 52 includes a chute 54 sized to receive a stack of multiwell plates 34 arranged one on top of another.

The plate loading station 18 also includes plate lowering mechanics (not shown) which can be engaged to lower a multiwell plate 34 at the bottom of the stack onto the plate track 14. The action of gravity moves a new multiwell plate 34 into the position of the multiwell plate 34 lowered onto the plate track 14. The clearance between the plate tower 52 and the plate track 14 is enough for the plate transport assembly to transport the multiwell plate 34 lowered onto the plate track 14 out from under the tower 52 as illustrated in FIG. 4A. Once the multiwell plate 34 has been transported from beneath the tower 52, plate lowering mechanics can be re-engaged so a new multiwell plate 34 at the bottom of the chute 54 is also loaded onto the plate track 14. Because the plate loading station 18 can hold several multiwell plates 34 and sequentially position each multiwell plate 34 on the plate track 14, the mother liquor delivery system 31 can process many multiwell plates 34 without an operator manually positioning each multiwell plate 34 on the plate track 14.

The plate loading station 18 can be easily adapted into a plate 34 unloading station by operating the plate lowering mechanics in reverse. This reverse operation causes a multiwell plate 34 located beneath the tower 52 to be raised from the plate track 14 and added to the stack of multiwell plates 34 stored within the chute 54.

Figure 4C:
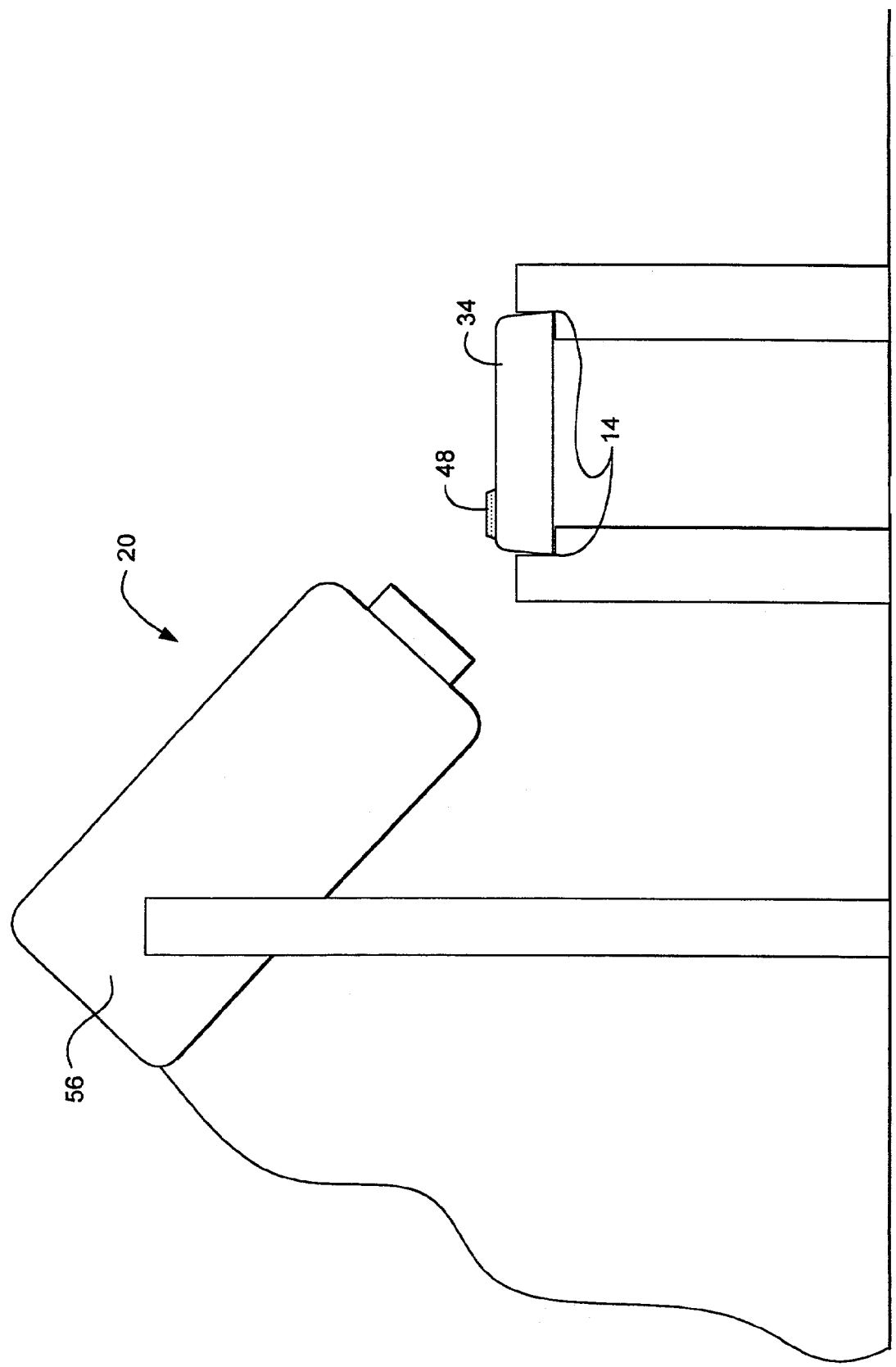

FIG. 4C illustrates a bar code reading station 20. A bar code reader 56 is positioned alongside the plate track 14. The bar code reader 56 is directed toward the plate track 14 at an angle which permits the bar code reader 56 to read a bar code 48 on a multiwell plate 34 on the plate track 14. As described above, these bar codes can formed on the multiwell plate 34 or can be included on a bar code sticker to be placed on the multiwell plates 34. The bar code reader 56 is monitored by the system control logic which associates each bar code with a particular multiwell plate 34 and/or with particular characteristics of a multiwell plate 34. Suitable characteristics include, but are not limited to, the number of wells 38 in the multiwell plate 34, the volume of the wells 38 in the multiwell plate 34, whether the multiwell plate 34 includes a plate cover 44, etc.

The characteristics of a multiwell plate 34 can be administratively entered in order to indicate information about the multiwell plate 34 to the system control logic. For instance, a user can enter characteristics such as identifying particular mother liquids to be delivered into particular wells 38 on a multiwell plate 34. Further, if an operator uses an external method to deliver mother liquids into the wells 38 of the multiwell plate 34, the user can indicate this to the system control logic. Because various mother liquids are already present in the wells 38 of the multiwell plate 34, the system control logic can override mother liquid delivery station in order to avoid delivering additional mother liquids to the wells 38 of the multiwell plate 34.

As a multiwell plate 34 moves through the mother liquor delivery system 31, the drop formation system 32 and/or through the crystallization system 10, the characteristics associated with the multiwell plate 34 can optionally be modified by the system control logic in order to reflect the changing status of the multiwell plate 34. For example, the system control logic can note when mother liquor has been added, or when drops have been formed.

Figure 4D:
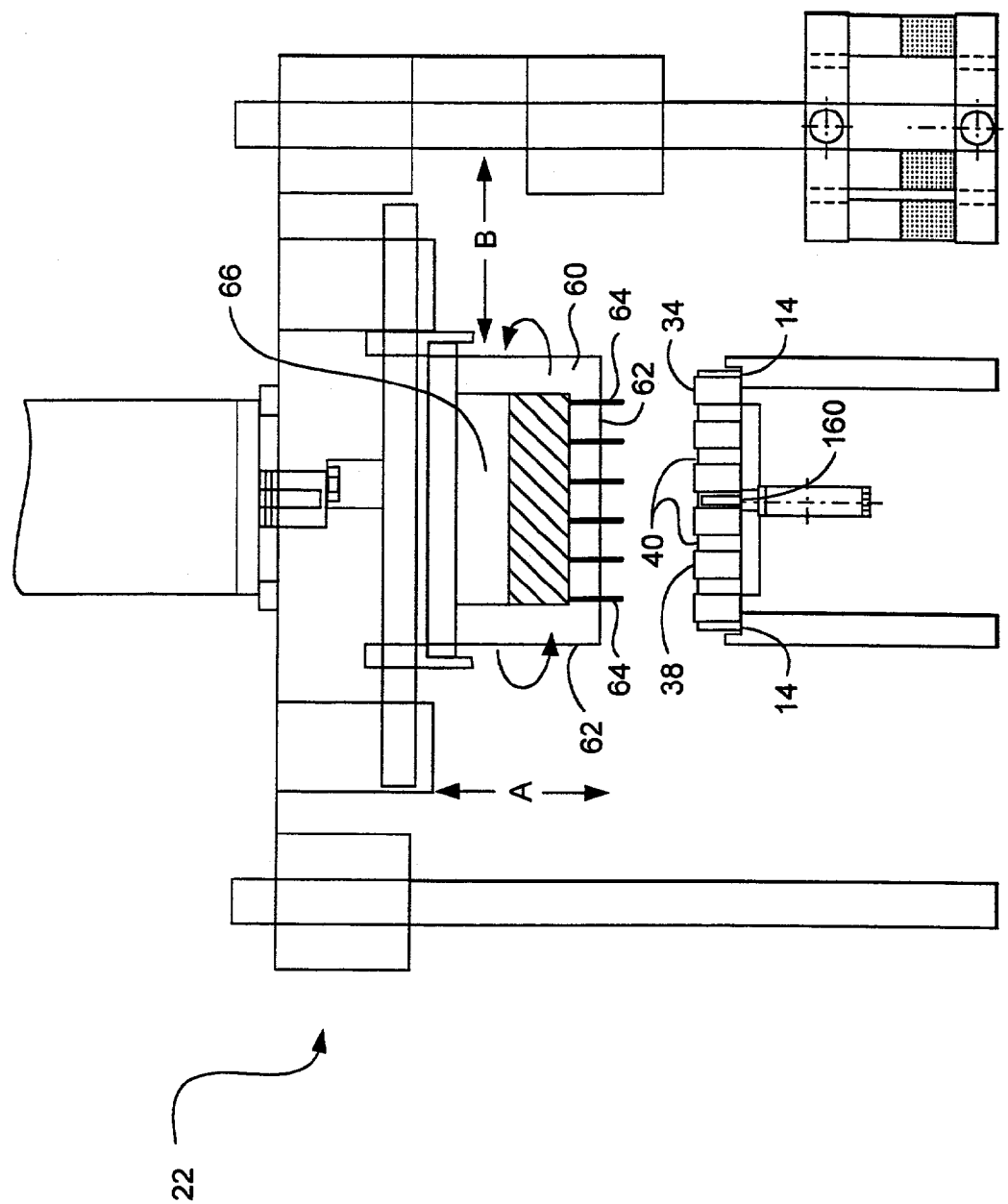

FIG. 4D illustrates a sealing medium station 22. The sealing medium station 22 includes a sealing member 60 suspended over the plate track 14 at a height which permits multiwell plates 34 to be moved under the sealing member 60. The sealing member 60 includes a sealing surface 62 with a plurality of sealing medium injectors 64 arranged so each sealing medium injector can be concurrently aligned with a well 38 in each multiwell plate 34. The sealing medium injectors 64 are in hydraulic communication with a sealing medium source 66. Accordingly, a sealing medium can be delivered from the sealing medium source 66 to the portion of the sealing surface 62 adjacent to the sealing medium injectors 64.

The sealing member 60 can be coupled with actuators for moving the sealing member 60 relative to the wells 38 on a multiwell plate 34. The sealing member 60 can be moved vertically over a multiwell plate 34 as illustrated by the arrows labeled A. The sealing member 60 can also be translated laterally relative to a multiwell plate 34 as illustrated by the arrows labeled B. Suitable actuators include, but are not limited to. pneumatic pistons, hydraulic pistons and electrically driven motors.

In operation of the sealing medium station 22, the plate transport assembly transports a multiwell plate 34 into a position where the wells 38 in the multiwell plate 34 are positioned beneath the sealing medium injectors 64. The sealing member 60 is lowered until the sealing surface 62 is in contact with the upper edge 40 of the wells 38 on the multiwell plate 34. Because the wells 38 of the multiwell plate 34 are aligned with the sealing medium injectors 64 before the downward motion of the sealing member 60, the upper edge 40 of each well 38 encircles a sealing medium injector. Once, the sealing surface 62 is in contact with the upper edges 40 of the wells 38, the sealing member 60 is laterally translated. The lateral translation causes the sealing member 60 to follow a circular path along an edge of the well 38, although other paths may also be used depending on the geometry of the wells 38. This lateral translation transfers the sealing medium delivered to the sealing surface 62 to the upper edge 40 of each well 38.

The amount of sealing medium transferred to the upper edge 40 of each well 38 depends on the amount of sealing medium present on the sealing surface 62 adjacent to the sealing medium injectors 64. The amount of sealing medium delivered to the upper edges 40 of the wells 38 should be sufficient to create a substantially airtight seal between a coverslip and the upper edge 40 of the well 38. Suitable sealing mediums include, but are not limited to, grease and vasaline.

It is noted in regard to the sealing medium station 22 that the station may be readily adapted for use with hanging drop array crystallizations as well as with sitting drop array crystallizations. In regard to each type of drop array crystallization, an airtight seal should be formed between the edges of a well 38 and a coverslip or other form of covering member which is placed over the well 38.

Figure 4E:
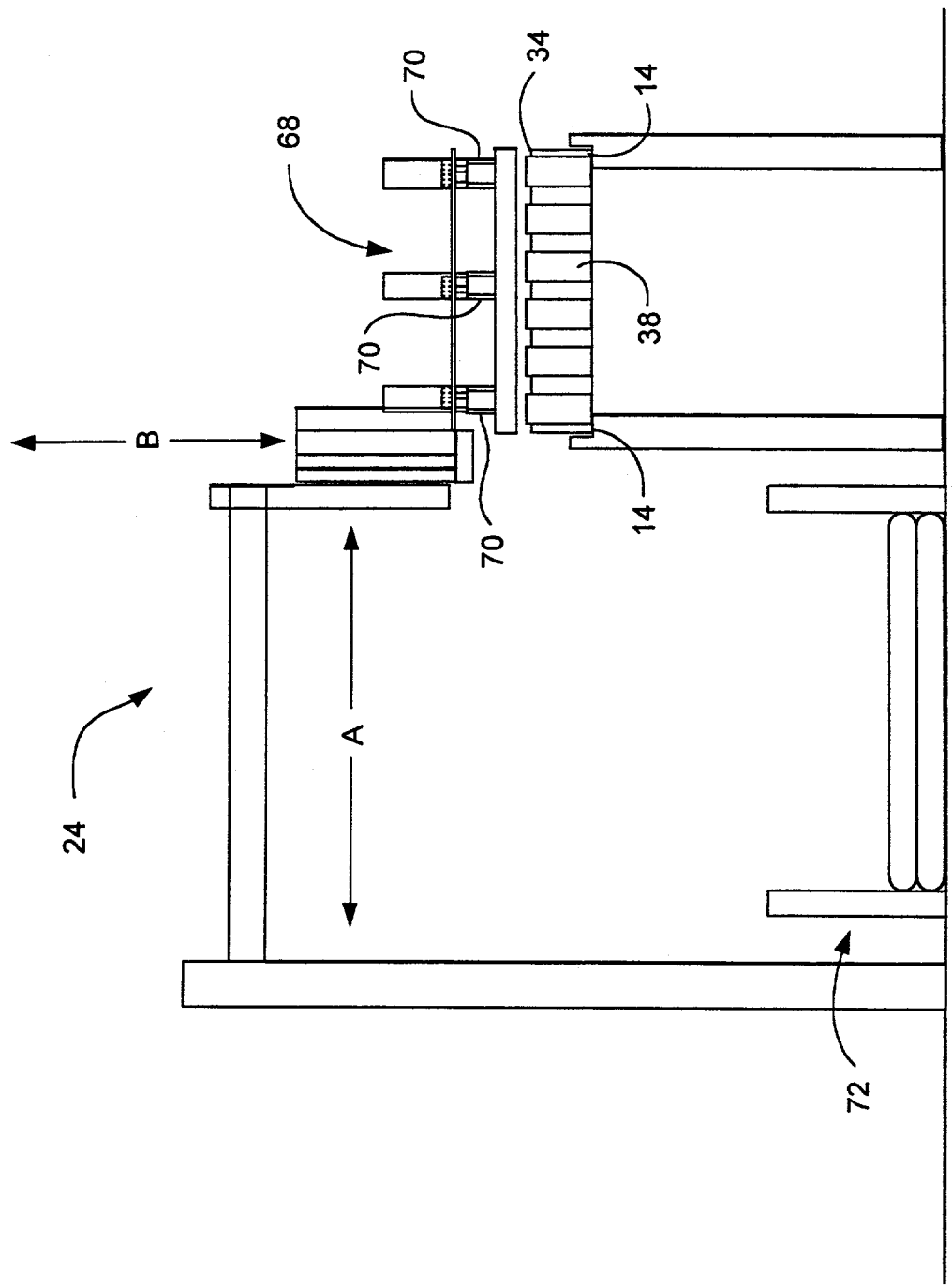

FIG. 4E is a sideview of a plate cover 44 removal station 24 positioned adjacent a plate track 14. The plate cover 44 removal station 24 includes a carriage 68 configured to move vertically as illustrated by the arrow labeled A and laterally as illustrated by the arrow labeled B. A plurality of vacuum fittings 70 are coupled with the carriage 68 and are in pneumatic communication with a releasable vacuum source. Suitable vacuum fitting include, but are not limited to, rubber fittings having a cup shape and including a vacuum port in pneumatic communication with a vacuum source.

During operation of the plate cover removal station 24, the plate transport assembly moves a multiwell plate 34 into position next to the plate cover removal station 24. If the multiwell plate 34 has a plate cover 44, the carriage 68 is moved laterally until each of the vacuum fittings 70 are positioned over the multiwell plate 34. The carriage 68 is lowered until at least a portion of the vacuum fittings 70 are in contact with the plate cover 44. The vacuum source is activated in order to immobilize the plate cover 44 relative to the carriage 68. The carriage 68 is then raised to its original height. The vertical motion of the carriage 68 lifts the plate cover 44 from the multiwell plate 34. The carriage 68 is then moved laterally until the carriage 68 is positioned over a plate cover storage component 72. The carriage 68 is lowered into the plate cover storage component 72 and the vacuum source disengaged in order to drop the plate cover 44 into the plate cover storage component 72. Finally, the carriage 68 is then returned to its original position.

The plate cover removal station 24 can be adapted to a plate cover delivery station 29 by operating the plate cover removal station 24 in reverse. The reverse operation causes a plate cover 44 to be removed from the plate cover storage component 72 and then placed on a multiwell plate 34. When a crystallization system 10 uses both a plate cover removal station 24 and a plate cover delivery station 29, the plate covers 44 used with the plate cover removal station 24 can be the same as or different from the plate covers 44 used with the plate cover delivery station 29.

Figure 4F:
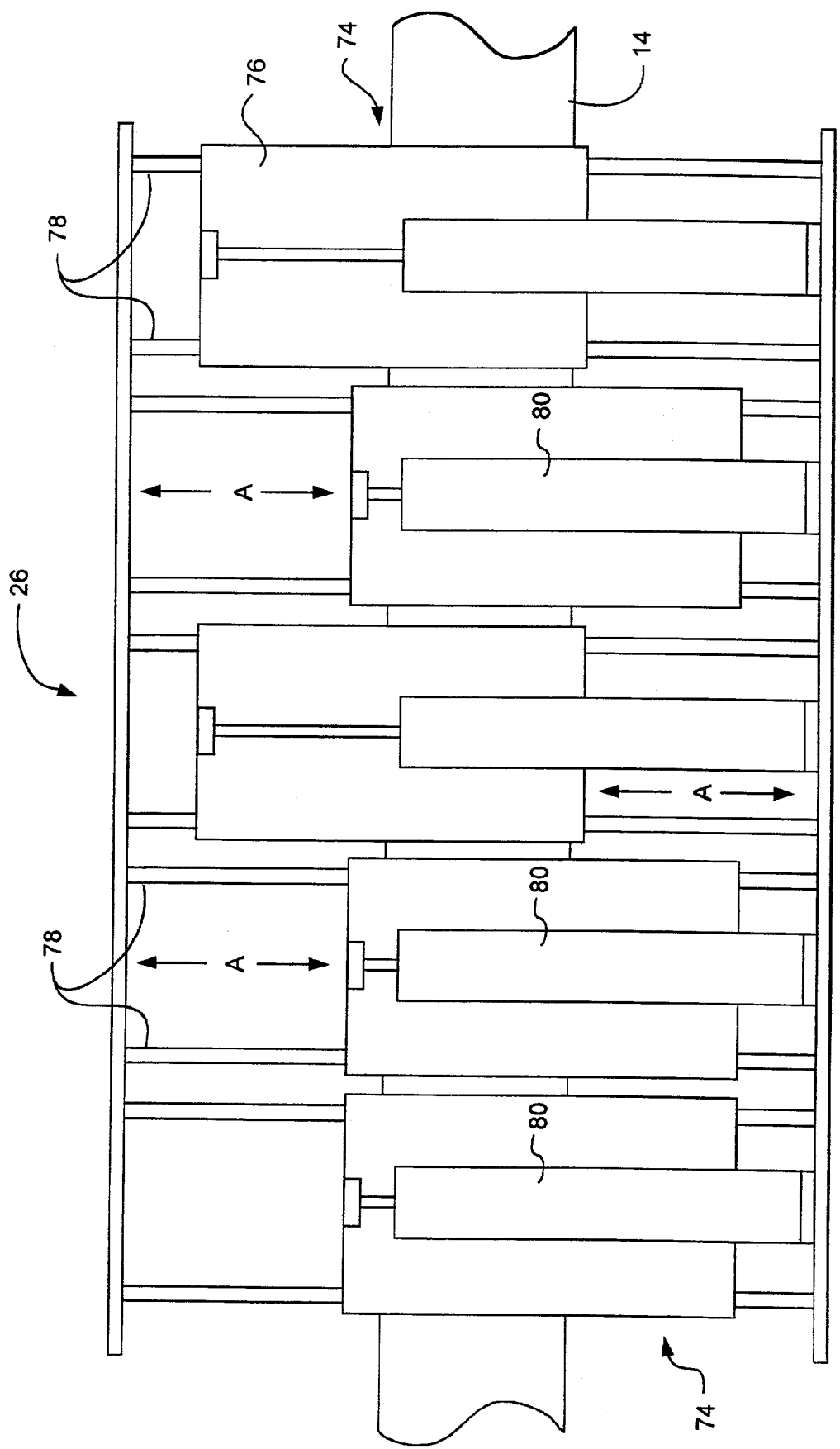

FIG. 4F is a top view of a mother liquor delivery station 26 where a mother liquor is delivered into the wells 38 of a multiwell plate 34. The mother liquor delivery station 26 includes a plurality of delivery shuttles 74. Each shuttle includes a delivery block 76 configured to slide along block supports 78. The delivery blocks 76 are coupled with block actuators 80 to slide the delivery blocks 76 in a lateral direction relative to the plate track 14 as illustrated by the arrow labeled A. Suitable block actuators 80 include, but are not limited to, pneumatic pistons, hydraulic pistons and electric motors.

Figure 4G:
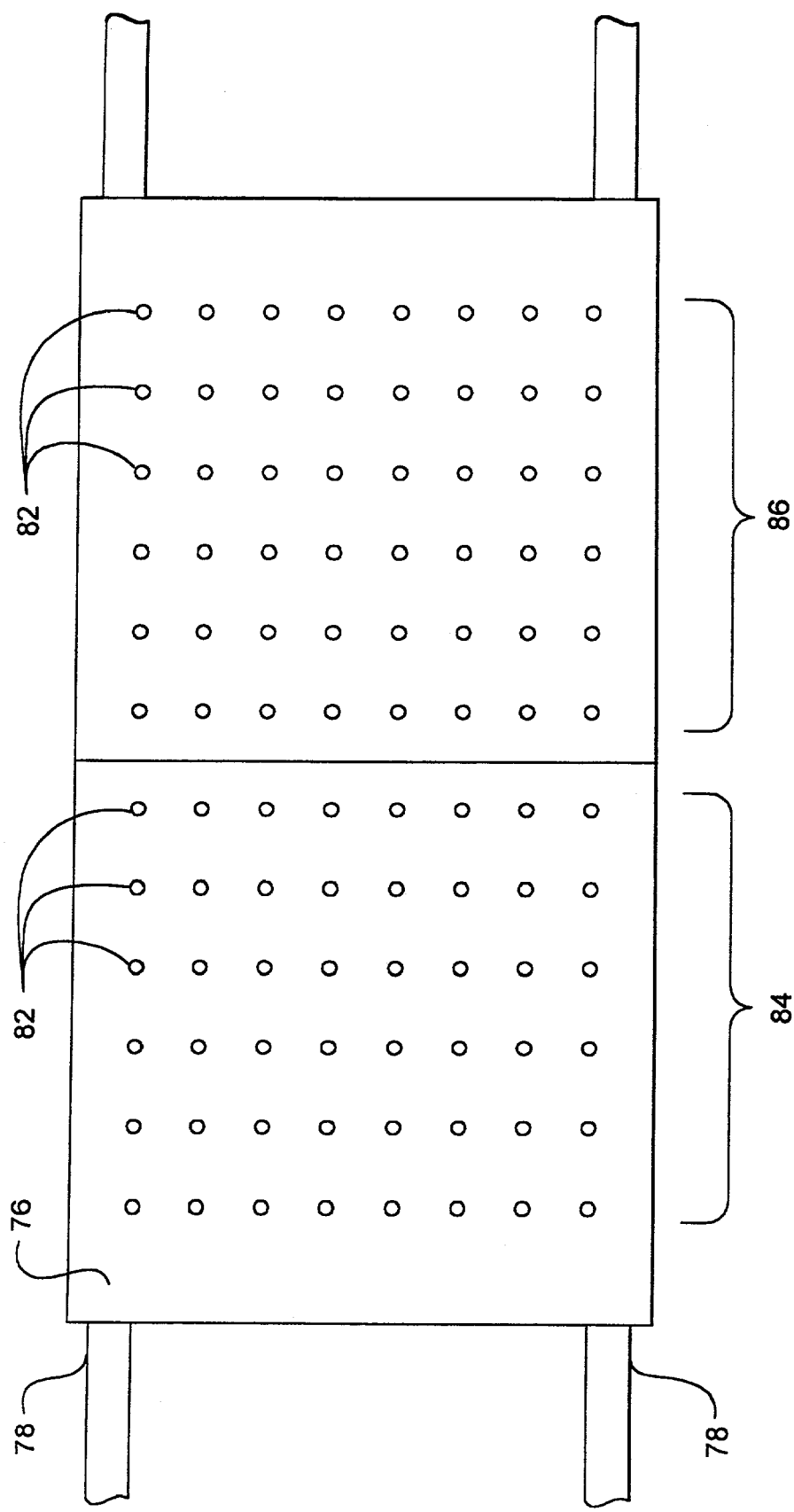
Figure 4H:
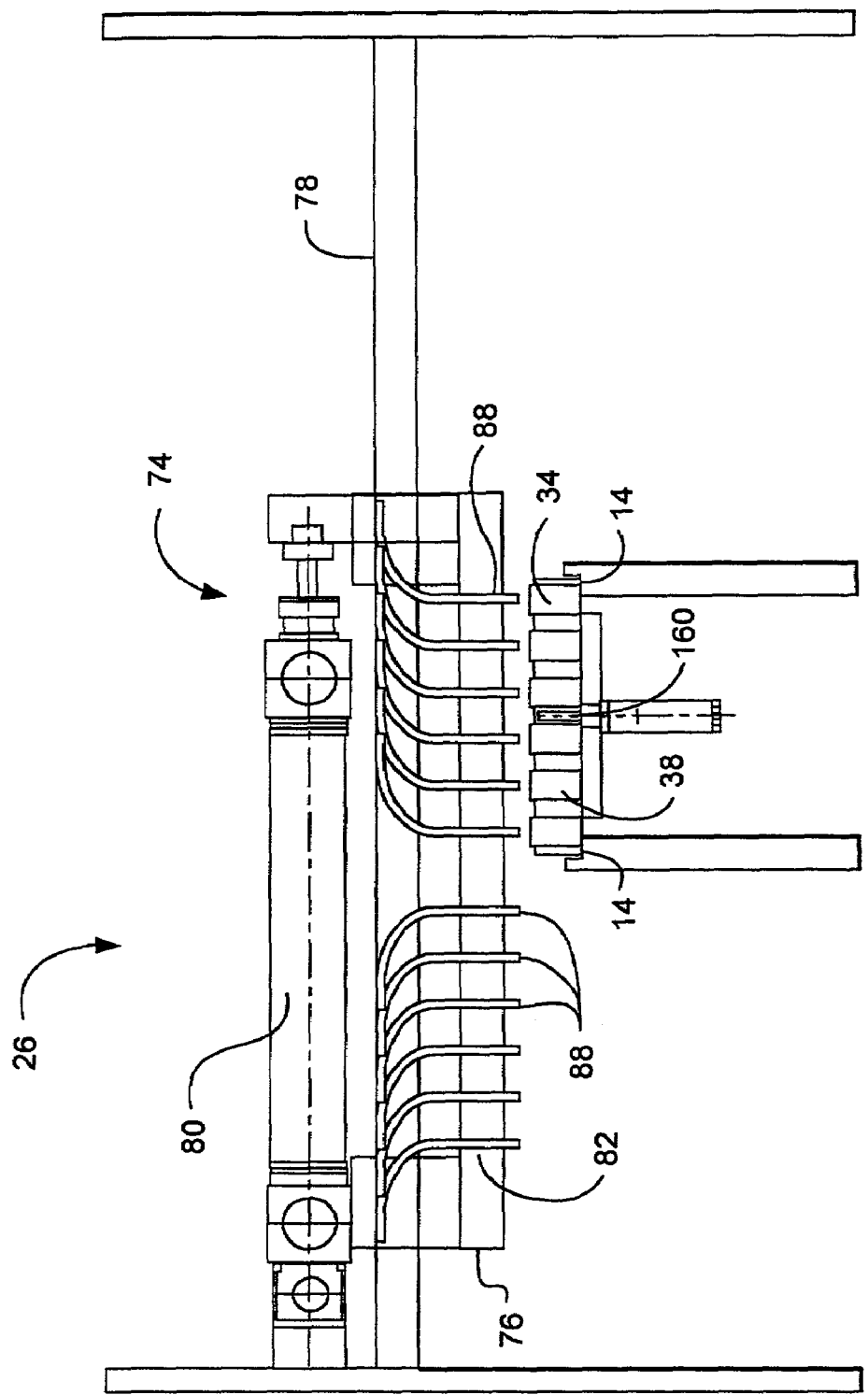

FIG. 4G provides a top view of a delivery block 76. A plurality of lumens 82 extend through the delivery block 76. The lumens 82 are divided into a first delivery group 84 and a second delivery group 86. A fluid injector 88 such as a syringe, can be removably positioned in each of the lumens 82 as illustrated in FIG. 4H. The lumens 82 in each delivery group 84, 86 are arranged on the delivery block 76 so each fluid injector 88 can be concurrently aligned with a different well 38 of a multiwell plate 34. Accordingly, the number of lumens 82 in each delivery group 84. 86 is preferably equal to the number of wells 38 in the multiwell plate 34. For instance, when the multiwell plates 34 include 48 wells 38, each delivery group 84, 86 preferably includes 48 lumens 82.

Each fluid injector 88 is in fluid communication with a mother liquor source. More than one fluid injector 88 can be in fluid communication with a single mother liquor source. However, each fluid injector 88 is preferably in fluid communication with a different mother liquor source. FIG. 4H illustrates a mother liquor delivery station 26 having five first delivery groups 84 and five second delivery groups 86 which each include 48 fluid injectors 88. Accordingly, 480 mother liquor sources are required when each fluid injector 88 is in fluid communication with a different mother liquor source.

Figure 4I:
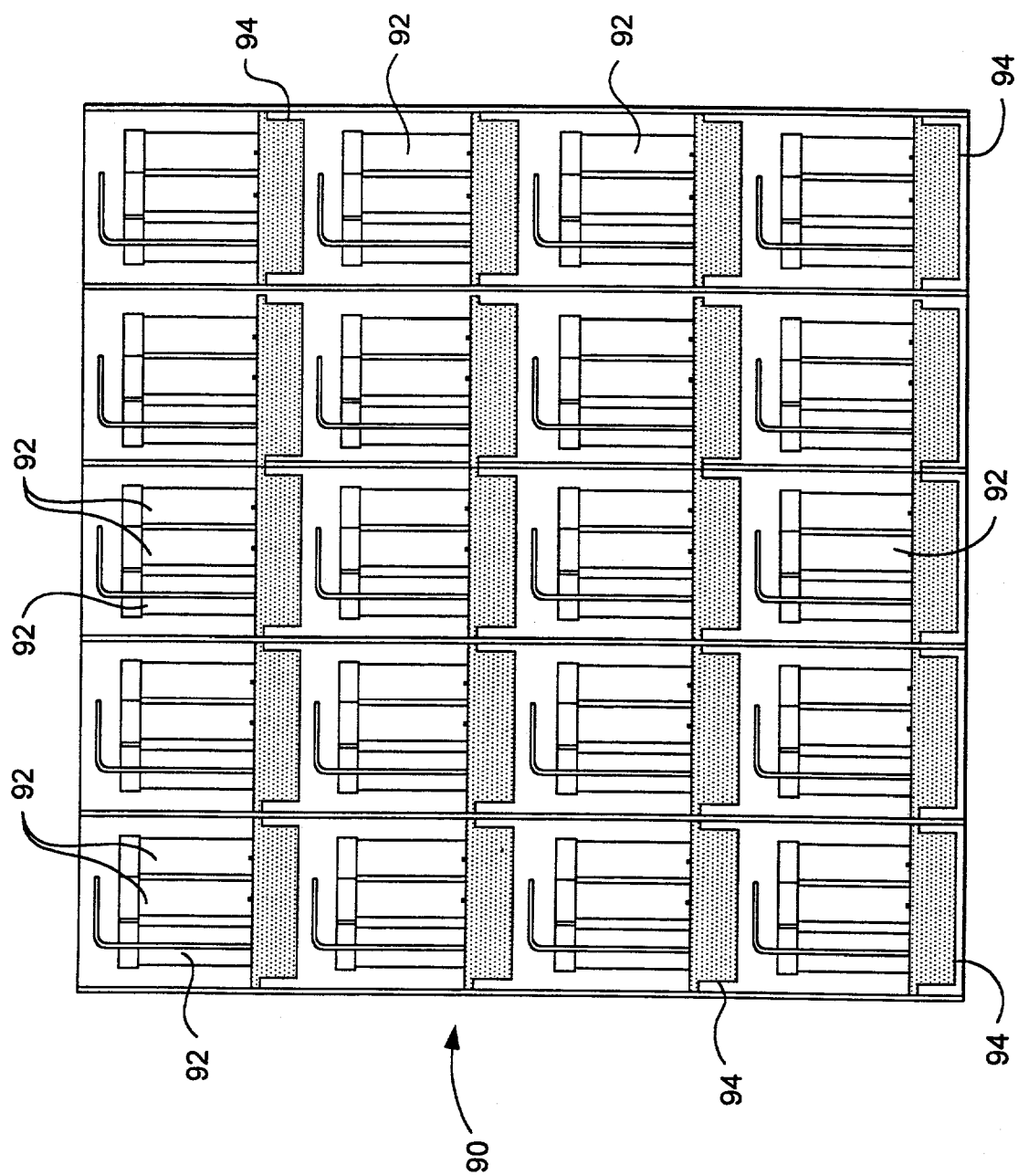

FIG. 4I is a sideview of a mother liquor source storage bank 90 for holding different mother liquor sources 92. The bank 90 includes source holders 94 arranged in five columns and four rows. Each source holder 94 can hold a plurality of mother liquor sources 92 and can be slid in and out of the bank 90 to provide easy access to the mother liquor sources 92 being held by a single source holder 94. When each multiwell plate 34 has 48 wells 38, each source holder 94 preferably holds 12 different mother liquor sources 92.

Accordingly, each column contains 48 mother liquor sources 92 which can each be in fluid communication with a different fluid injector 88 included in the same delivery group 84, 86. As a result, each column of mother liquor sources 92 can be associated with a single delivery group 84, 86. A mother liquor source bank 90 can be included on each side of the plate track 14. The mother liquor sources 92 positioned on one side of the plate track 14 can be in fluid communication with the delivery groups 84, 86 nearest that side of the track while the mother liquor sources 92 positioned on the opposing side of the plate track 14 can be in fluid communication with the delivery groups 84. 86 on the opposing side of the plate track 14.

During operation of the mother liquor delivery station 26, the plate transport assembly moves a multiwell plate 34 beneath a particular one of the delivery blocks 76. The block actuators 80 can then move the delivery blocks 76 so the injectors in a particular delivery group 84, 86 are aligned with the wells 38 in the multiwell plate 34. The particular delivery block 76 and the particular delivery group 84, 86 are associated with the mother liquors which the operator desires to be delivered into the wells 38 of the multiwell plate 34. The mother liquors are then delivered from the mother liquor sources 92 through the fluid injectors 88 and into the wells 38 which are aligned with the mother liquors. The delivery of mother liquid into each of the wells 38 can occur concurrently and the same volume of mother liquor is preferably delivered into each of the wells 38.

Figure 4J:
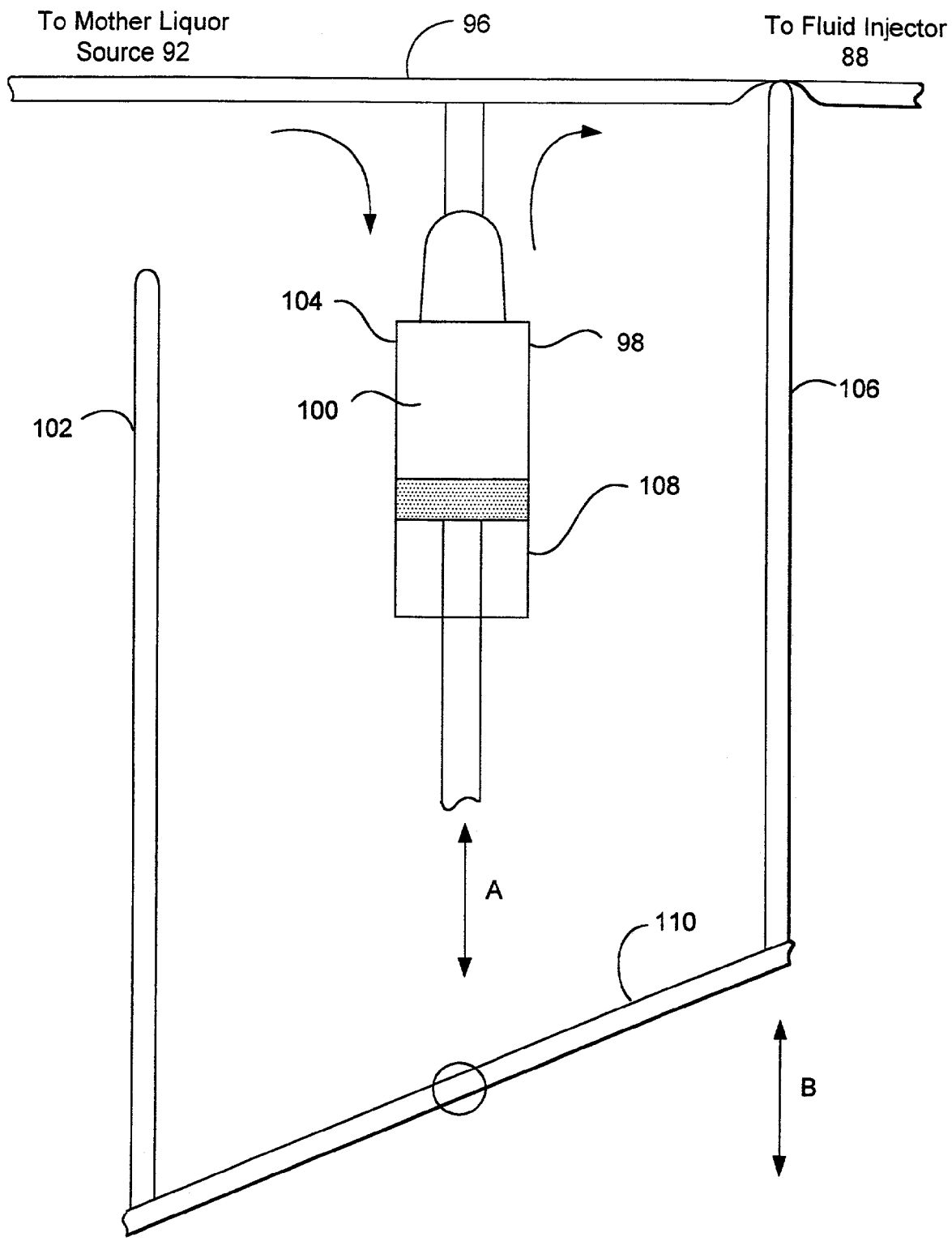

FIG. 4J illustrates a syringe pump for delivering mother liquor from mother liquor sources 92 into a well 38 of a multiwell plate 34 through a fluid injector 88. Mother liquor flows from a mother liquor source 92 to the fluid injector 88 through a fluid conduit 96. The fluid conduit 96 is in fluid communication with a syringe 98 positioned between the mother liquor source 92 and the fluid injector 88. The volume within the syringe 100 can be mechanically compressed and expanded as illustrated by the arrow labeled A. A first pinch bar 102 is positioned on an input side of the syringe 104 and a second pinch bar 106 is positioned on an output side of the syringe 108. The first pinch bar 102 and the second pinch bar 106 are coupled with a rocker bar 110. In FIG. 4J, the rocker bar 110 occupies a first position where the first pinch bar 102 has pinched the fluid conduit 96 shut on the input side of side of the syringe while the output side of the syringe 108 remains unobstructed. The rocker bar 110 can occupy a second position where the second pinch bar 106 has pinched the fluid conduit 96 shut on the output side of the syringe 108 while the output side of the syringe 108 remains unobstructed. The rocker bar 110 can be automatically moved between the first and second positions as illustrated by the arrow labeled B.

During operation of the syringe pump, the rocker bar 110 occupies the first position and the volume within the syringe 100 is expanded by the amount of mother liquor to be delivered into a well 38 from the fluid injector 88. Because the fluid conduit 96 on the output side of the syringe 108 is pinched closed, the expansion of the volume within the syringe 100 by a particular amount causes that particular amount to be withdrawn from the mother liquor source 92. The rocker bar 110 is then moved to the second position and the volume within the syringe 100 compressed by the amount of mother liquor to be delivered into the well 38 through the fluid injector 88. Because the fluid conduit 96 on the input side of the syringe 104 is closed, the compression of the volume within the syringe 100 by the particular amount causes that particular amount to flow through the fluid injector 88 and into the associated well 38.

The mother liquor delivery section discussed above is for illustrative purposes only and many variations are possible. For instance, a mother liquor delivery station 26 can include more than five delivery shuttles 74 or as few as one. Further, each delivery shuttle 74 can include more than two delivery groups or a few as one. When a delivery shuttle 74 includes a single delivery group, the block actuators 80 can be eliminated and the delivery shuttles 74 can be stationary relative to the plate track 14. Additionally, the combination of the plate track 14 movement and the delivery block 76 movement can be used to position a particular fluid injector 88 over a particular well 38 and the mother liquors can be sequentially delivered into the wells 38. Accordingly, a particular mother liquor can be delivered into a particular well 38.

FIGS. 5A–5E illustrate various stations 12 that may be included in a drop formation system 32. It is noted that the drop formation system 32 illustrated in regard to FIGS. 5A–5E is adapted for a hanging drop array crystallization. The drop formation system 32 can be readily modified for a sitting drop array crystallization by causing the mother liquor drops and molecule solution drops to be deposited on a sitting drop region 42 of a multiwell plate 34, such as the one illustrated in FIG. 3C, as opposed to on a coverslip.

Figure 5A:
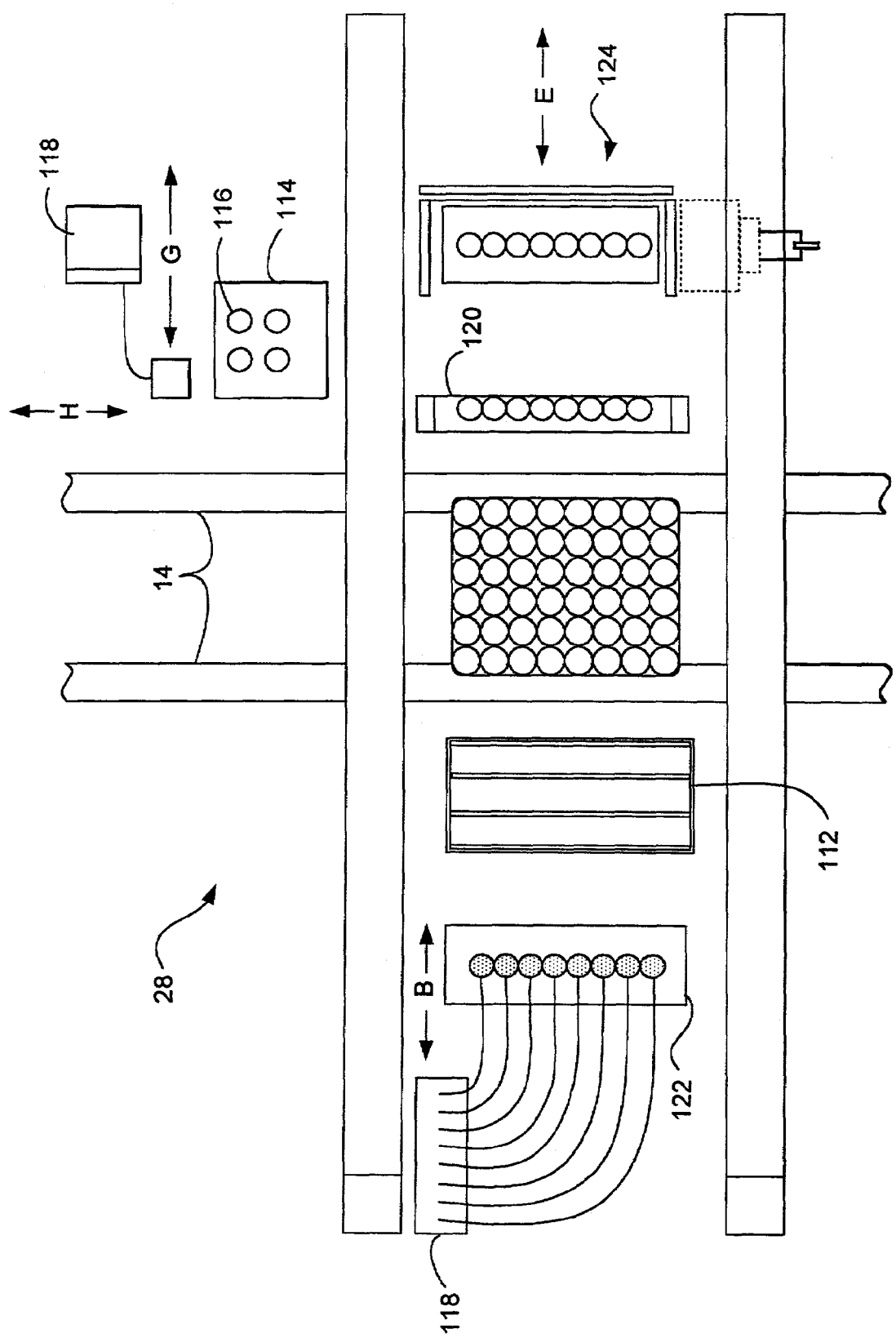
Figure 5B:
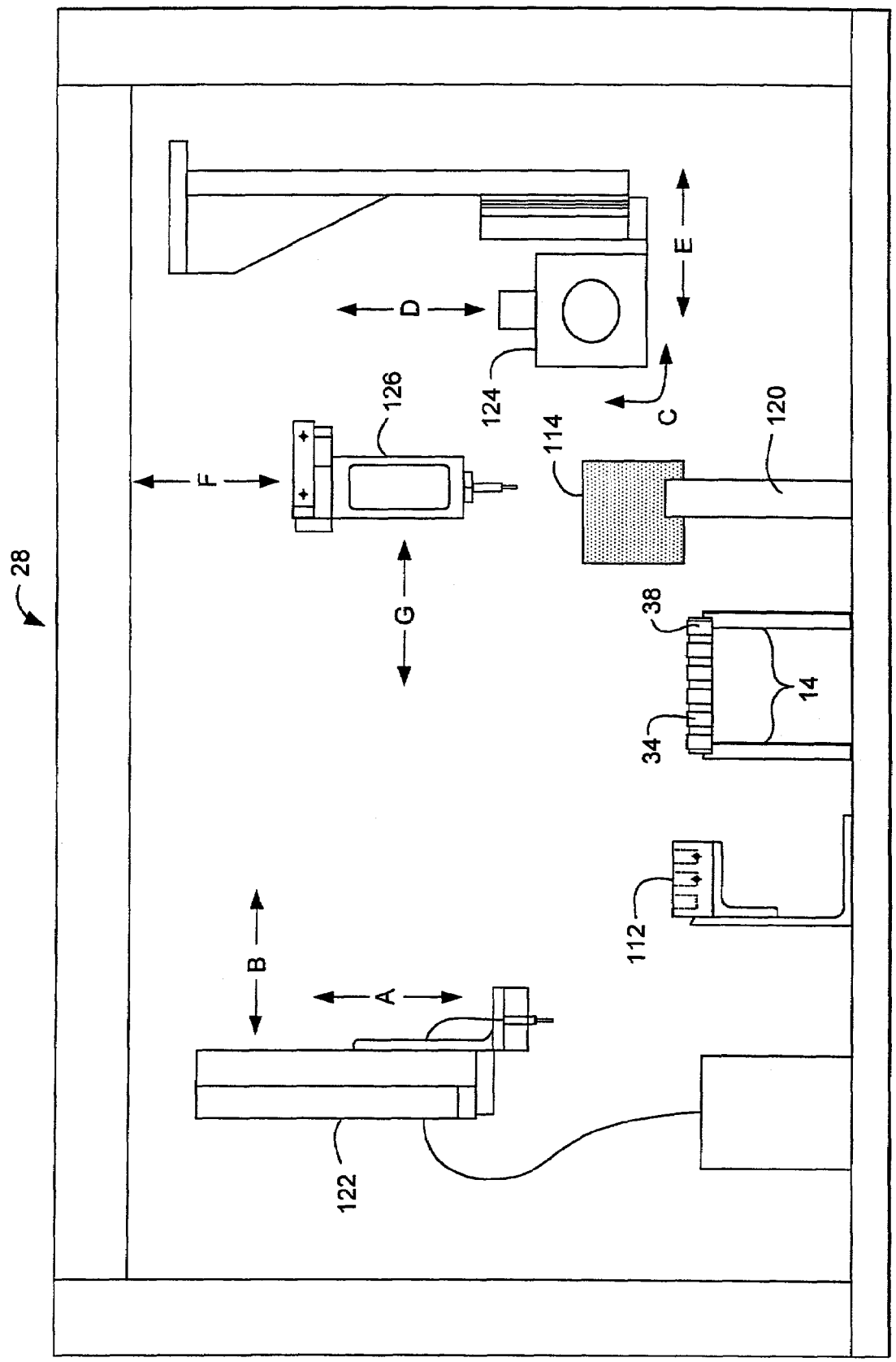

FIGS. 5A is a top view of a drop formation station 28 and FIG. 5B is a sideview of the drop formation station 28. The drop formation station 28 includes a wash basin 112 through which a cleansing solution can be flowed. Suitable cleansing solutions include, but are not limited to, water. The drop formation station 28 also includes a molecule solution storage component 114 having one or more molecule solution wells 116 for storing solutions containing the molecule to the crystallized. The molecule solution wells 116 can be capped for storing the molecule solutions when the drop formation system 32 is not in operation. The molecule solution storage component 114 can be refrigerated in order to provide cooling to the molecule solution within the molecule solution wells 116. For example, when the molecule solution is a molecule solution, the solution is preferably kept at 3–4° C. whether the drop formation station 28 is or is not in operation. The drop formation station 28 also includes syringe pumps 118 and a coverslip storage component 120 for storing coverslips.

The drop formation station 28 also includes a pipette holder 122 configured to move vertically as indicated by the arrow labeled A and laterally as indicated by the arrows labeled B. The pipette holder's 122 lateral range of motion allows the pipette holder 122 to move to a variety of positions including a position over the wash basin 112 and a position over the coverslip holder 124. The drop formation station 28 also includes a coverslip holder 124 configured to be inverted as indicated by the arrow labeled C. The coverslip holder 124 can move vertically as indicated by the arrow labeled D and laterally as indicated by the arrows labeled E. The pipette holder's 122 lateral range of motion allows the pipette holder 122 to move to a variety of positions including a position over the coverslip storage component 120 and several positions over the plate track 14. The drop formation station 28 also includes a molecule delivery pipette 126 which is configured to move vertically as indicated by the arrow labeled F, laterally as indicated by the arrow labeled G and longitudinally as indicated by the arrow labeled H. The longitudinal and lateral ranges of motion allow the molecule delivery pipette 126 to be moved to a variety of positions including a position over each molecule solution well and a plurality of positions over the coverslip holder 124.

The above movements can be achieved by coupling the pipette holder 122, coverslip holder 124 and the molecule delivery pipette 126 to a variety of different actuators. Suitable actuators include, but are not limited to, pneumatic pistons, hydraulic pistons and a variety of motors.

FIG. 5C is a sideview of a pipette holder 122. The pipette holder 122 includes a pipette support frame 128. The pipette support frame 128 holds a number of pipettes 130 equal to the number of wells 38 in a column of a multiwell plate 34. The pipettes 130 are held at a spacing which approximates the spacing between the wells 38 in the column of the multiwell plate 34. This spacing permits each pipette 130 to be concurrently aligned with a different well 38 in the column.

Each pipette 130 includes a valve 132 and a conduit 134 extending from the valve 132 to a syringe pump 118. The syringe pump 118 can be used to draw fluid into the pipettes 130 and to drive fluid out of the pipettes 130. The valve 132 is configured to deliver drops of a particular size from the pipette 130. These drops are delivered from the pipette 130 until a desired total volume is delivered from the pipette 130. Suitable valves 132 include, but are not limited to, piezoelectric valves and solenoid valves which can be configured to deliver drops as small as 380 pL. This allows production of mother liquor drops as small as 380 pL. Further reduction in the drop size delivered by these pipettes 130 may also be possible, would be desired, and is intended to fall within the scope of the present invention.

The pipette arrangement used for the molecule delivery pipette 126 is similar to the pipette arrangement used for the pipettes 130 within the pipette holder 122. Accordingly, the molecule delivery pipette 126 also includes a valve 132 and a conduit 134 extending from the valve 132 to a syringe pump 118. The molecule delivery pipette 126 is able to produce molecule solution drops as small as 380 pL. Further reduction in the drop size delivered may also be possible, would be desired, and is intended to fall within the scope of the present invention.

Figure 5D:
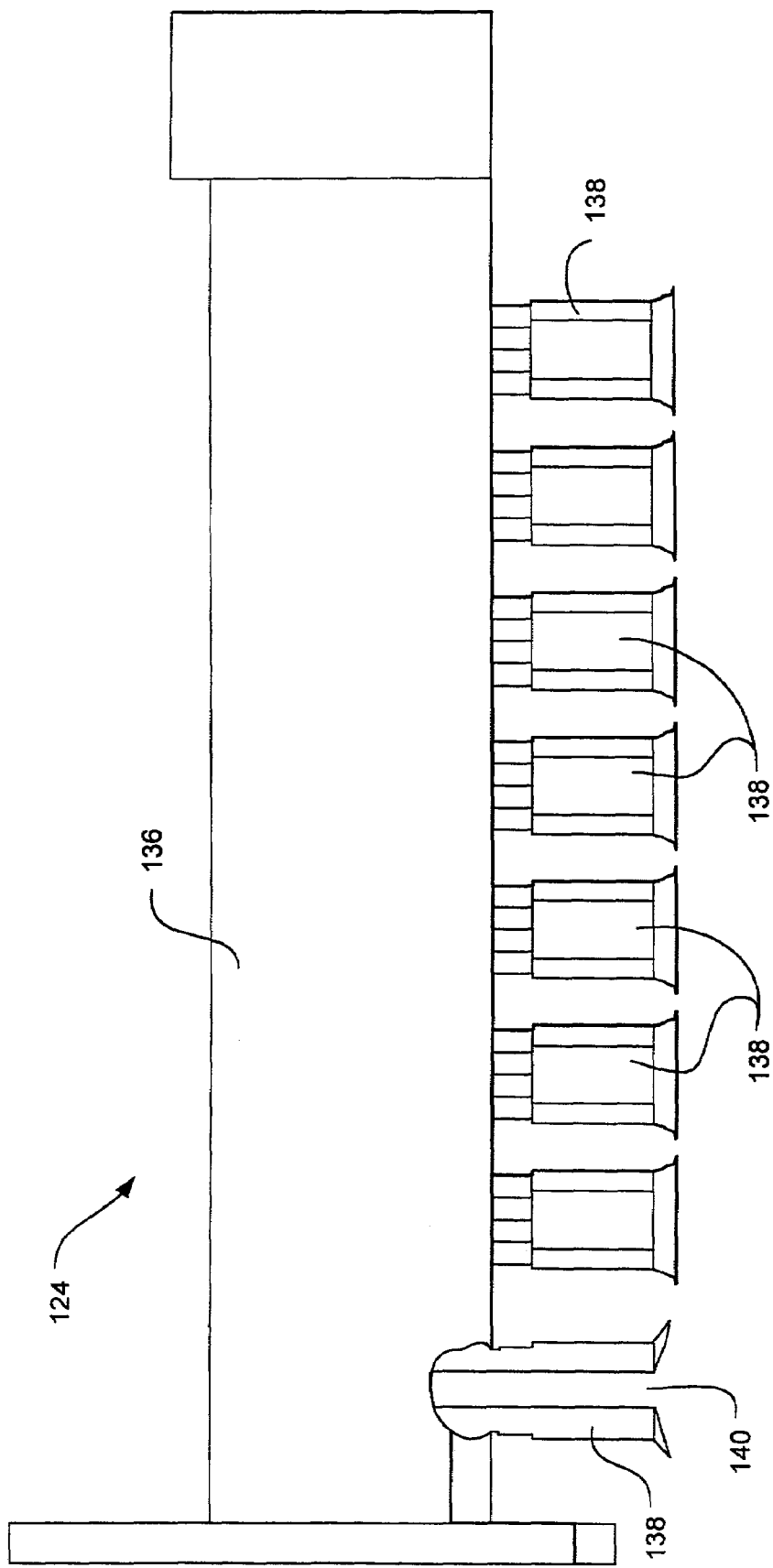

FIG. 5D is a sideview of a coverslip holder 124. The coverslip holder 124 includes a frame 136 which supports a plurality of support cups 138 shaped to removably hold coverslips at a spacing which approximates the spacing between the wells 38 in a column of the multiwell plate 34. This spacing permits each coverslip to be concurrently aligned with a different well 38 in a column of the multiwell plate 34.

The support cups 138 can include an attachment mechanism 140 for immobilizing the coverslips in place relative to the support cups 138. The attachment mechanism 140 serves to keep the coverslips in place when the coverslip holder 124 is inverted. However, the attachment mechanisms 140 can release the coverslips at a desired moment. Suitable coverslip holder 124 attachment mechanisms 140 include, but are not limited to, a vacuum source in pneumatic communication with vacuum ports positioned in the support cups 138. Pulling a vacuum through the vacuum ports serves to keep the coverslips in place on the coverslip holder 124. However, when the coverslip holder 124 is inverted, the vacuum can be released by disengaging the vacuum source or reversing the vacuum. The release of the vacuum releases the coverslips from the coverslip holder 124.

Figure 5E:
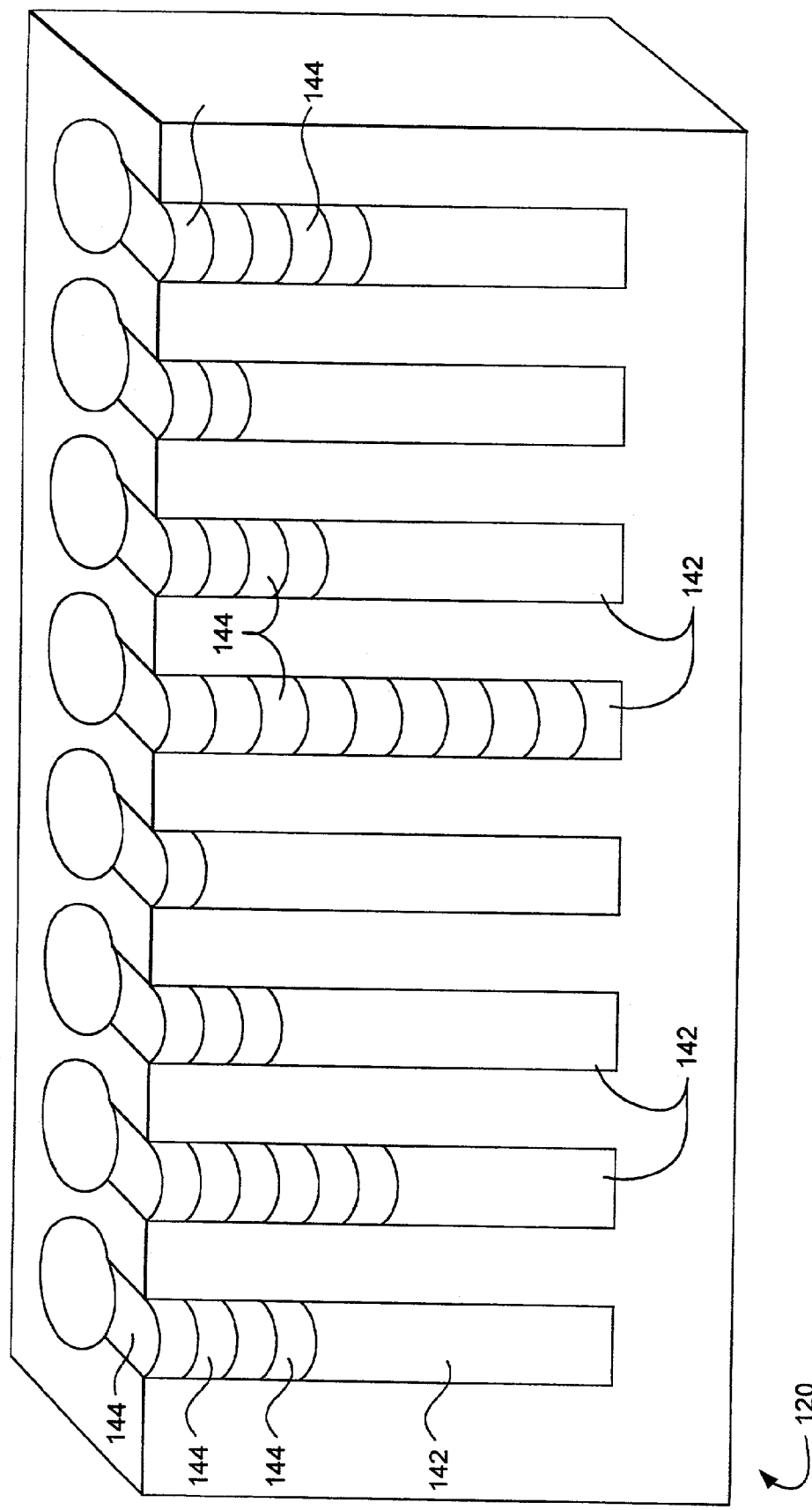

FIG. 5E is a sideview of a coverslip storage component 120 which includes a plurality of magazines 142 sized to hold coverslips 144 stacked on top of one another. The stack of coverslips 144 within the magazine 142 can be biased upward until the coverslip 144 on the top of the stack is near the top of the magazine 142. The spacing between the magazines 142 approximates the spacing between the support cups 138 of the coverslip holder 124. This spacing permits each magazine 142 to be concurrently aligned with a different support cup 138 of the coverslip holder 124. Accordingly, a coverslip 144 from each magazine 142 can also be aligned with a different support cup 138.

Figure 6A:
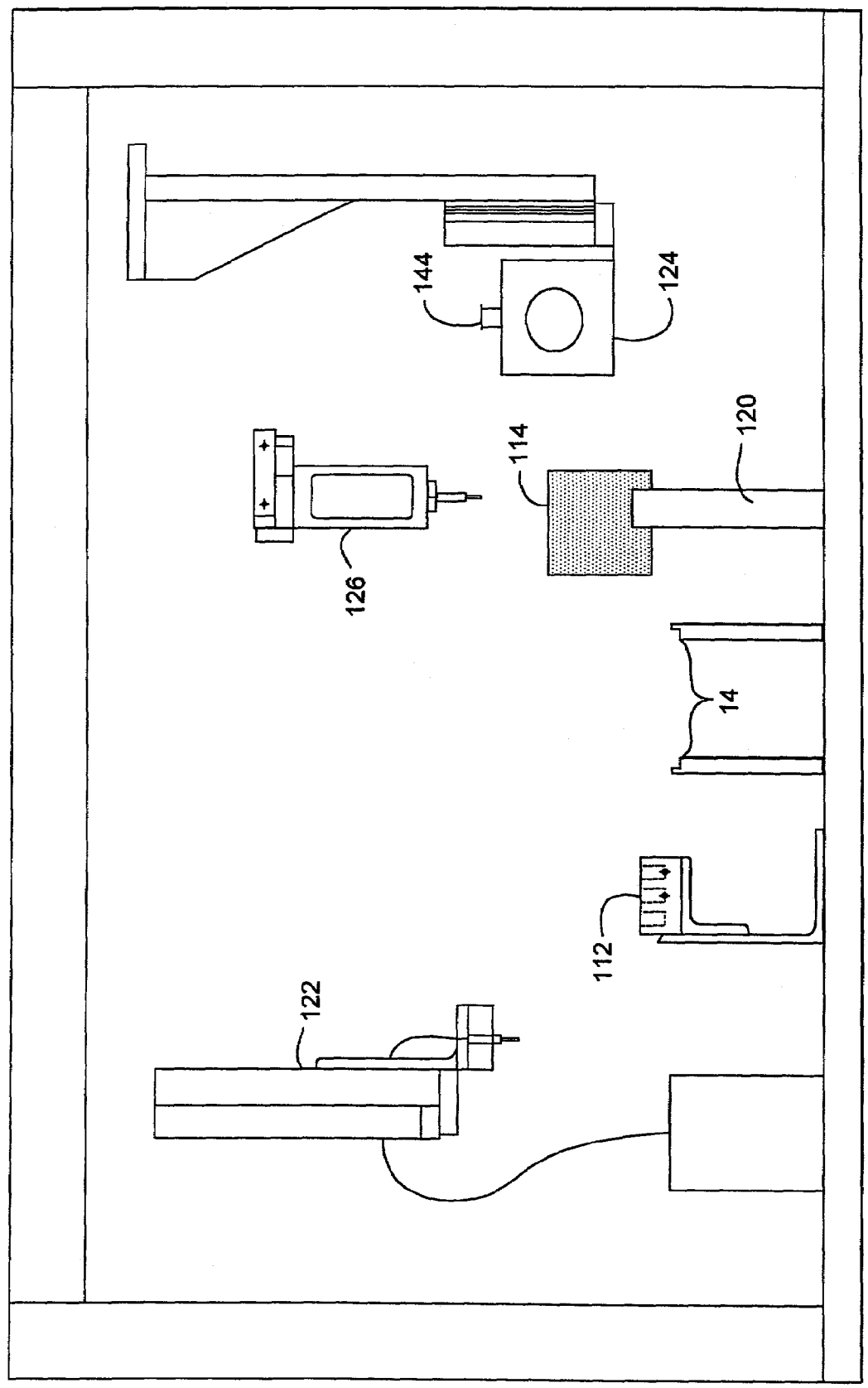
FIGS. 6A–6I illustrate operation of the drop formation station.

FIGS. 6A–6I illustrate a method for operating the drop formation station 28 to form hanging drops in each of the wells 38 of a multiwell plate 34. The figures are described with respect to crystallization of a protein, however, the same method can be used for crystallization of other types of molecules. FIG. 6A illustrates a drop formation station 28 in the rest position which can be occupied when the drop formation station 28 is not in use or between multiwell plates 34 being transported into the drop formation station 28. In the rest position, coverslips 144 are attached to the coverslip holder 124 which is positioned to one side of the plate track 14 and the pipette holder 122 is positioned to the opposing side of the plate track 14.

Figure 6B:
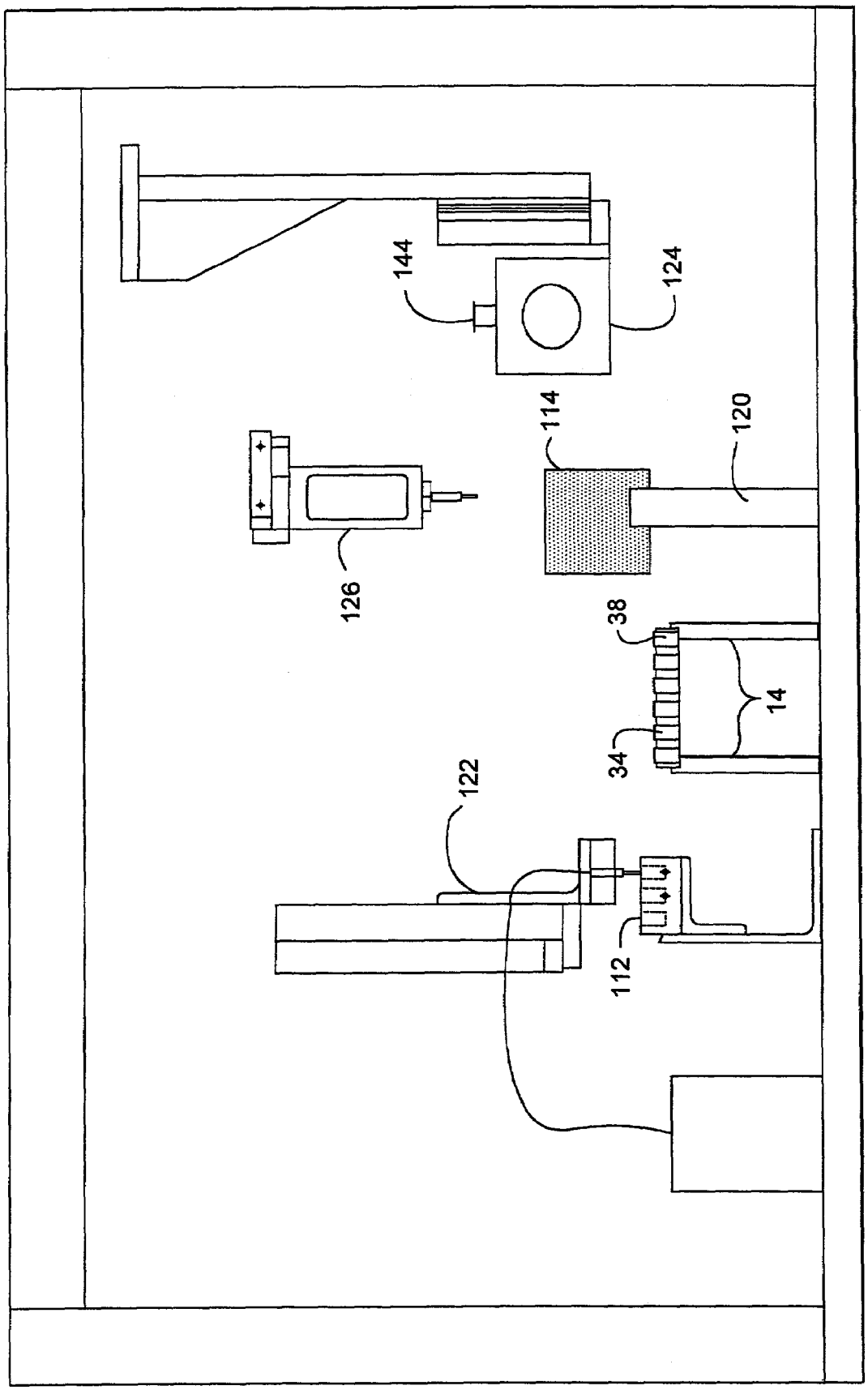

FIG. 6B illustrates a multiwell plate 34 moved into position for drop formation and the pipette holder 122 moved into position over the wash basin 112 for priming of the pipettes 130. The pipette holder 122 is lowered until the pipette tips are within a cleansing solutions within the wash basin 112. Cleansing fluid is aspirated from the wash basin 112 and the pipette holder 122 is raised to remove the pipette tips from the cleansing solution. The cleansing fluid is then expelled from the pipettes 130. The process of aspiration and expulsion can be repeated as often as is necessary to achieve a properly primed pipettes 130.

Figure 6C:
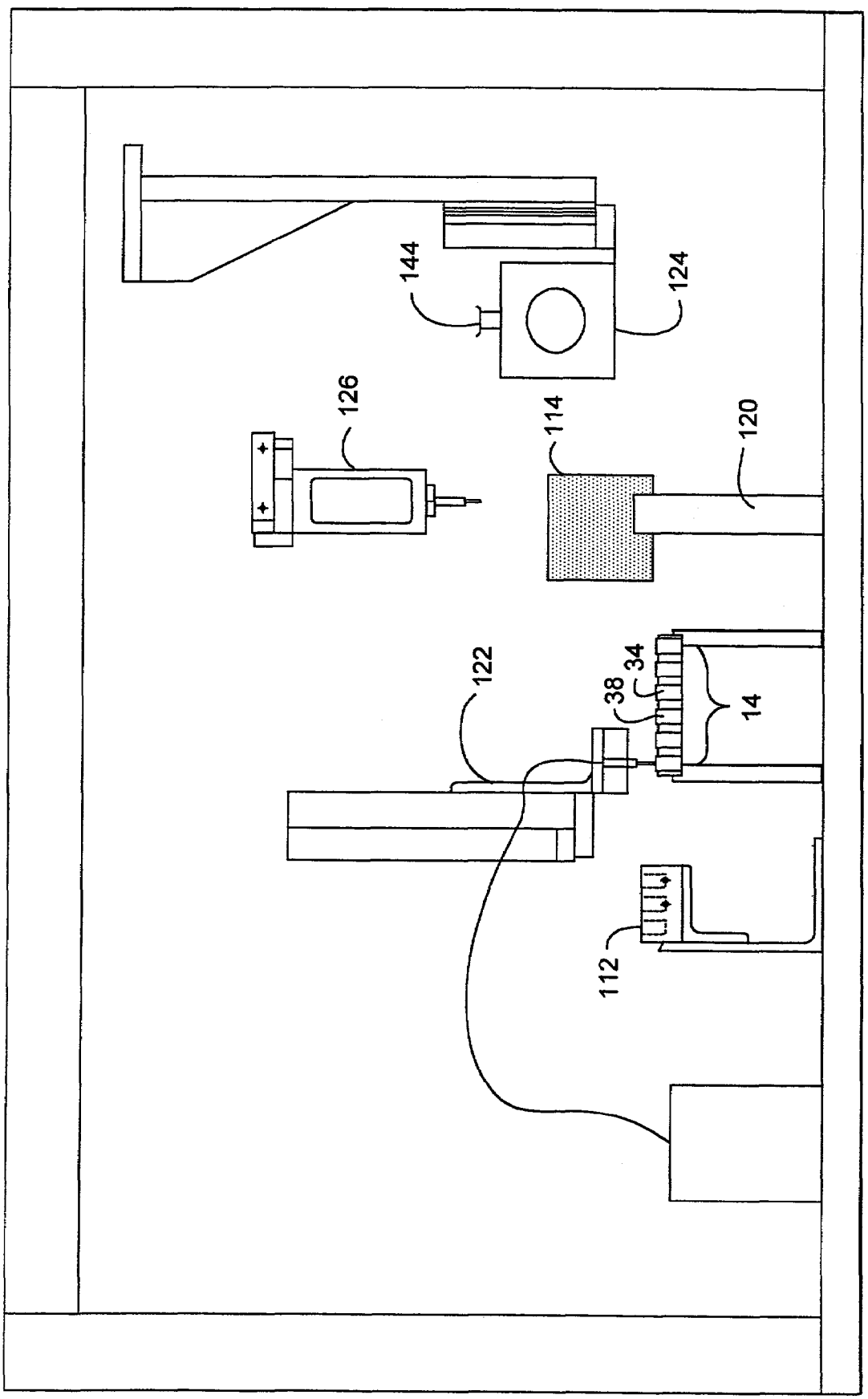

FIG. 6C illustrates the pipette holder 122 moved into position over a column of wells 38 in the plate 34. The pipette holder 122 is positioned so each pipette tip is aligned with a different well 38 in the column. Accordingly, each pipette 130 is associated with a particular well 38. The pipette holder 122 is lowered until each pipette tip is positioned within the mother liquor in the associated well 38. A portion of the mother liquor is aspirated from each well 38 associated with a pipette tip. The actuators then lift the pipettes 130 upward to remove the pipette tips from the wells 38. A portion of the aspirated mother liquors are then expelled from each pipette 130. The expelled mother liquors fall back into the associated well 38.

Figure 6D:
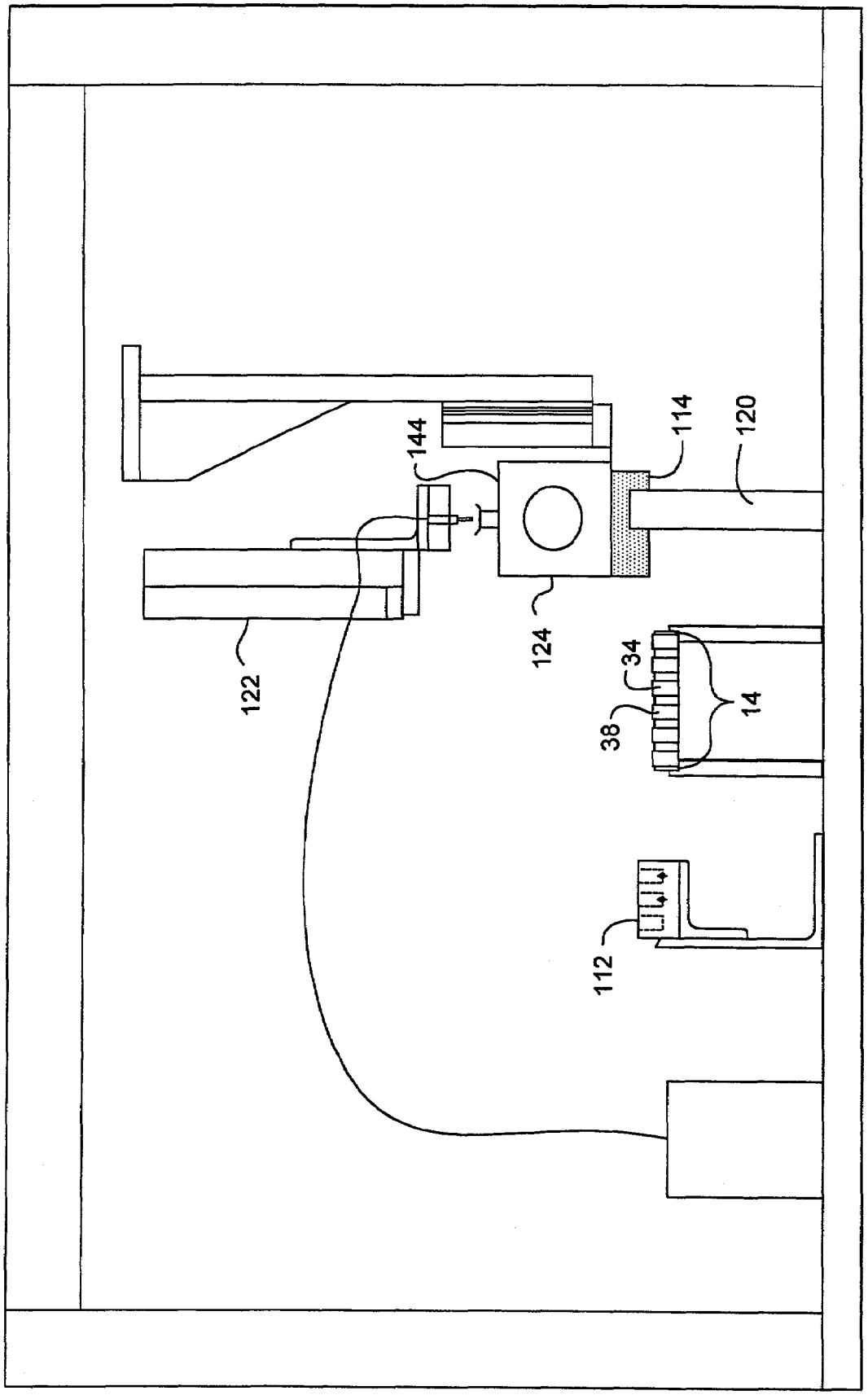

FIG. 6D illustrates the pipette holder 122 moved over the coverslip holder 124 and is positioned so each pipette tip is aligned with a different support cup 138. The support cups 138 are each holding a coverslip 144 upside down and the attachment mechanism 140 is engaged to immobilize the coverslips 144 relative to the support cups 138. One or more drops of mother liquor is expelled from each pipette 130 onto the associated coverslips 144. As a result, one more drops of the mother liquor from a particular well 38 is delivered onto a particular coverslip 144.

The drops of mother liquor are expelled onto the coverslips 144 until a desired volume of mother liquor has been delivered onto each coverslip 144. The total volume of the drops delivered onto the coverslips 144 is strictly controlled. As discussed previously, a feature of the present invention is the ability to deliver small volumes precisely which enables small drop volumes to be used. With devices which can deliver volumes as low as 380 pL, volumes can be delivered with great precision. The precision of the volumes delivered is preferably less than about 25 nL, more preferably less than 20 nL, more preferably less than 15 nL, and most preferably less than 10 nL. The precision of the volumes delivered may also be between 380 pL and 25 nL, more preferably between 380 pL and 20 nL, more preferably between 380 pL and 15 nL, and most preferably between 380 pL and 10 nL.

Figure 6E:
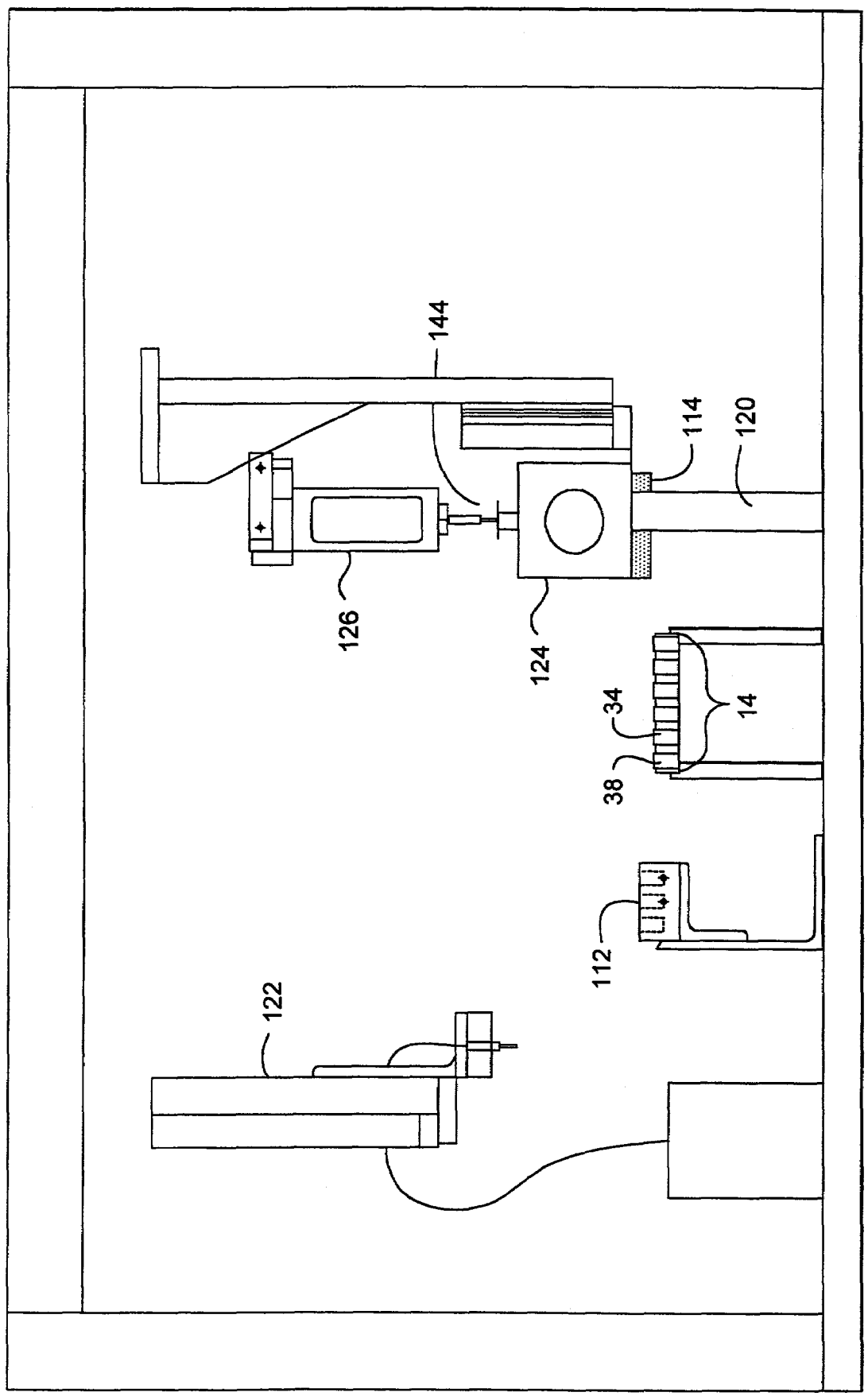

FIG. 6E illustrates the pipette holder 122 returned to the rest position which was illustrated in FIG. 6A. The molecule delivery pipette 126 is moved into position over a coverslip 144. Before being moved into position over the coverslip 144, the molecule delivery pipette 126 was lowered into a particular molecule solution well and a volume of the molecule solution aspirated. Once the molecule delivery pipette 126 is in position over the coverslip 144, drops of the molecule solution are delivered onto the mother liquor which was previously delivered onto the coverslip 144. The drops of molecule solution are delivered until a desired volume of molecule solution is achieved on the coverslip 144. The precision of the volumes delivered is preferably less than about 25 nL, more preferably less than 20 nL, more preferably less than 15 nL, and most preferably less than 10 nL. The precision of the volumes delivered may also be between 2 and 25 nL, more preferably between 2 and 20 nL, more preferably between 2 and 15 nL, and most preferably between 2 and 10 nL.

The mother liquor drops and the protein drops may be delivered in any order. Once both drops are delivered, the drops combine to form a hanging drop to be studied for crystal formation.

After forming a hanging drop on the coverslip 144, the molecule delivery pipette 126 proceeds to the next coverslip 144 until a hanging drop is formed on each coverslip 144. The molecule delivery pipette 126 then returns to the position over the molecule solution well which was the source for the molecule solution used to create the hanging drops. The molecule solution remaining in the molecule delivery pipette 126 is expelled into the molecule solution well.

Figure 6F:
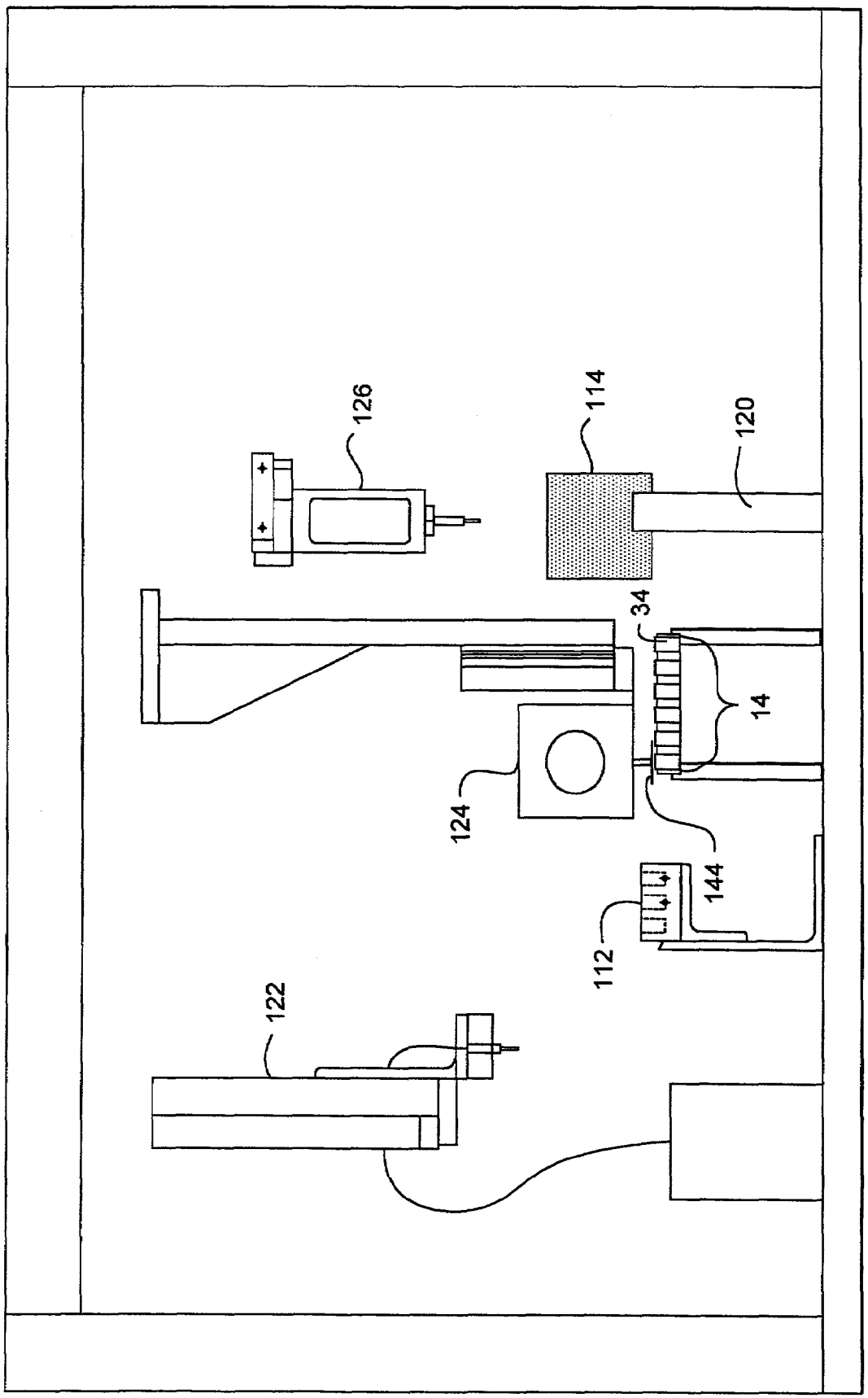

FIG. 6F illustrates the molecule delivery pipette 126 returned to its rest position as illustrated in FIG. 6A. FIG. 6F also illustrates the coverslip holder 124 inverted and moved into position over the column of wells 38 on the multiwell plate 34. The coverslip holder 124 is positioned so each coverslip 144 is aligned with a different well 38 in the column. Specifically, a given coverslip 144 is aligned with the well 38 which was the source of the mother liquor used to create the hanging drop on the given well 38.

Figure 6G:
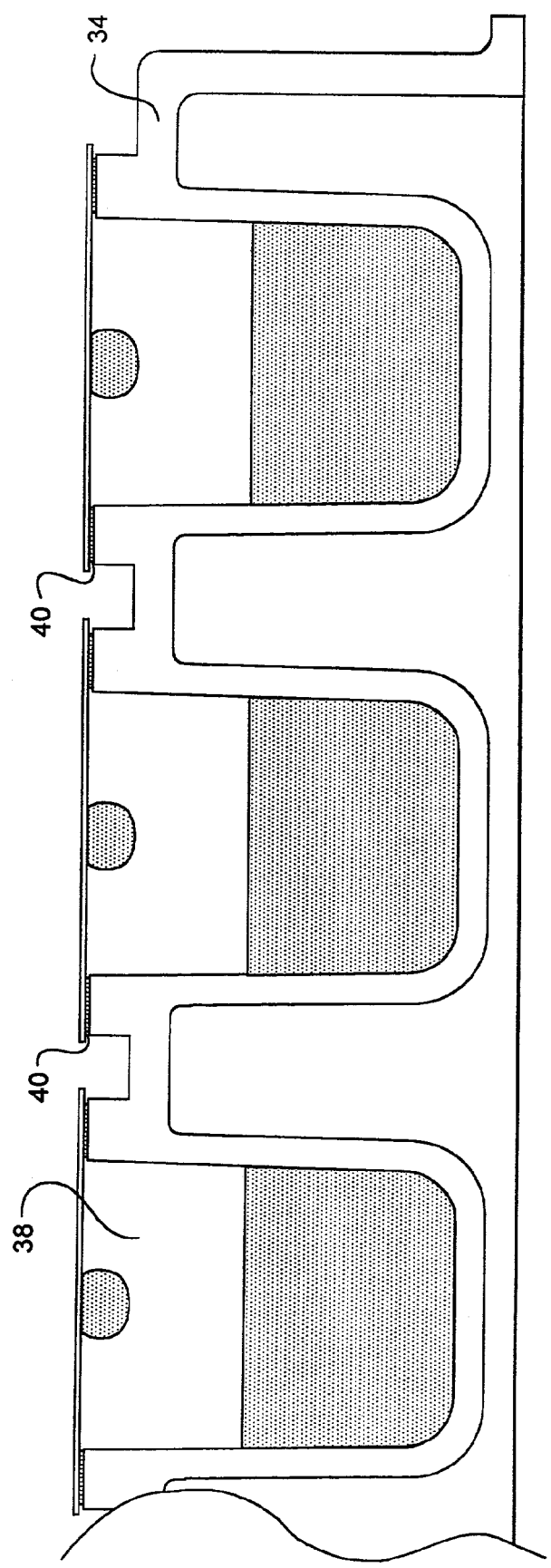

The coverslip holder 124 is lowered until the coverslips 144 contact the upper edges 40 of the associated wells 38. The sealing medium which was previously applied to the upper edge 40 of the wells 38 causes a seal to be formed between the coverslips 144 and the upper edges 40 of the associated wells 38. The attachment mechanism 140 is released and the coverslip holder 124 is raised to leave each coverslip 144 in place over an associated well 38. The hanging drop hangs from the coverslips 144 into the wells 38 as illustrated in FIG. 6G.

Figure 6H:
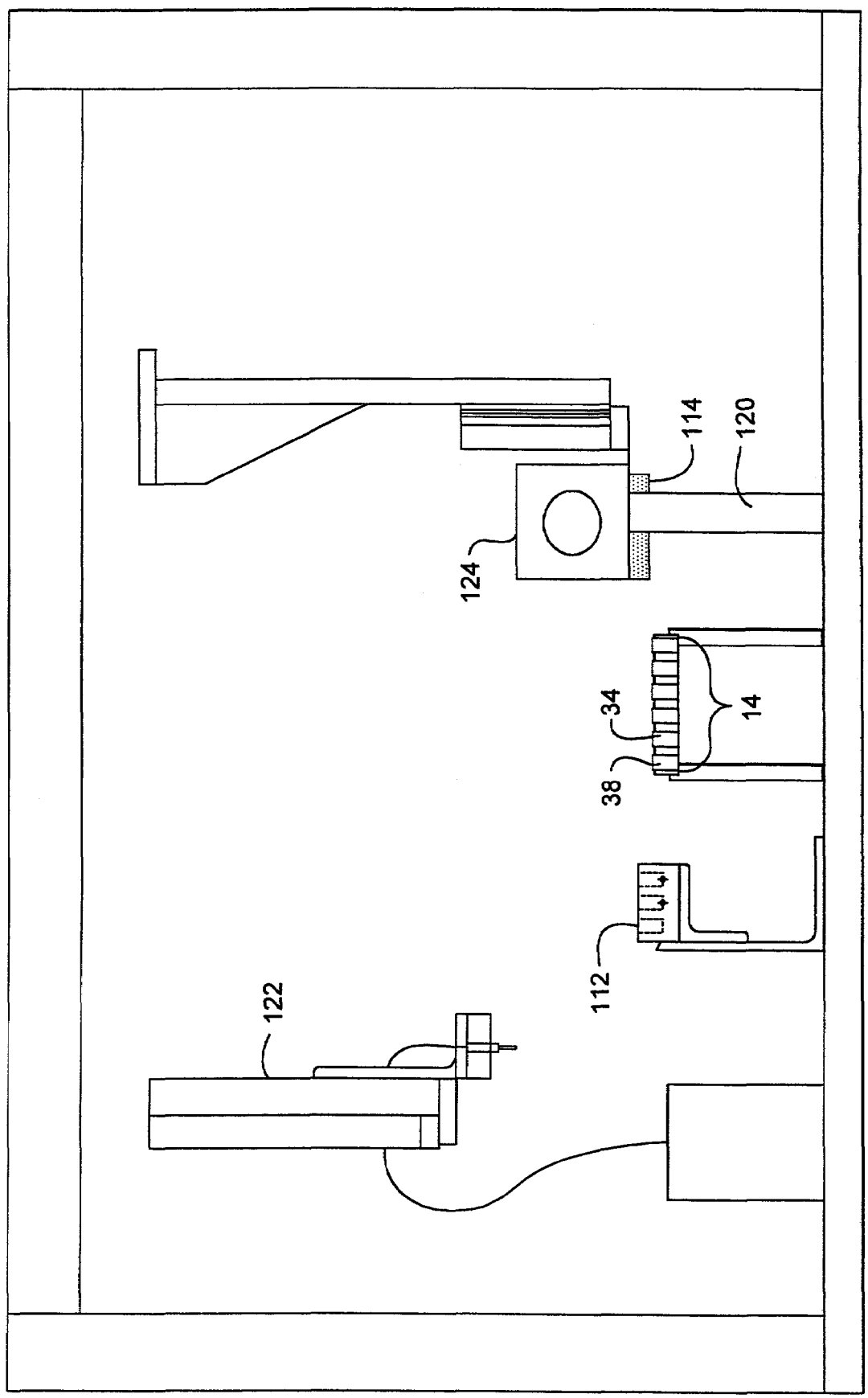

FIG. 6H illustrates the coverslip holder 124 moved into position over the coverslip storage component 120. The coverslip holder 124 is positioned so each support cup 138 is aligned with a magazine 142 in the coverslip storage component 120. Accordingly, each support cup 138 is associated with the top coverslip 144 in each magazine 142. The coverslip holder 124 is lowered until each support cup 138 contacts a coverslip 144 within the associated magazine 142. The attachment mechanism 140 is engaged to immobilize the contacted coverslips 144 relative to the associated support cups 138.

Figure 6I:
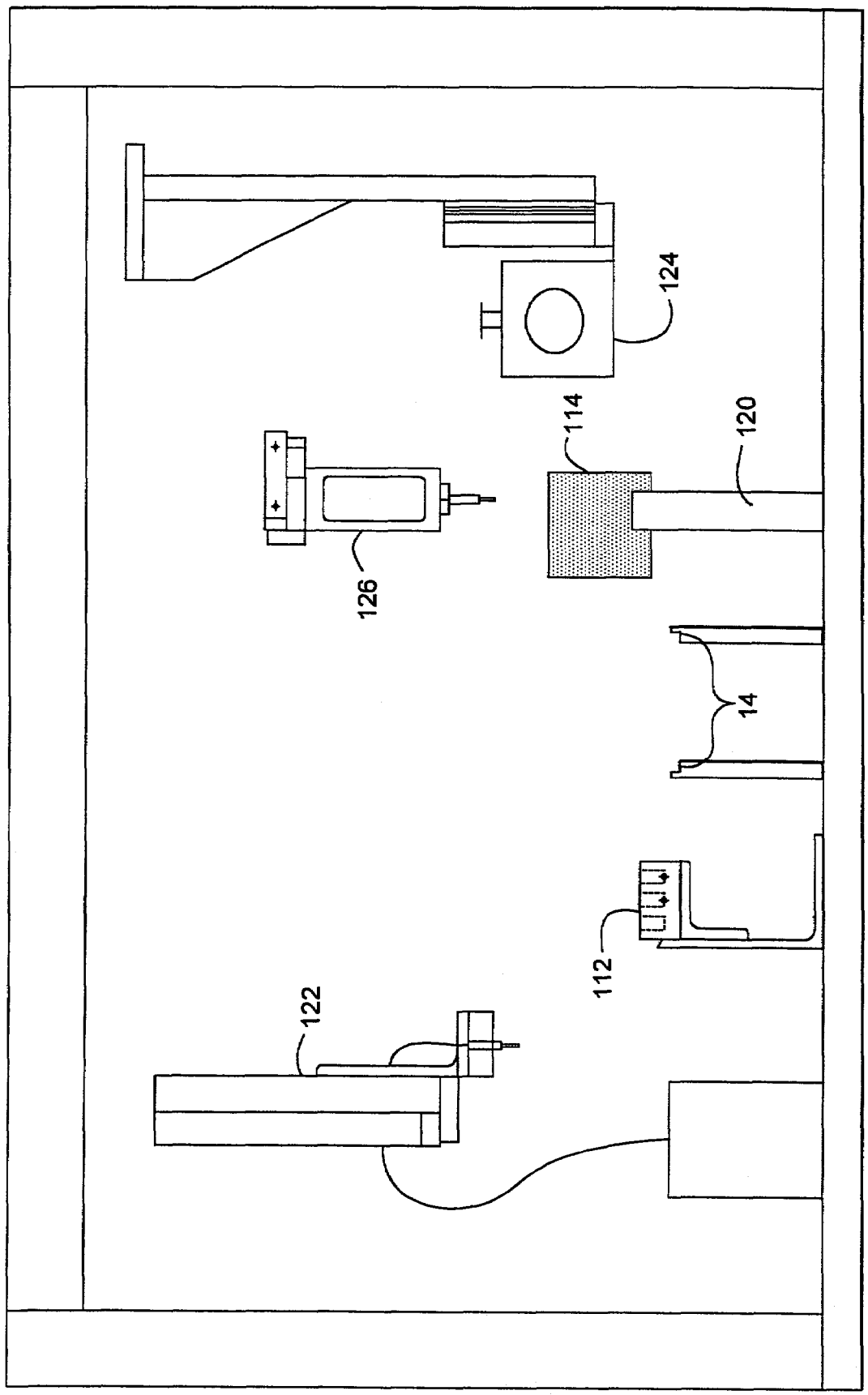

FIG. 6I illustrates the coverslip holder 124 returned to its rest position. The top coverslip 144 from each magazine 142 discussed with respect to FIG. 6G is attached to the associated support cup 138.

The steps described with respect to FIGS. 6A–6I result in a hanging drop being formed in each well 38 of a single column of wells 38. These steps are repeated until a hanging drop is formed in the wells 38 of each column of the multiwell plate 34. Once a hanging drop is formed in each of the wells 38, the multiwell plate 34 can be moved to the next station.

The crystallization system 10 described above can be adapted to form sitting drops. This adaptation can be made with changes to the mother liquor delivery station 26 and the drop formation station 28. For instance, the mother liquor delivery station 26 is adapted to deliver mother liquor into the well regions 41 of a multiwell plate 34 adapted to perform a sitting drop array microcrystallization such as the multiwell plate 34 illustrated in FIG. 3C. Specifically, the fluid injectors 88 of the mother liquor delivery station 26 must be aligned with the well regions 41 before the mother liquor is delivered into the wells 38 of the multiwell plate 34. This alignment permits delivery of the mother liquors into the well region 41 of each well .38 without delivering the mother liquors onto the sitting drop region 42 of each well 38.

Adapting the crystallization system 10 to form sitting drops also includes adapting the drop formation station 28 to form sitting drops. The drop formation station 28 can include each of the components illustrated in FIGS. 5A–5E arranged with the same spatial relationships illustrated in FIGS. 5A–5E. However, the method of operating these components varies from the method illustrated in FIGS. 6A–6I. FIGS. 7A–7G illustrate a method for operating the drop formation station 28 to form sitting drops in each well 38 of a multiwell plate 34 adapted to perform a sitting drop array micro crystallization.

Figure 7A:
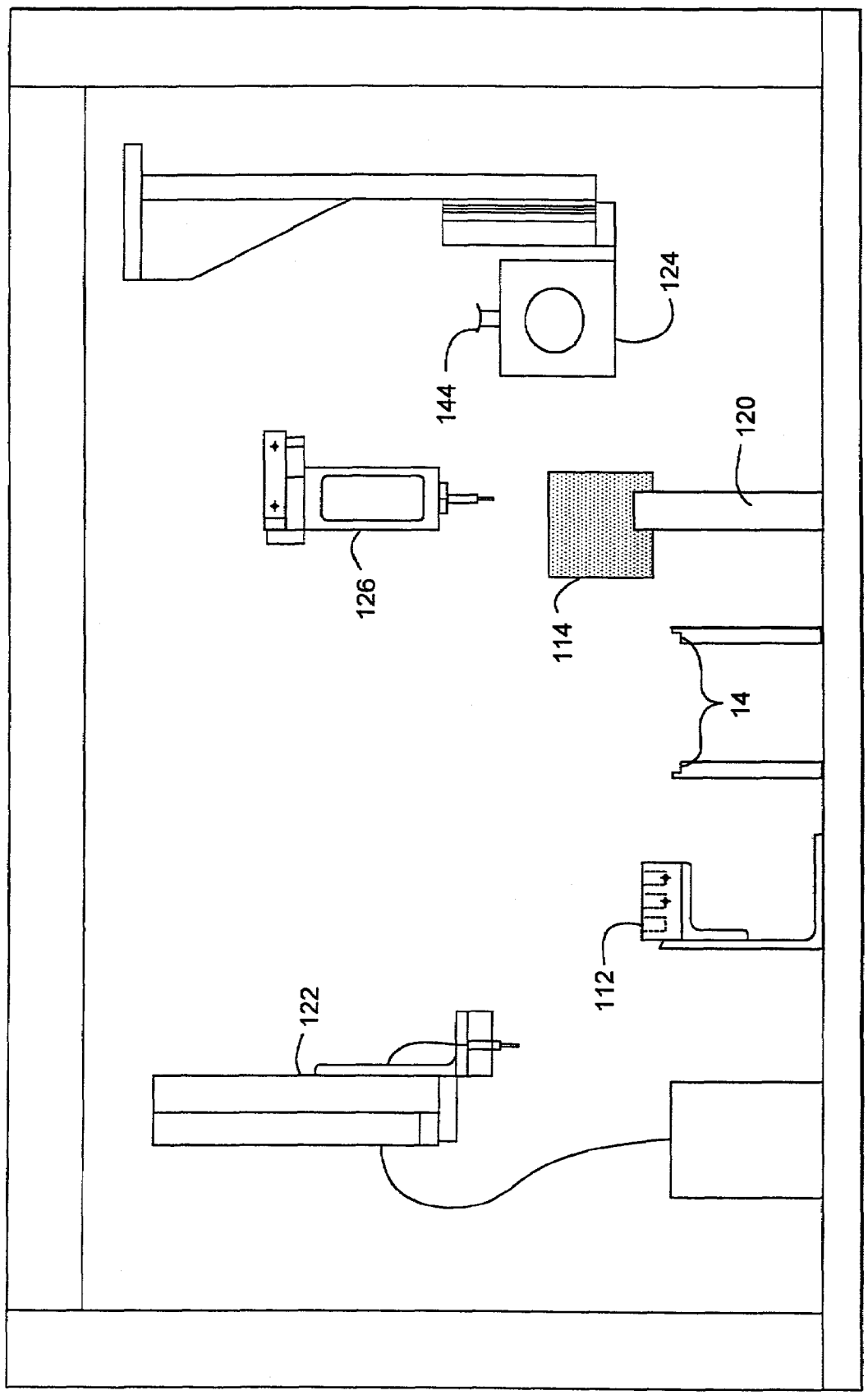
FIGS. 7A–7G illustrate operation of the drop formation station to form sitting drops.
Figure 7B:
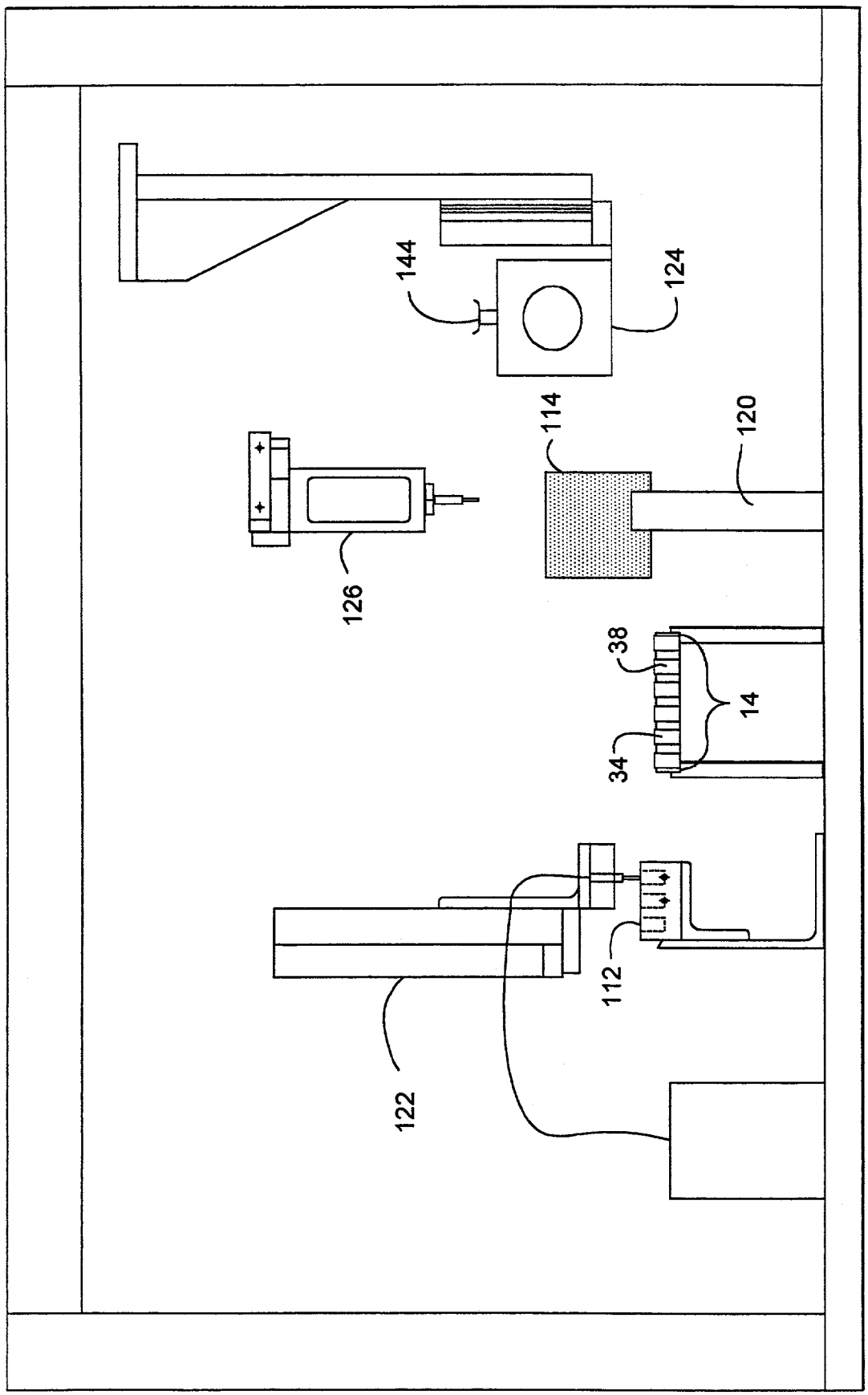

The figures are described with respect to crystallization of a protein, however, the same method can be used for crystallization of other types of molecules. FIG. 7A illustrates the drop formation station 28 in the same rest position illustrated in FIG. 6A. FIG. 7B illustrates a multiwell plate 34 adapted to perform a sitting drop array microcrystallization moved into position for sitting drop formation. Accordingly, each well 38 in the multiwell plate 34 includes a well region 41 adjacent to a sitting drop region 42. FIG. 7B also illustrates the pipette holder 122 moved into position over the wash basin 112 for priming of the pipettes. The pipettes are primed as described with respect to FIG. 6B.

Figure 7C:
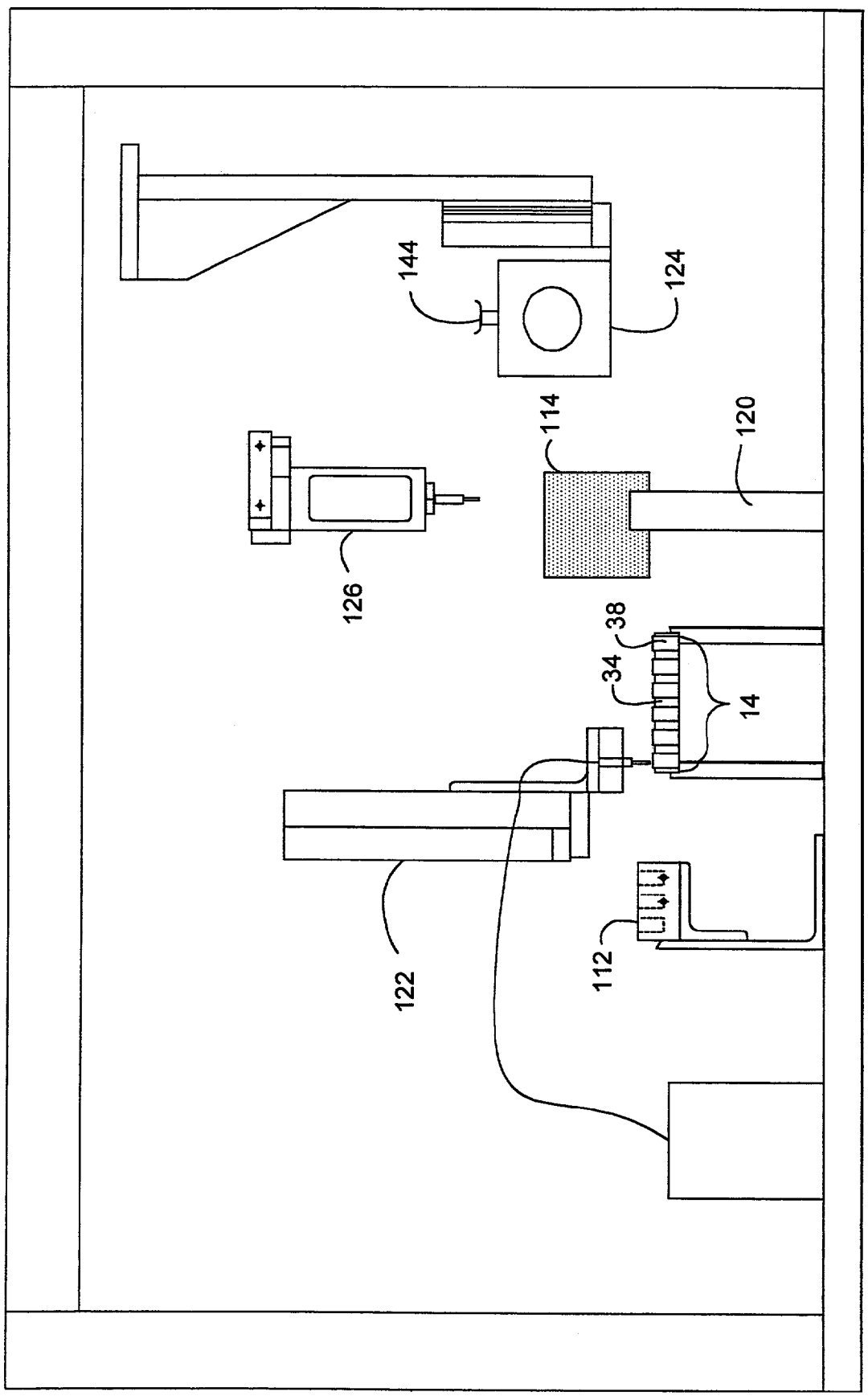
Figure 7D:
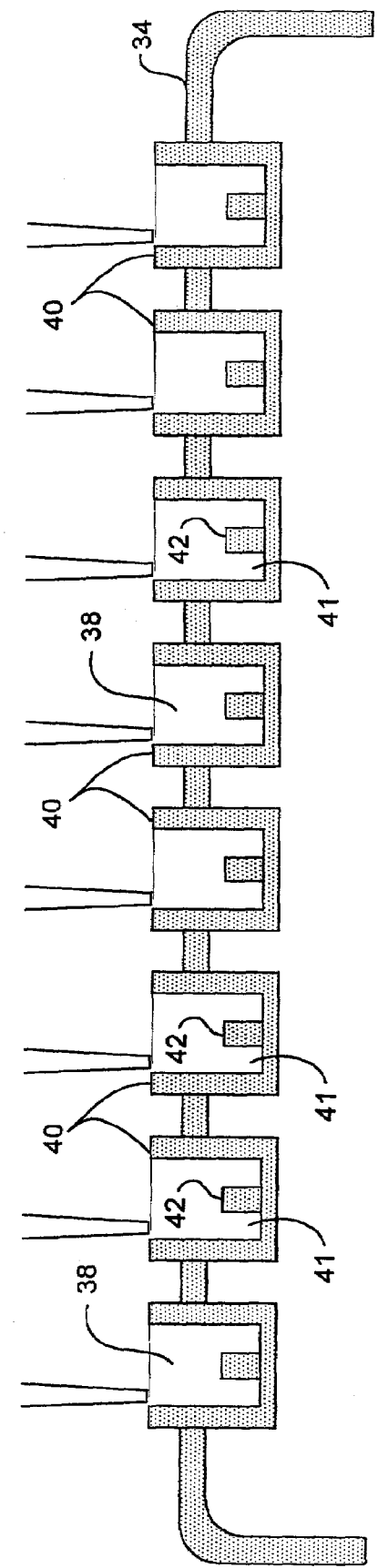

FIG. 7C illustrates the pipette holder 122 moved into position over a column of wells 38 in the multiwell plate 34. The pipette holder 122 is positioned so each pipette tip is aligned with the well region 41 in a different well 38 in the column as illustrated in FIG. 7D. Accordingly, each pipette is associated with a particular well 38. The pipette holder 122 is lowered until the tip of each pipette is positioned in the mother liquor which was previously delivered into the well region 41 of the associated well 38. A portion of the mother liquor is aspirated from each well region 41 associated with a pipette tip. The actuators then lift the pipette upward to remove the pipette tips from the wells 38. A portion of the aspirated mother liquors are then expelled from each pipette. The expelled mother liquors fall back into the associated well regions 41.

Figure 7E:
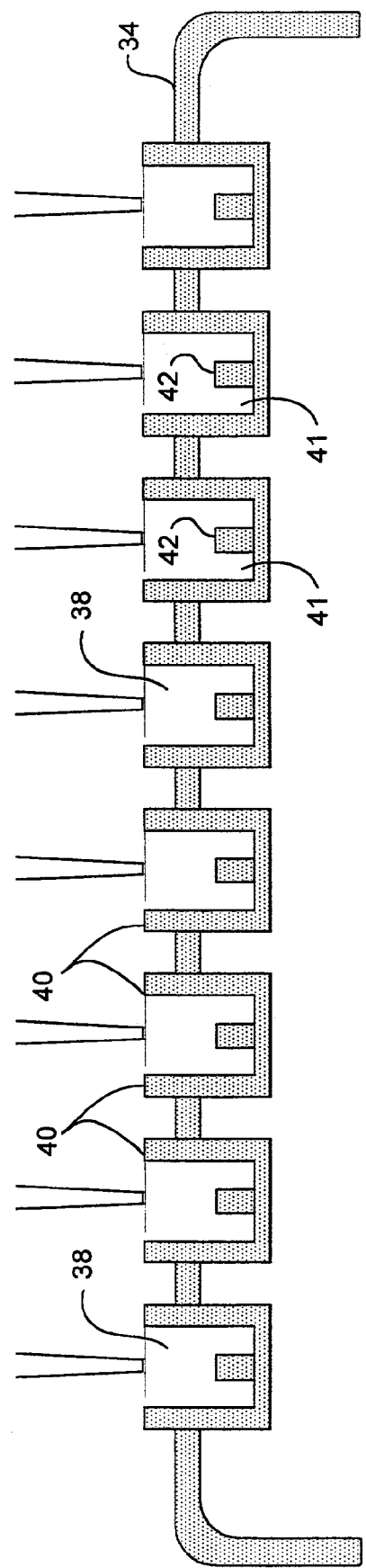

The pipette holder 122 is then moved so each pipette tip is aligned with the sitting drop region 42 in a different well 38 in the column as illustrated in FIG. 7E. One or more drops of mother liquor is expelled from each pipette onto the associated sitting drop region 42. As a result, one more drops of the mother liquor from a particular well region 41 is delivered onto the sitting drop region 42 of the same well 38. The drops of mother liquor are expelled onto the sitting drop region 42 until a desired volume of mother liquor has been delivered onto each sitting drop region 42. The total volume of the drops delivered onto the coverslips 144 is strictly controlled. As discussed previously, a feature of the present invention is the ability to deliver small volumes precisely which enables small drop volumes to be used. With devices which can deliver volumes as low as 380 pL, volumes can be delivered with great precision. The precision of the volumes delivered is preferably less than about 25 nL, more preferably less than 20 nL, more preferably less than 15 nL, and most preferably less than 10 nL. The precision of the volumes delivered may also be between 380 pL and 25 nL, more preferably between 380 pL and 20 nL, more preferably between 380 pL and 15 nL, and most preferably between 380 pL and 10 nL.

Figure 7F:
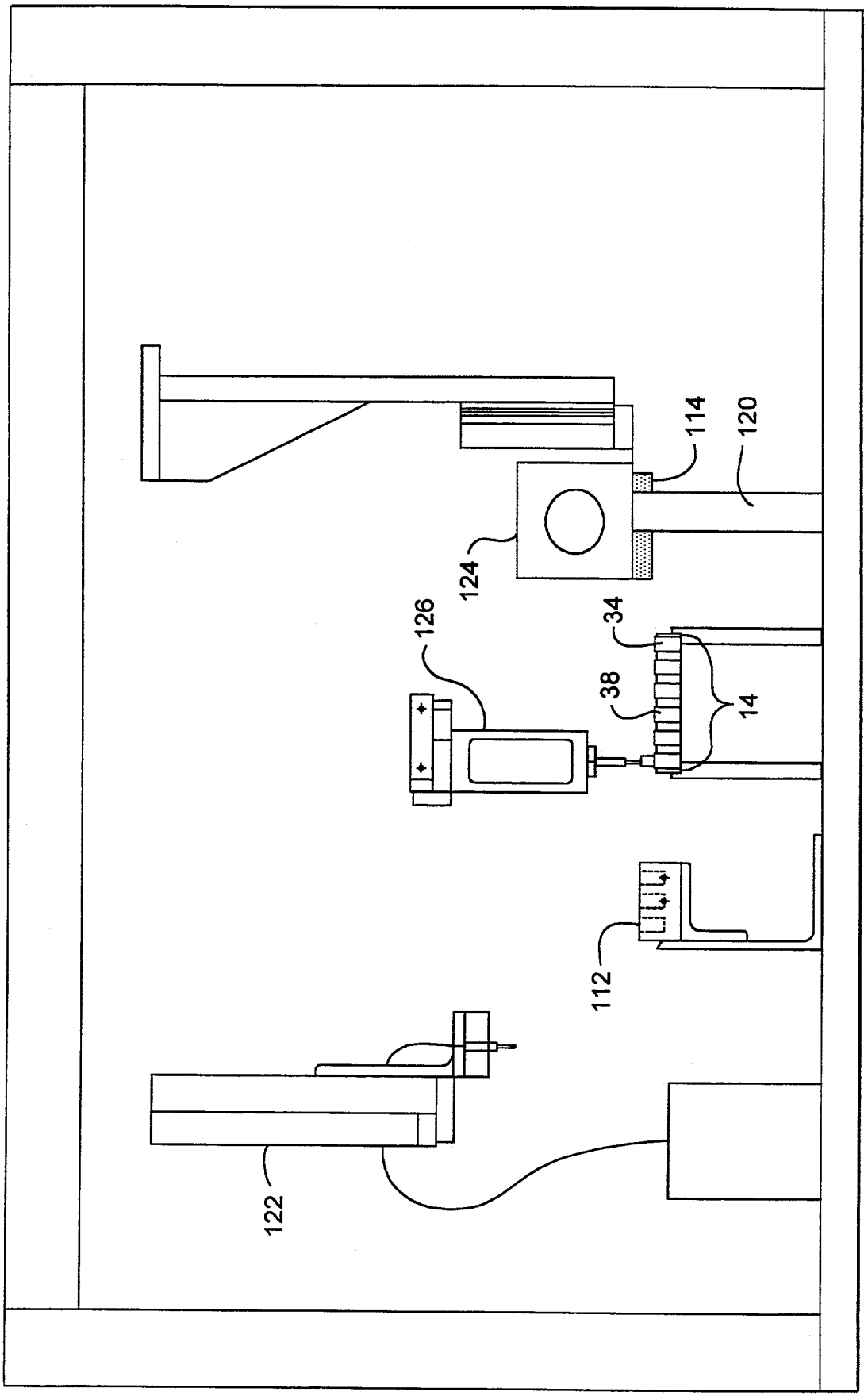

FIG. 7F illustrates the pipette holder 122 returned to the rest position which was illustrated in FIG. 7A. The molecule delivery pipette 126 is moved into position over a sitting drop region 42 in a well 38 of the column. Before being moved into position over the well 38, the molecule delivery pipette 126 was lowered into a particular molecule solution well and a volume of the molecule solution aspirated. Once the molecule delivery pipette 126 is in position over the sitting drop region 42, drops of the molecule solution are delivered onto the mother liquor which was previously delivered onto the coverslip 144. The drops of molecule solution are delivered until a desired volume of molecule solution is achieved on the sitting drop region 42. The precision of the volumes delivered is preferably less than about 25 nL, more preferably less than 20 nL, more preferably less than 15 nL, and most preferably less than 10 nL. The precision of the volumes delivered may also be between 380 pL and 25 nL, more preferably between 380 pL and 20 nL, more preferably between 380 pL and 15 nL, and most preferably between 380 pL and 10 nL.

Figure 7G:
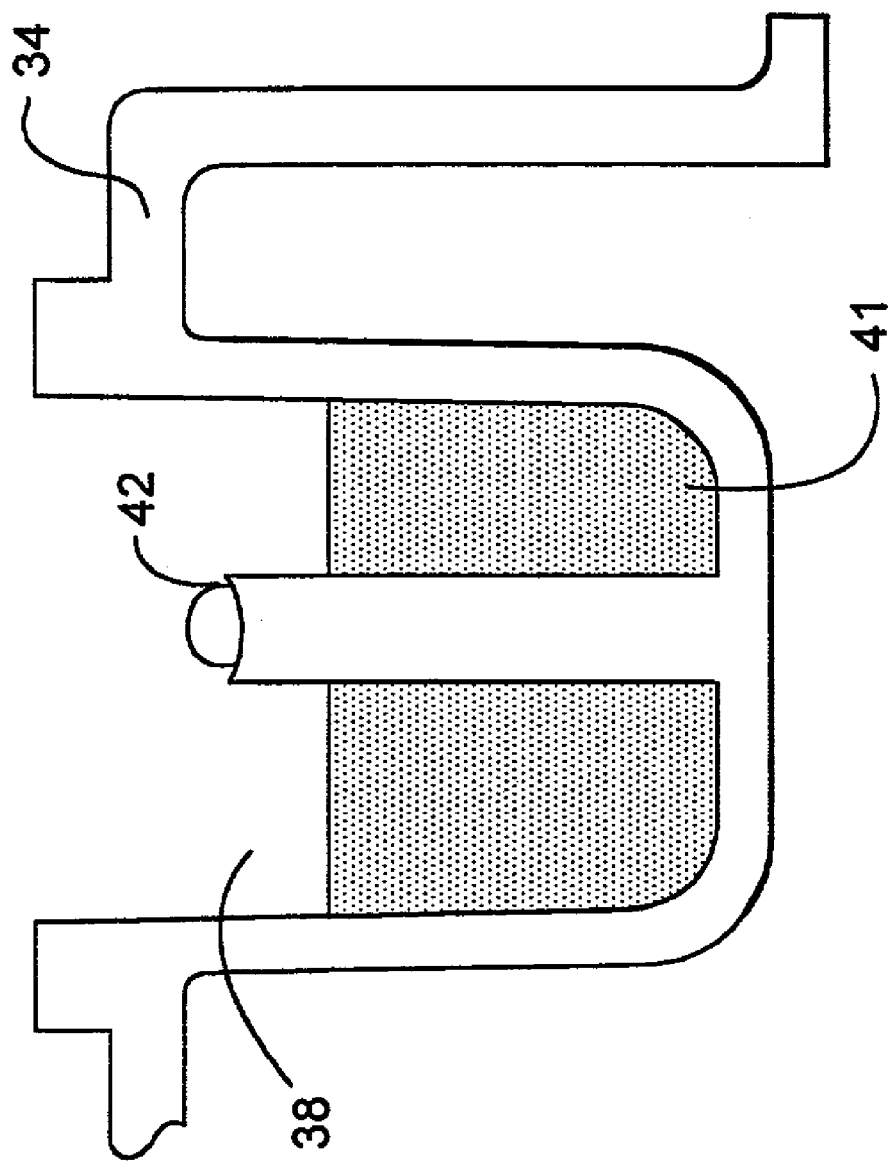

The mother liquor drops and the protein drops may be delivered in any order. Once both drops are delivered, the drops combine to form a sitting drop to be studied for crystal formation. FIG. 7G illustrates a sitting drops formed on the sitting drop region 42 of a well 38. After forming the sitting drop on the sitting drop region 42, the molecule delivery pipette 126 proceeds to the sitting drop region 42 in the next well 38 until a sitting drop is formed in each well 38 of the column. The molecule delivery pipette 126 then returns to the position over the molecule solution well which was the source for the molecule solution used to create the sitting drops. The molecule solution remaining in the molecule delivery pipette 126 is expelled into the molecule solution well.

After formation of the sitting drop, the coverslips 144 are positioned over the wells 38 having sitting drops, new cover slips are loaded onto the coverslip holder 124 and the drop formation station 28 is returned to the rest position as described above with respect to FIGS. 6F–6I.

The steps described with respect to FIGS. 7A–7G result in a sitting drop being formed in each well 38 of a single column of wells 38. These steps are repeated until a hanging drop is formed in the wells 38 of each column of the multiwell plate 34. Once a hanging drop is formed in each of the wells 38, the multiwell plate 34 can be moved to the next station.

Although FIGS. 6A–7G illustrate a method for operating the drop formation station to form sitting drops and hanging drops, the hanging drop station be easily adapted to other crystallization techniques, other well geometries and/or other multiwell plate geometries.

It is noted that the apparatuses described in regard to FIGS. 6A–7G may optionally include one or more sensors which can detect whether mother liquor drops and/or molecule drops have been formed. An example of a suitable sensor is a LED sensor.

Figure 8A:
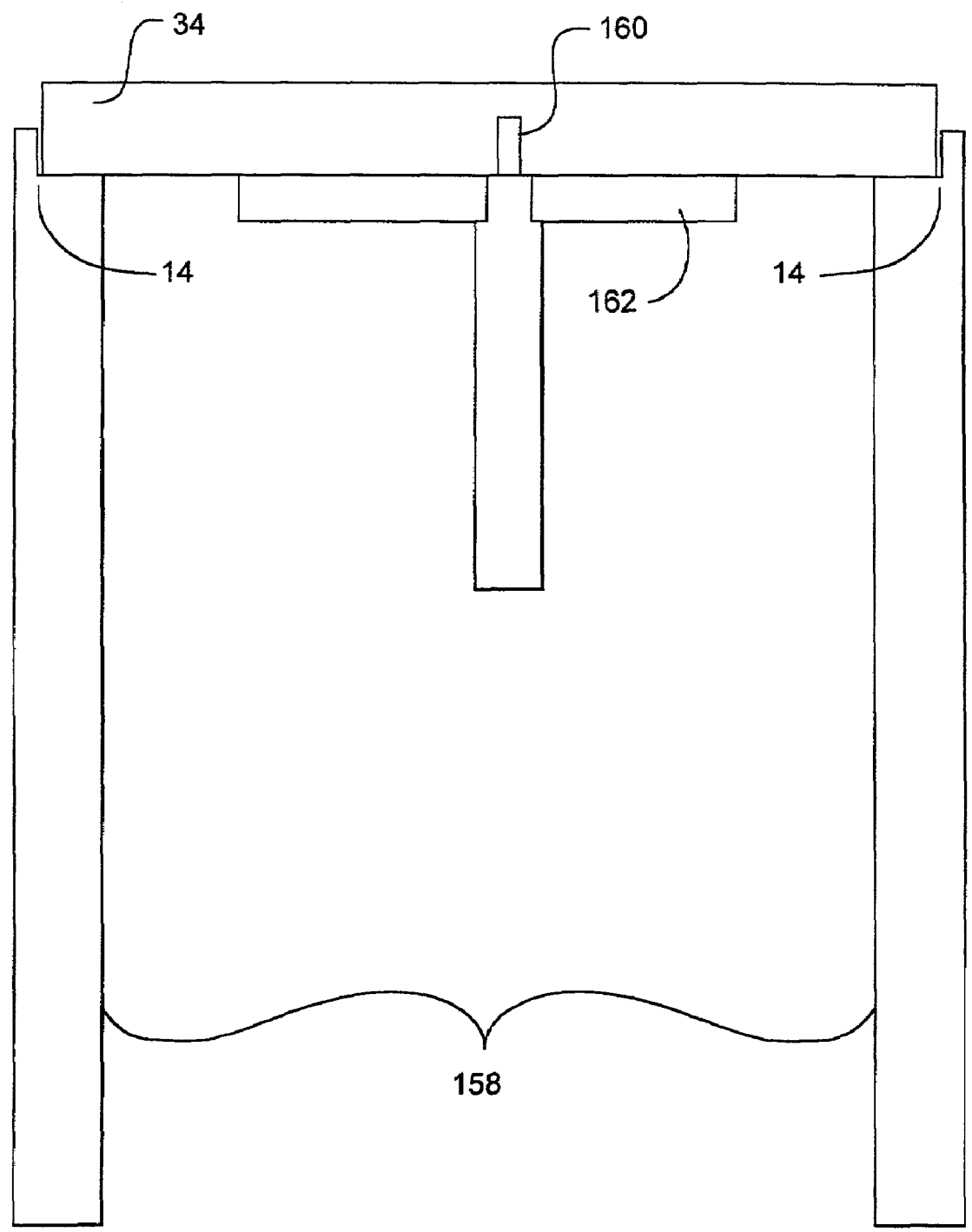
FIG. 8A is a sideview of a plate track with a pin extending above the plate track from a pin carriage positioned beneath the plate track.
Figure 8B:
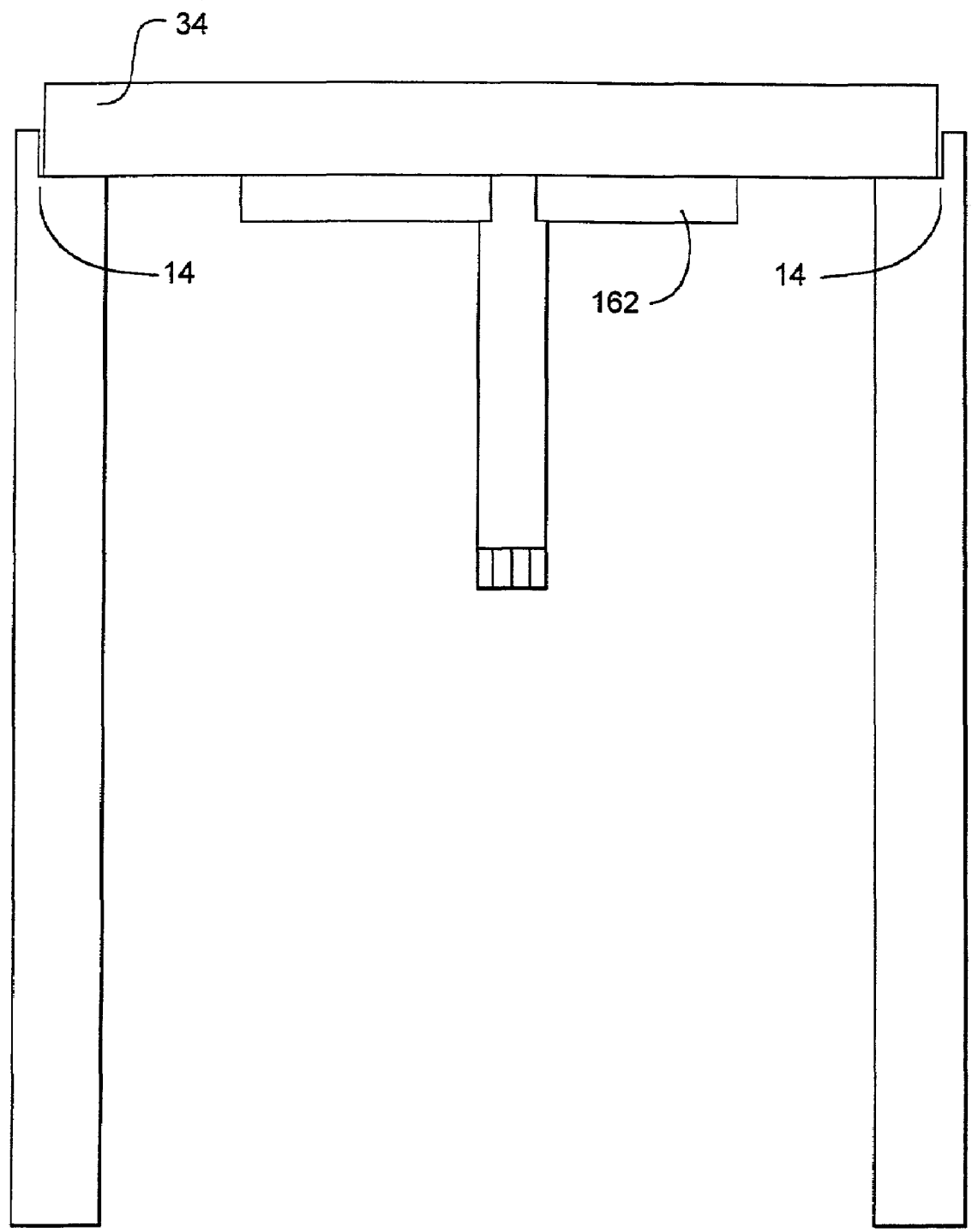
FIG. 8B is a sideview of a plate track with a pin of FIG. 8A withdrawn beneath the plate track.
Figure 8C:
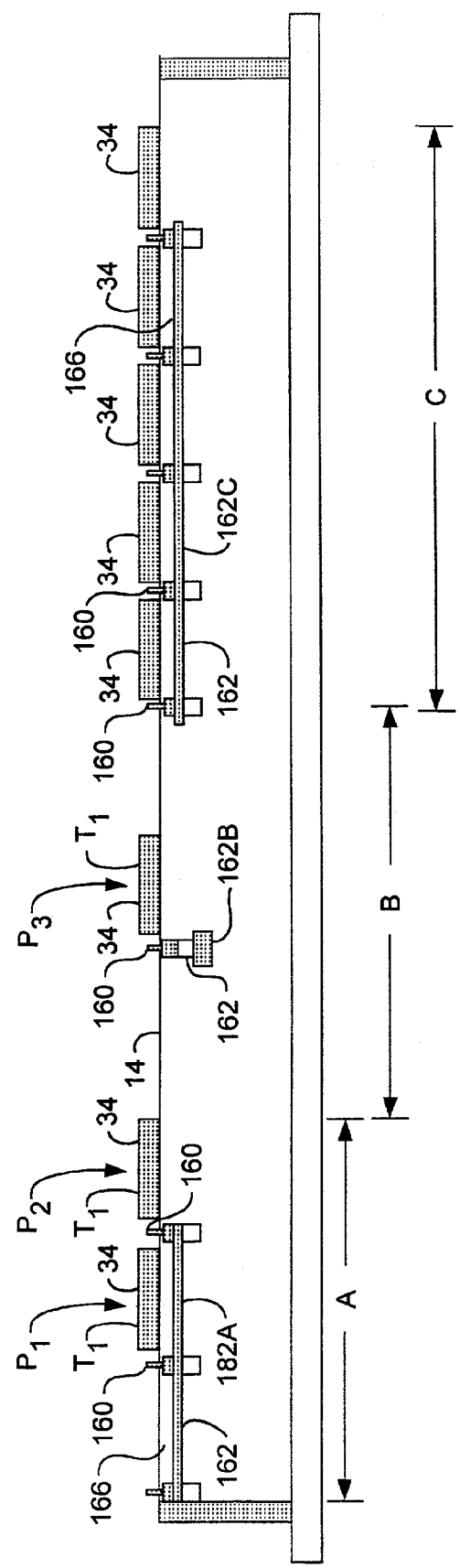
FIG. 8C is a sideview of a transport assembly having a plurality of pin carriages.
Figure 10A:
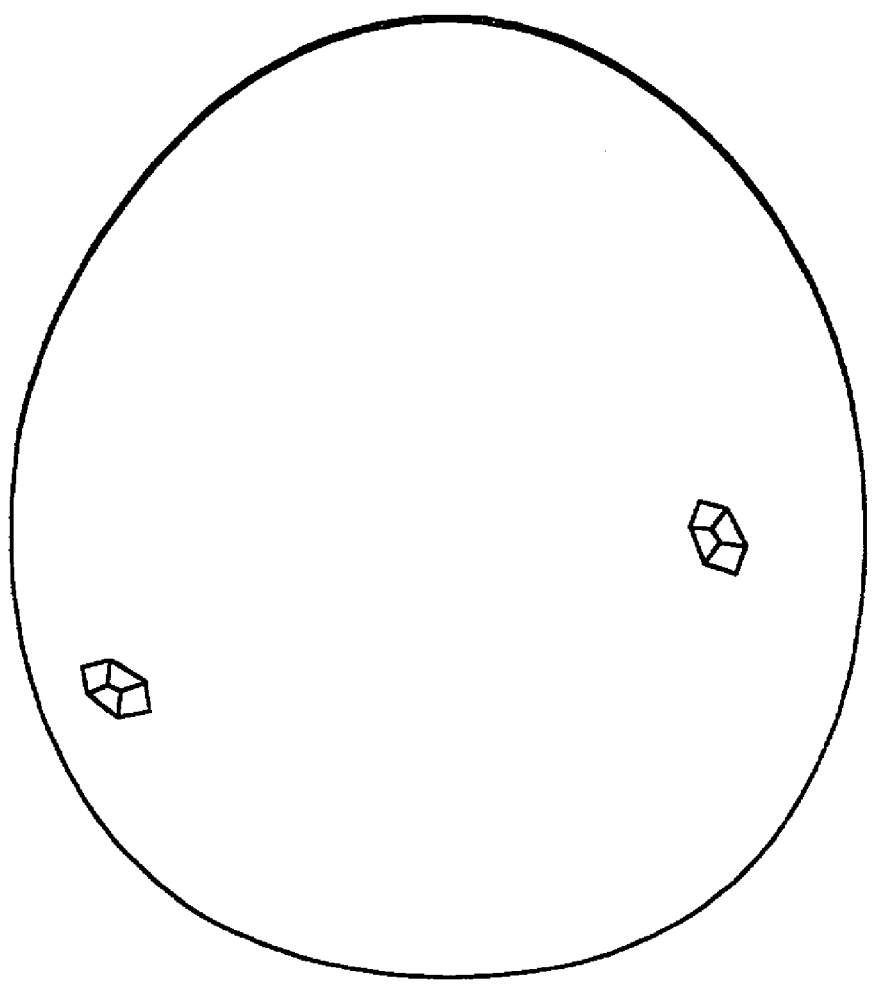
FIGS. 10A–10D illustrate formation of crystals in different drops sized from 40 nL to 1000 nL.
Figure 10B:
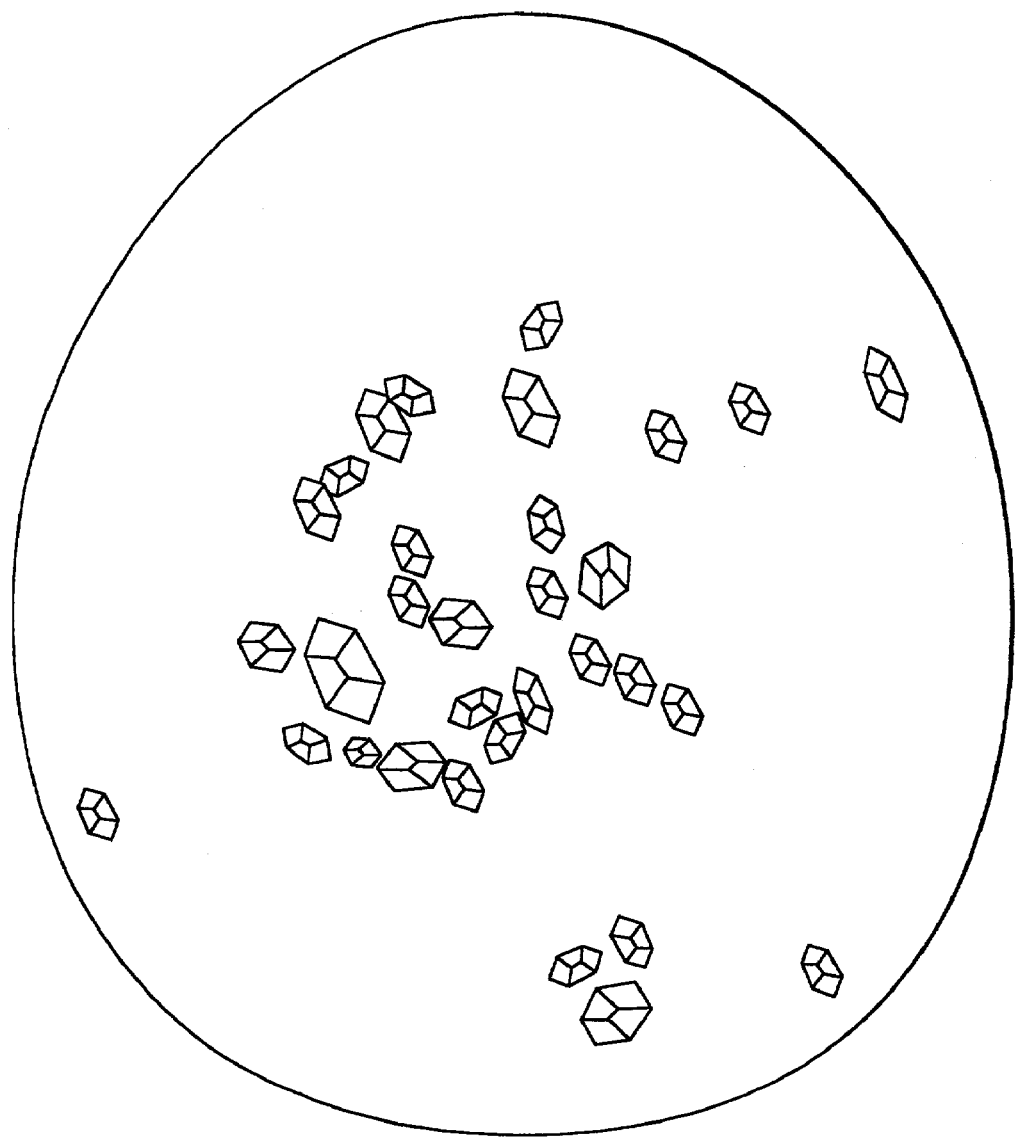
Figure 10C:
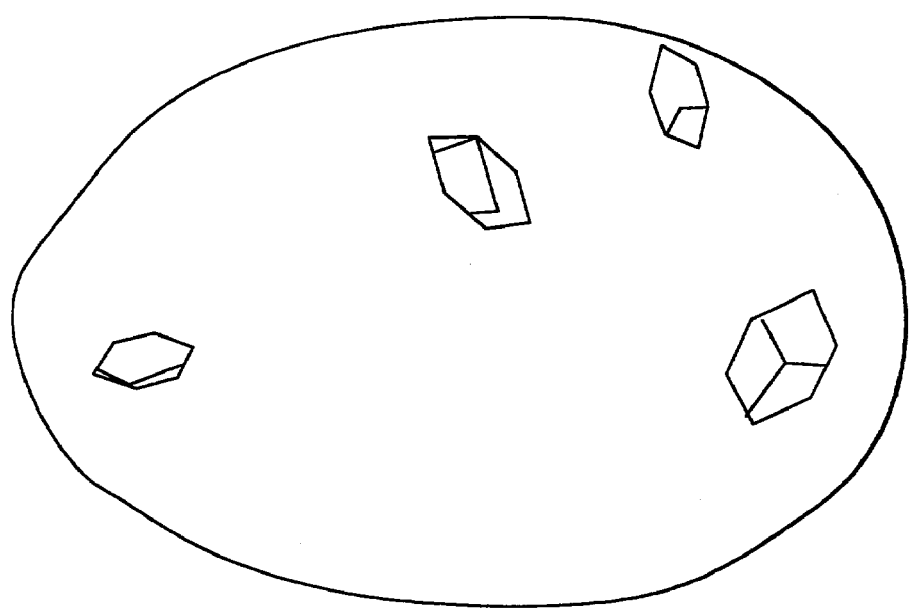
Figure 10D:
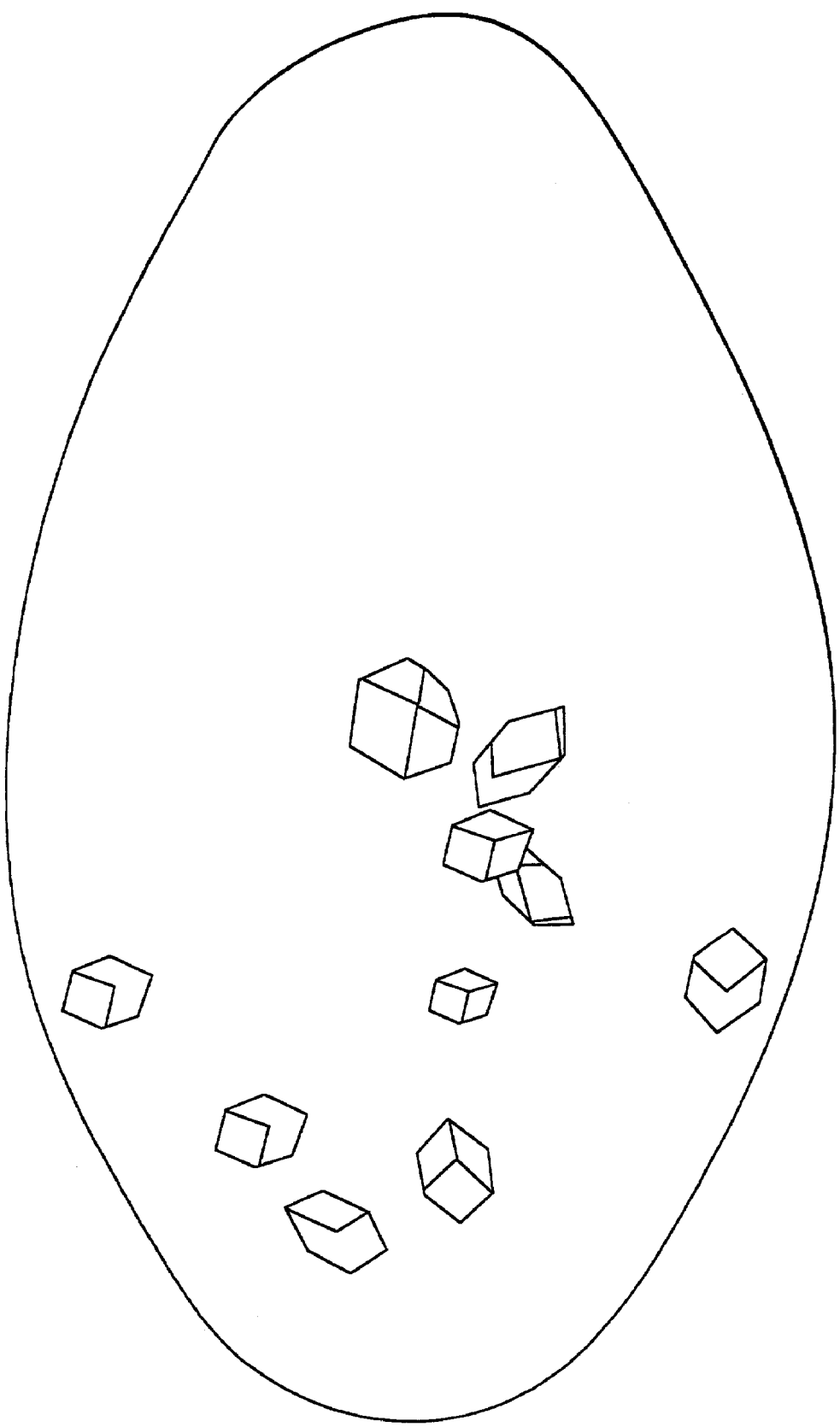

While many plate tracks 14 and transport assemblies can be used with the above stations 12, FIGS. 8A–8C illustrate a preferred embodiment of a plate track 14 for transporting multiwell plates 34 between the above stations 12. FIGS. 8A and 8B are sideviews of a plate track 14 looking down the longitudinal axis of the plate track 14. The plate track 14 includes two spaced apart plate supports 158. A pin 160 extends upward from a pin carriage 162 positioned beneath the plate track 14. The carriage includes mechanics which can be actuated to extend the pin 160 above the plate track 14 as illustrated in FIG. 8A or to withdraw the pin 160 below the plate track 14 as illustrated in FIG. 8B.

FIG. 8C is a lateral sideview of a plate track 14 and transport assembly with a plurality of multiwell plates 34 present on the plate track 14. The transport assembly includes a first pin carriage 162A, a second pin carriage 162B and a third pin carriage 162C. Each of the pin carriages 162A, 162B, 162C is configured to move along the longitudinal axis of the plate track 14 as illustrated by the arrows labeled A, B and C. The brackets at the ends of the arrows indicate the range of motion of each pin carriage 162A, 162B, 162C.

The first pin carriage 162A and the third pin carriage 162C include a plurality of pins 160. The pins are located along the pin carriage 162A, 162C with an approximately constant displacement between adjacent pins 160. The pin carriage 162A, 162C serves to maintain the displacement between the pins 160 during movement of the pin carriage 162A, 162C.

Each pin 160 is illustrated in the extended position, however, the pins in one pin carriage 162 can be withdrawn while the pins 160 in another pin carriage 162 are extended. In another embodiment, a portion of the pins 160 in a single pin carriage 162 can be extended while another portion of the pins 160 within the same pin carriage 162 are withdrawn.

An air gap 166 is formed between the pin carriages 162A, 162B, 162C and each of the multiwell plates 34 positioned on the plate track 14 so the pin carriages 162A, 162B, 162C do not contact the bottom surface of the multiwell plates 34. As a result, when the pins 160 are withdrawn, the pin carriages 162A, 162B, 162C can be moved along the longitudinal axis of the plate track 14 without moving multiwell plate 34 on the plate track 14. When the pin 160 is extended and the pin carriage 162 is moved along the longitudinal axis of the plate track 14, the pin 160 pushes any multiwell plate 34 obstructing the pin's travel along the longitudinal axis of the plate track 14.

As described above, the plate transport assembly is used to transport the multiwell plates 34 from station to station along the plate track 14. Various positions along the plate track 14 can be associated with a particular station of the crystallization system 10. For instance, when a multiwell plate 34 is located at position $P_1$, a bar code on the multiwell plate 34 can be read by a bar code station and when a multiwell plate 34 is located at position $P_2$, a sealing medium station 22 can be used to apply a sealing medium to the upper edge 40 of the wells 38 of the multiwell plate 34.

Further, when a multiwell plate 34 is positioned at $P_3$, the multiwell plate 34 can be positioned beneath one of the delivery shuttles 74 of a mother liquor delivery station 26.

The following description describes a method for using the above transport assembly for advancing the multiwell plate 34 labeled $T_1$, from the position labeled $P_1$ to the position labeled $P_2$ to the position labeled $P_3$. Once the multiwell plate $T_1$ is located at position $P_1$, the pins 160 in the first pin carriage 162A are withdrawn below the plate track 14. The first pin carriage 162A is then moved to the left and the pins 160 extended above the plate track 14 as illustrated in FIG. 8C. The multiwell plate $T_1$ can then be moved from position $P_1$ to position $P_2$ by moving the first pin carriage 162A to the right until the multiwell plate $T_1$ is positioned at position $P_2$. The pins 160 are then withdrawn below the plate track 14 and the first pin carriage 162A is moved back to is original position and the pins 160 are again extended above the plate track 14. The pins 160 in the second pin carriage 162B are withdrawn below the plate track 14 and the second pin carriage 162B is moved to the left of the multiwell plate $T_1$. The pins 160 in the second pin carriage 162B are then extended above the plate track 14 and the second pin carriage 162B moved to the right until the multiwell plate $T_1$ is located at position $P_3$.

The plurality of pin carriages 162 illustrated in FIG. 8C allows a multiwell plate 34 at one station to be processed through the crystallization system 10 independently of another multiwell plate 34 being processed through the crystallization system 10. For instance, a first multiwell plate 34 can be advanced from $P_1$ to $P_2$ while a second multiwell plate 34 remains in place at $P_3$. As a result, when $P_1$, $P_2$ and $P_3$ are each associated with different stations 12, multiwell plates 34 can be processed through different stations 12 at different rates. Further, different pin carriages 162 which make up a transport assembly can be included with independent systems which are assembled together to form the system. For instance, the first pin carriage 162A and the second pin carriage 162B can be included in a mother liquor deliver system and the third pin carriage 162C can be included in a drop formation system 32.

Crystal formation can be detected by examining each drop for the formation of crystals. In a preferred embodiment, crystals are detected and graded in the various wells for crystal quality. This may be done manually or by an automated device. Diversified Scientific, Inc. of Birmingham, Alabama manufactures CRYSTALSCORE™ which may be used to automate the scoring of crystal formation.

As described above, the system can be used to performed crystallization trials where various mother liquor are screened for their ability to crystallize a protein of interest. The crystallization trials frequently include a coarse screen followed by one or more fine screens. While the mother liquors used for the fine screens are often dependent on the results of the coarse screen, the mother liquors used for the coarse screen can be standard for each crystallization trial.

When the mother liquors are used to crystallize proteins, a preferred coarse screen preferably consists of the 15 sub-screens listed in Table 1. The number of mother liquors included in each sub-screen is also listed in Table 1. The composition of the mother liquors included each of these sub-screens is listed in FIG. 9. Mother liquors having the listed compositions can be obtained from Hampton Research of Laguna Niguel, California.

As illustrated in Table 1, a total of 480 mother liquors are associated with the sub-screens of the preferred coarse screen. Since 480 mother liquors are included in the coarse screen and since each plate preferably includes 48 wells, the coarse screen can be performed by processing only 10 plates through the system. Further, the sub-screens generally include 24 or 48 mother liquors. Accordingly, each plate can include from one to two sub-screens.

TABLE 1

| Screen | Number of mother liquors |
| --- | --- |
| Crystal screen I | 48 |
| Crystal screen II | 48 |
| Grid ammonium sulfate | 24 |
| Grid MPD | 24 |
| Grid sodium chloride | 24 |
| Grid PEG6000 | 24 |
| Grid PEG/lithium chloride | 24 |
| Sodium/potassium phosphate | 24 |
| PEG/ion screen | 48 |
| Membrane protein screen | 48 |
| Detergent screen I | 24 |
| Detergent screen II | 24 |
| Detergent screen III | 24 |
| Cryo screen | 48 |
| Low ionic strength screen | 24 |

Each of the mother liquors used for the coarse screen can be stored in one or more of the mother liquor storage banks. However, the number of mother liquors which may be needed for different fine screens is large enough that storage of these mother liquors impractical. Accordingly, the system can also include a station which forms the fine screen mother liquors from stock solutions and then delivers them into the wells of a plate. Alternatively, one or more external systems can be used to create the fine screen mother liquors from stock solutions and to deliver these mother liquors into the wells of one or more plates. These plates can then be processed through the system.

When an external system is used to form and deliver fine screen mother liquors, the system control logic needs to override the mother liquor delivery station in order to avoid doubling up on the delivery of mother liquor into the wells of a plate. As a result, the system control logic must be informed when a plate which already has mother liquor is in the system. An operator can use a user interface to inform the system control logic which one of the plates already has mother liquors delivered into the wells. Alternatively, an operator use a plate having a bar code which indicates that mother liquors are already present in the wells of the plate.

EXAMPLE 1

The system described above was used in a plurality of lysozyme crystallization experiments where lysozyme was crystallized in a mother liquor composition including 100 mM sodium acetate and 10% sodium chloride at a pH of 4.6. The volume of the hanging drop formed by the drop formation station was different for each experiment. FIGS. 10A–10D respectively illustrate crystal formed in hanging drops of 40 nL, 100 nL, 200 nL and 1000 nL. The crystals were formed regardless of the reduction in drop size. As a result, the system can be used with submicroliter hanging drop volumes.

EXAMPLE 2

The system described above was used in a crystallization trial where the mother liquor for crystallizing lysozyme was optimized. During the coarse screen, 480 crystallization experiments were performed using each of the 480 mother liquors disclosed in FIG. 9. The results from each of the 480 experiments were compared to one another to identify one or more crystallization experiments yielding crystals with the most desirable characteristics. One of the identified coarse screen experiments was associated with a mother liquor composed of 30% MPD (+/−2-methyl-2,4-pentanediol), 100 mM sodium acetate, 20 mM calcium chloride, at pH 4.6.

A fine screen consisting of 24 crystallization experiments was then performed. The composition of the mother liquors associated with each of the 24 crystallization experiments was selected relative to the composition of the mother liquor associated with the identified coarse screen experiment. The compositions of the 24 mother liquors selected for the crystallization experiments of the fine screen are listed in FIG. 11. The concentrations of certain components in each of the 24 mother liquors matched the concentration of these components in the identified coarse screen experiment. For instance, the mother liquor associated with the identified coarse screen experiment and the mother liquors for each of the fine screen crystallization experiments were all about 30% MPD and 100 mM sodium acetate. The concentrations of other components in the 24 mother liquors were varied over a range which encompassed the concentration of these same components in the identified coarse screen experiment. For instance, the concentration of calcium chloride was 20 mM in the identified coarse screen experiment but was varied from 12.5–27.5 mM in the 24 mother liquors. Similarly, the pH was 4.6 in the identified coarse screen crystallization experiment but was varied from 4.1 to 5.1 in the 24 mother liquors.

Each of the 24 fine screen crystallization experiments were compared to one another to identify the one or more crystallization experiments yielding the most desirable characteristics.

The foregoing examples and description of preferred embodiments of the present invention are provided for the purposes of illustration and description. The examples and preferred embodiments, however, are not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A method for forming crystallization experiments for a molecule, the method comprising:
   forming a plurality of crystallization experiments that comprise a molecule to be crystallized and a composition that varies among the plurality of crystallization experiments, the crystallization experiments having a volume less than 1 microliter, the volumes of the plurality of crystallization experiments varying among the experiments by less than 25 nL.

2. The method according to claim 1 wherein the molecule is a macromolecule.

3. The method according to claim 1 wherein the molecule is a protein.

4. The method according to claim 1 wherein the molecule has a molecular weight of at least 500 daltons.

5. The method according to claim 1 wherein the crystallization experiments have volumes less than 750 nL.

6. The method according to claim 1 wherein the crystallization experiments have volumes less than 500 nL.

7. The method according to claim 1 wherein the crystallization experiments have volumes less than 250 nL.

8. The method according to claim 1 wherein the crystallization experiments have volumes between 1 nL–750 nL.

9. The method according to claim 1 wherein the crystallization experiments have volumes between 1 nL–500 nL.

10. The method according to claim 1 wherein the crystallization experiments have volumes between 1 nL–250 nL.

11. The method according to claim 1 wherein the volumes of the plurality of crystallization experiments vary among the experiments by less than 20 nL.

12. The method according to claim 1 wherein the volumes of the plurality of crystallization experiments vary among the experiments by less than 15 nL.

13. The method according to claim 1 wherein the volumes of the plurality of crystallization experiments vary among the experiments by less than 10 nL.

14. The method according to claim 1 wherein the volumes of the plurality of crystallization experiments vary among the experiments by between 380 pL and 25 nL.

15. The method according to claim 1 wherein the volumes of the plurality of crystallization experiments vary among the experiments by between 380 pL and 20 nL.

16. The method according to claim 1 wherein the volumes of the plurality of crystallization experiments vary among the experiments by between 380 pL and 15 nL.

17. The method according to claim 1 wherein the volumes of the plurality of crystallization experiments vary among the experiments by between 380 pL and 10 nL.

18. The method according to claim 1 wherein the plurality of crystallization experiments comprise at least 24 different crystallization experiments.

19. The method according to claim 1 wherein the plurality of crystallization experiments comprise at least 36 different crystallization experiments.

20. The method according to claim 1 wherein the plurality of crystallization experiments comprise at least 48 different crystallization experiments.

21. The method according to claim 1 wherein the plurality of crystallization experiments comprise greater than 96 different crystallization experiments.

22. The method according to claim 1 wherein the plurality of crystallization experiments are formed in a multiwell plate.

23. The method according to claim 1 wherein the plurality of crystallization experiments are formed in a sitting drop multiwell plate.

24. The method according to claim 1 wherein the plurality of crystallization experiments are formed in a hanging drop multiwell plate.

25. A method for performing crystallization experiments for a molecule, the method comprising:
   forming a plurality of crystallization experiments that comprise a molecule to be crystallized and a composition that varies among the plurality of crystallization experiments, the crystallization experiments having a volume less than 1 microliter, the volumes of the plurality of crystallization experiments varying among the experiments by less than 25 nL;
   storing the plurality of crystallization experiments; and
   detecting crystal formation in the plurality of crystallization experiments.

26. The method according to claim 25 wherein detecting crystal formation in the crystallization experiments comprises characterizing the crystal formed.

27. The method according to claim 25 wherein detecting crystal formation in the crystallization experiments comprises characterizing the quality of a crystal structure of the crystal formed.

28. The method according to claim 25 wherein detecting crystal formation in the crystallization experiments comprises imaging the plurality of crystallization experiments.

29. The method according to claim 25 wherein detecting crystal formation in the crystallization experiments comprises imaging the plurality of crystallization experiments such that only a single image of each crystallization experiment is taken.

30. The method according to claim 25 wherein detecting crystal formation in the crystallization experiments comprises imaging the plurality of crystallization experiments without adjusting a focus of an optical system taking the images during the imaging.

31. The method according to claim 25 wherein the molecule is a macromolecule.

32. The method according to claim 25 wherein the molecule is a protein.

33. The method according to claim 25 wherein the molecule has a molecular weight of at least 500 daltons.

34. The method according to claim 25 wherein the crystallization experiments have volumes less than 750 nL.

35. The method according to claim 25 wherein the crystallization experiments have volumes less than 500 nL.

36. The method according to claim 25 wherein the crystallization experiments have volumes less than 250 nL.

37. The method according to claim 25 wherein the crystallization experiments have volumes between 1 nL–750 nL.

38. The method according to claim 25 wherein the crystallization experiments have volumes between 1 nL–500 nL.

39. The method according to claim 25 wherein the crystallization experiments have volumes between 1 nL–250 nL.

40. The method according to claim 25 wherein the volumes of crystallization experiments vary among the plurality of crystallization experiments by less than 20 nL.

41. The method according to claim 25 wherein the volumes of crystallization experiments vary among the plurality of crystallization experiments by less than 15 nL.

42. The method according to claim 25 wherein the volumes of crystallization experiments vary among the plurality of crystallization experiments by less than 10 nL.

43. The method according to claim 25 wherein the volumes of crystallization experiments vary among the plurality of crystallization experiments by between 380 pL and 25 nL.

44. The method according to claim 25 wherein the volumes of crystallization experiments vary among the plurality of crystallization experiments by between 380 pL and 20 nL.

45. The method according to claim 25 wherein the volumes of crystallization experiments vary among the plurality of crystallization experiments by between 380 nL and 15 nL.

46. The method according to claim 25 wherein the volumes of crystallization experiments vary among the plurality of crystallization experiments by between 380 pL and 10 nL.

47. The method according to claim 25 wherein the plurality of crystallization experiments comprise at least 24 different crystallization experiments.

48. The method according to claim 25 wherein the plurality of crystallization experiments comprise at least 36 different crystallization experiments.

49. The method according to claim 25 wherein the plurality of crystallization experiments comprise at least 48 different crystallization experiments.

50. The method according to claim 25 wherein the plurality of crystallization experiments comprise greater than 96 different crystallization experiments.

51. The method according to claim 25 wherein the plurality of crystallization experiments are performed in a multiwell plate.

52. The method according to claim 25 wherein the plurality of crystallization experiments are performed in a sitting drop multiwell plate.

53. The method according to claim 25 wherein the plurality of crystallization experiments are performed in a hanging drop multiwell plate.

54. The method according to claim 1 wherein the method further comprising solving the molecule's crystal structure by x-ray diffraction of a crystal of the molecule from one of the crystallization experiments.

55. The method according to claim 54 wherein the molecule is a macromolecule.

56. The method according to claim 54 wherein the molecule is a protein.

57. The method according to claim 54 wherein the drop has a volume of less than about 750 nL.

58. The method according to claim 54 wherein the drop has a volume of less than about 500 nL.

59. The method according to claim 54 wherein the drop has a volume of less than about 250 nL.

60. The method according to claim 25, the method further comprising solving the molecule's crystal structure by x-ray diffraction of one of the detected crystals.

61. The method according to claim 25 wherein the molecule is a macromolecule.

62. The method according to claim 25 wherein the molecule is a protein.

63. The method according to claim 25 wherein the drop has a volume of less than about 750 nL.

64. The method according to claim 25 wherein the drop has a volume of less than about 500 nL.

65. The method according to claim 25 wherein the drop has a volume of less than about 250 nL.

66. The method according to claim 1, wherein forming the plurality of crystallization experiments are performed in a single crystallization experiment device.

67. The method according to claim 1, wherein forming a plurality of crystallization experiments comprises forming at least 96 crystallizations in a single crystallization experiment device.

68. The method according to claim 67 wherein the single crystallization experiment device is a multiwell plate.

69. The method according to claim 67, wherein the molecule is a protein.

70. The method according to claim 67, wherein the crystallization experiments each have a volume less than 750 nL.

71. The method according to claim 67, wherein the crystallization experiments each have a volume less than 500 nL.

72. The method according to claim 67, wherein the crystallization experiments each have a volume less than 250 nL.

73. The method according to claim 72, wherein the molecule is a protein.

74. The method according to claim 1, wherein forming a plurality of crystallization experiments comprises forming more than 96 crystallizations in a single crystallization experiment device.

75. The method according to claim 1, wherein forming a plurality of crystallization experiments comprises forming at least 144 crystallizations in a single crystallization experiment device.

76. The method according to claim 75, wherein the molecule is a protein.

77. The method according to claim 75, wherein the crystallization experiments each have a volume less than 750 nL.

78. The method according to claim 75, wherein the crystallization experiments each have a volume less than 500 nL.

79. The method according to claim 25, wherein the crystallization experiments each have a volume less than 250 nL.

80. The method according to claim 79, wherein the molecule is a protein.

81. The method according to claim 1, wherein forming a plurality of crystallization experiments comprises forming at least 192 crystallizations in a single crystallization experiment device.

82. The method according to claim 1, wherein forming a plurality of crystallization experiments comprises forming at least 288 crystallizations in a single crystallization experiment device.

* * * * *